(12) United States Patent
Quattropani et al.

(10) Patent No.: US 10,995,090 B2
(45) Date of Patent: May 4, 2021

(54) SUBSTITUTED DIHYDROBENZOFURAN GLYCOSIDASE INHIBITORS

(71) Applicant: Asceneuron SA, Lausanne (CH)

(72) Inventors: Anna Quattropani, Rolle (CH); Santosh S. Kulkarni, Bangalore (IN); Awadut Gajendra Giri, Bangalore (IN)

(73) Assignee: Asceneuron SA, Lausanne (CH)

( * ) Notice: Subject to any disclaimer, the term of this patent is extended or adjusted under 35 U.S.C. 154(b) by 81 days.

(21) Appl. No.: 16/488,163

(22) PCT Filed: Aug. 24, 2017

(86) PCT No.: PCT/EP2017/071384
§ 371 (c)(1),
(2) Date: Aug. 22, 2019

(87) PCT Pub. No.: WO2018/153507
PCT Pub. Date: Aug. 30, 2018

(65) Prior Publication Data
US 2019/0388415 A1 Dec. 26, 2019

Related U.S. Application Data

(63) Continuation-in-part of application No. PCT/EP2017/054268, filed on Feb. 24, 2017, which
(Continued)

(30) Foreign Application Priority Data

Feb. 25, 2016 (IN) .............................. 201621006636
Feb. 25, 2016 (IN) .............................. 201621006643

(51) Int. Cl.
*C07D 471/04* (2006.01)
*C07D 401/12* (2006.01)
(Continued)

(52) U.S. Cl.
CPC .......... *C07D 471/04* (2013.01); *A61K 9/0019* (2013.01); *A61K 9/0048* (2013.01); *A61K 9/0073* (2013.01); *A61K 9/02* (2013.01); *A61K 9/06* (2013.01); *A61K 9/19* (2013.01); *A61K 9/2009* (2013.01); *A61K 9/2059* (2013.01); *A61K 9/4825* (2013.01); *A61K 31/496* (2013.01); *A61K 31/497* (2013.01); *A61K 31/4985* (2013.01); *A61P 25/28* (2018.01); *C07D 401/12* (2013.01); *C07D 401/14* (2013.01); *C07D 403/12* (2013.01); *C07D 405/06* (2013.01); *C07D 405/10* (2013.01); *C07D 405/12* (2013.01); *C07D 405/14* (2013.01); *C07D 407/12* (2013.01); *C07D 413/12* (2013.01); *C07D 413/14* (2013.01); *C07D 417/06* (2013.01); *C07D 417/12* (2013.01); *C07D 417/14* (2013.01); *C07D 475/04* (2013.01); *C07D 487/04* (2013.01); *C07D 491/048* (2013.01);
(Continued)

(58) Field of Classification Search
CPC .. C07D 471/04; C07D 401/12; C07D 401/14; C07D 403/12; C07D 405/12; C07D 405/14; C07D 407/12; C07D 413/12; C07D 413/14; C07D 417/06; C07D 417/12; C07D 417/14; C07D 475/04; C07D 487/04; C07D 491/048; C07D 495/04; C07D 498/04; C07D 513/04; A61P 25/28; A61K 9/0019; A61K 9/0048; A61K 9/0073; A61K 9/02; A61K 9/06; A61K 9/19; A61K 9/2009; A61K 9/2059; A61K 9/4825; A61K 31/496; A61K 31/497; A61K 31/4985
See application file for complete search history.

(56) References Cited

U.S. PATENT DOCUMENTS

| 3,299,067 A | 1/1967 | Gilbert et al. |
| 3,457,263 A | 7/1969 | Regnier et al. |

(Continued)

FOREIGN PATENT DOCUMENTS

| CN | 1791594 A | 6/2006 |
| CN | 103435606 | 12/2013 |

(Continued)

OTHER PUBLICATIONS

Abdel-Magid, A. F. et al. "Reductive Amination of Aldehydes and Ketones with Sodium Triacetoxyborohydride. Studies on Direct and Indirect Reductive Amination Procedures" J. Org. Chem., (1996), 61, pp. 3849-3862.
(Continued)

*Primary Examiner* — Timothy R Rozof
(74) *Attorney, Agent, or Firm* — Cooley LLP; Ivor R. Elrifi; Thomas J. Paxton

(57) ABSTRACT

Compounds of formula (I), wherein R', R", R, X, W, Q, n, and m have the meaning according to the claims, can be employed, inter alia, for the treatment of tauopathies and Alzheimer's disease.

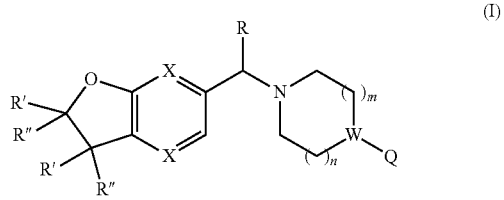

16 Claims, No Drawings

Related U.S. Application Data is a continuation-in-part of application No. PCT/EP2017/054280, filed on Feb. 24, 2017.

(51) Int. Cl.

| | | |
|---|---|---|
| *C07D 401/14* | (2006.01) |
| *C07D 403/12* | (2006.01) |
| *C07D 405/12* | (2006.01) |
| *C07D 405/14* | (2006.01) |
| *C07D 407/12* | (2006.01) |
| *C07D 413/12* | (2006.01) |
| *C07D 413/14* | (2006.01) |
| *C07D 417/06* | (2006.01) |
| *C07D 417/12* | (2006.01) |
| *C07D 417/14* | (2006.01) |
| *C07D 475/04* | (2006.01) |
| *C07D 487/04* | (2006.01) |
| *C07D 491/048* | (2006.01) |
| *C07D 495/04* | (2006.01) |
| *C07D 498/04* | (2006.01) |
| *C07D 513/04* | (2006.01) |
| *A61P 25/28* | (2006.01) |
| *C07D 405/06* | (2006.01) |
| *A61K 9/00* | (2006.01) |
| *A61K 9/02* | (2006.01) |
| *A61K 9/06* | (2006.01) |
| *A61K 9/19* | (2006.01) |
| *A61K 9/20* | (2006.01) |
| *A61K 9/48* | (2006.01) |
| *A61K 31/496* | (2006.01) |
| *A61K 31/497* | (2006.01) |
| *A61K 31/4985* | (2006.01) |
| *C07D 405/10* | (2006.01) |

(52) U.S. Cl.
CPC ......... *C07D 495/04* (2013.01); *C07D 498/04* (2013.01); *C07D 513/04* (2013.01); *C07B 2200/09* (2013.01)

(56) References Cited

U.S. PATENT DOCUMENTS

| | | |
|---|---|---|
| 3,485,757 A | 12/1969 | Shapiro |
| 3,489,757 A | 1/1970 | Koppe et al. |
| 4,600,025 A | 7/1986 | Grigg et al. |
| 5,935,974 A | 8/1999 | Rae et al. |
| 7,582,769 B2 | 9/2009 | Murray et al. |
| 8,008,326 B2 | 8/2011 | Borza et al. |
| 9,120,781 B2 | 9/2015 | Li et al. |
| 10,336,775 B2 | 7/2019 | Quattropani et al. |
| 10,344,021 B2 | 7/2019 | Quattropani et al. |
| 2004/0106645 A1 | 6/2004 | Blackburn et al. |
| 2006/0287340 A1 | 12/2006 | Moriya et al. |
| 2008/0300276 A1 | 12/2008 | Borza et al. |
| 2009/0012078 A1 | 1/2009 | Andrews et al. |
| 2009/0163545 A1 | 6/2009 | Goldfarb |
| 2010/0022517 A1 | 1/2010 | Richards et al. |
| 2011/0053982 A1 | 3/2011 | Fay et al. |
| 2011/0060012 A1 | 3/2011 | Meyers et al. |
| 2011/0060019 A1 | 3/2011 | Murray et al. |
| 2012/0208808 A1 | 8/2012 | Buchstaller et al. |
| 2016/0031871 A1 | 2/2016 | Yu et al. |
| 2019/0055233 A1 | 2/2019 | Quattropani et al. |
| 2019/0055239 A1 | 2/2019 | Quattropani et al. |

FOREIGN PATENT DOCUMENTS

| | | |
|---|---|---|
| EP | 2301936 | 3/2011 |
| EP | 2687507 | 1/2014 |
| FR | 1311316 | 12/1962 |
| JP | 2010/270034 | 12/2010 |
| WO | WO1993/021181 | 10/1993 |
| WO | WO1997/043279 | 11/1997 |
| WO | WO1998/046590 | 10/1998 |
| WO | WO99/21850 | 5/1999 |
| WO | WO02/094799 | 11/2002 |
| WO | WO2003/092678 | 11/2003 |
| WO | WO2004/002481 | 1/2004 |
| WO | WO2004/005293 | 1/2004 |
| WO | WO2004/022558 | 3/2004 |
| WO | WO2004/094380 | 11/2004 |
| WO | WO2005/110982 | 11/2005 |
| WO | WO2006/092049 | 9/2006 |
| WO | WO2007/115077 | 10/2007 |
| WO | WO2007/135398 | 11/2007 |
| WO | WO2007/146122 | 12/2007 |
| WO | WO2008/012623 | 1/2008 |
| WO | WO2008/025170 | 3/2008 |
| WO | WO2009/011904 | 1/2009 |
| WO | WO2009/053373 | 4/2009 |
| WO | WO2009/131926 | 10/2009 |
| WO | WO2010/018868 | 2/2010 |
| WO | WO2010/021381 | 2/2010 |
| WO | WO2010/022517 | 3/2010 |
| WO | WO2010/026989 | 3/2010 |
| WO | WO2010/089127 | 8/2010 |
| WO | WO2010/101949 | 9/2010 |
| WO | WO2010/108115 | 9/2010 |
| WO | WO2010/108268 | 9/2010 |
| WO | WO2010/151318 | 12/2010 |
| WO | WO2011/140640 | 11/2011 |
| WO | WO2012/037298 | 3/2012 |
| WO | WO2012/061927 | 5/2012 |
| WO | WO2012/062157 | 5/2012 |
| WO | WO2012/062759 | 5/2012 |
| WO | WO2012/083435 | 6/2012 |
| WO | WO2012/117219 | 9/2012 |
| WO | WO2013/028715 | 2/2013 |
| WO | WO2013/066729 | 5/2013 |
| WO | WO2014/023723 | 2/2014 |
| WO | WO2014/032187 | 3/2014 |
| WO | WO2014/159234 | 10/2014 |
| WO | WO2015/083028 | 6/2015 |
| WO | WO2015/128333 | 9/2015 |
| WO | WO2015/164508 | 10/2015 |
| WO | WO2016/030443 | 3/2016 |
| WO | WO2017/001660 | 1/2017 |
| WO | WO2017/076900 | 5/2017 |
| WO | WO2017/087858 | 5/2017 |
| WO | WO2017/087863 | 5/2017 |
| WO | WO2017/091818 | 6/2017 |
| WO | WO2017/106254 | 6/2017 |
| WO | WO2017/144633 | 8/2017 |
| WO | WO2017/144635 | 8/2017 |
| WO | WO2017/144637 | 8/2017 |
| WO | WO2017/144639 | 8/2017 |
| WO | WO2018/026371 | 2/2018 |
| WO | WO2018/109198 | 6/2018 |
| WO | WO2018/109202 | 6/2018 |
| WO | WO2018/140299 | 8/2018 |
| WO | WO2018/141984 | 8/2018 |
| WO | WO2018/153508 | 8/2018 |
| WO | WO2018/154133 | 8/2018 |
| WO | WO2018/217558 | 11/2018 |

OTHER PUBLICATIONS

Albertson, N. F. "Alkylation with Non-ketonic Mannich Bases. Aminothiazoles and Pyrrole" J. Am. Chem. Soc., 1948, 70(2), 669-670.

Andres, J. I. et al. "Synthesis, Evaluation, and Radiolabeling of New Potent Positive Allosteric Modulators of the Metabotropic Glutamate Receptor 2 as Potential Tracers for Positron Emission Tomography Imaging" J. Med. Chem., (2012), 55, pp. 8685-8699.

Augustine, J. K. et al. "Propylphosphonic anhydride (T3P®): an efficient reagent for the one-pot synthesis of 1,2,4-oxadiazoles, 1,3,4-oxadiazoles, and 1,3,4-thiadiazoles" Tetrahedron, (2009), 65, pp. 9989-9996.

(56) References Cited

OTHER PUBLICATIONS

Bastin, R. J. et al. "Salt Selection and Optimisation Procedures for Pharmaceutical New Chemical Entities", Organic Process Research & Development, 2000, 4, 427-435.
Berge, S. M. et al. "Pharmaceutical Salts", Journal of Pharmaceutical Sciences, 1977, 66(1), 1-19.
Biscoe, M. R. et al. "A New Class of Easily Activated Palladium Precatalysts for Facile C—N Cross-Coupling Reactions and Low Temperature Oxidative Addition of Aryl Chlorides", J. Am. Chem. Soc., 2008, 130, 6686-6687.
Bohnert, T. et al. "Plasma Protein Binding: From Discovery to Development", J. Pharmaceutical Sciences, 2013, 102, 2953-2994.
Bras, N. F. et al. "Glycosidase inhibitors: a patent review (2008-2013)" Expert Opinion on Therapeutic Patents, vol. 24, No. 8, 2014, pp. 857-874.
Bundgaard, H. "Design and Application of Prodrugs", from a Textbook of Drug Design and Development Chapter 5, Harwood Academic Publishers, 1991, 113-191.
Calcagno, A. M. "Comparison of Drug Transporter Levels in Normal Colon, Colon Cancer, and Caco-2 Cells: Impact on Drug Disposition and Discovery", Mol. Pharm., 2006, 3(1), 87-93.
CAS Registry (Online) Nos. 948053-91-6; 540512-02-5; 697229-62-2; 346662-52-0; 345992-64-5 (STN database summary sheets) Sep. 26, 2007.
"Chemical Encyclopedia", vol. 4, pp. 990-993, 1988. (Machine translation attached).
Chen, Y. et al. "Discovery of new acetylcholinesterase and butyrylcholinesterase inhibitors through structurebased virtual screening", RSC Advances, 2017, 7(6), 3429-3438.
Collet, A. "Resolution of Racemates: Did you say 'Classical?'", Angewandte Chemie International Edition, 1998, 37(23), 3239-3241.
Dassanayaka, S. and Jones, S. "O-GlcNAc and the cardiovascular system", Pharmacology & Therapeutics, 2014, 142, 62-71.
Database registry (online) Chemical abstract service, Columbus, Ohio, US; Dec. 6, 2011, "Piperazine, 1-[1-(1,3-benzodioxol-5-yl)ethyl]-4-(5-bromo-6-methoxy-2-pyridinyl)-", Database accession No. 1349611-60-4.
Database Pubchem Compound (Online) NCBI; Jan. 24, 2012, XP002768130, Database accession No. CID 54914491.
Database PubChem Compound (Online) NCBI; May 28, 2009; XP002768131, Database accession No. CID 28798635.
Database PubChem Compound, NCBI; 9. Apr. 2016; XP002768133, Database accession No. CID 118902929.
Database Registry, Chemical Abstracts Service, 2016, CID120907609, 10 pages.
Database Registry, Chemical Abstracts Service, Jan. 11, 2017, XP002768132, Database accession No. 2055841-81-9.
Dorfmueller, H. C. et al. "Cell-Penetrant, Nanomolar O-GlcNAcase Inhibitors Selective against Lysosomal Hexosaminidases", Chem. Biol., 2010, 17, 1250-1255.
Dubois, B. et al. "Preclinical Alzheimer's disease: Definition, natural history, and diagnostic criteria", Alzheimers Dement., 2016, 12, 292-323.
Dubois, B. et al. "Advancing research diagnostic criteria for Alzheimer's disease: the IWG-2 criteria", Lancet Neurol., 2014, 13, 614-629.
Dyatkin, A.B. et al. "Determination of the Absolute Configuration of a Key Tricyclic Component of a Novel Vasopressin Receptor Antagonist by Use of Vibrational Circular Dichroism", Chirality, 2002, 14, 215-219.
Ellman, J. A et al. "N-tert-Butanesulfinyl Imines: Versatile Intermediates for the Asymmetric Synthesis of Amines" Acc. Chem. Res. (2002), 35, pp. 984-995.
Fors, B. P. et al. "A Highly Active Catalyst for Pd-Catalyzed Amination Reactions: Cross-Coupling Reactions Using Aryl Mesylates and the Highly Selective Monoarylation of Primary Amines Using Aryl Chlorides", J. Am. Chem. Soc., 2008, 130, 13552-13554.
Frings, M. et al. "Sulfoximines from a Medicinal Chemist's Perspective: Physicochemical and in vitro Parameters Relevant for Drug Discovery", European Journal of Medicinal Chemistry, 2017, 126, 225-245.
Goho, A. "Tricky Business", Science News, 2004, 166(8), 122-124.
Golub, T. R. et al. "Molecular Classification of Cancer: Class Discovery and Class Prediction by Gene Expression Monitoring", Science, 1999, 286, 531-537.
Gould, P. L. "Salt selection for basic drugs", International Journal of Pharmaceutics, 1986, 33, 201-217.
Graham, D. L. et al. "Increased O-GlcNAcylation reduces pathological tau without affecting its normal phosphorylation in a mouse model of tauopathy", Neuropharmacology, 2014, 79, 307-313.
Gujjar, R. et al. "Lead Optimization of Aryl and Aralkyl Amine-Based Triazolopyrimidine Inhibitors of Plasmodium falciparum Dihydroorotate Dehydrogenase with Antimalarial Activity in Mice", J. Med. Chem., 2011, 54 (11), 3935-3949.
Haleblian, J.; McCrone, W. "Pharmaceutical Applications of Polymorphism", J. Pharm. Sci., 1969, 58(8), 911-929.
Haleblian, J. "Characterization of Habits and Crystalline Modification of Solids and Their Pharmaceutical Applications", J. Pharm. Sci., 1975, 64(8), 1269-1288.
Hemming, K. "Product Class 6: 1,2,4-Oxadizoles" Science of Synthesis, (2004), 13(6), pp. 127-184.
Jakopin, Z. et al. "Recent Advances in the Synthesis of 1,2,4- and 1,3,4-Oxadiazoles" Current Organic Chemistry, (2008), 12(10), pp. 850-898.
Kempson, J. "Name Reactions in Heterocyclic Chemistry II" John Wiley & Sons. Eds. Jie Jack Li and E. J. Corey, (2011), pp. 299-308.
Kim, E. J. et al. "Enzymatic characterization of O-GlcNAcase isoforms using a fluorogenic GlcNAc substrate", Carbohydrate Research, 2006, 341(8), 971-982.
Kim, E. J. "Chemical Arsenal for the Study of O-GlcNAc", Molecules, 2011, 16, 1987-2022.
Knapp, S. et al. "An Allosamizoline/ Glucosamine Hybrid NAGase Inhibitor", Synlett, 1997, 5, 435-436.
Lefebvre, T. "Recall sugars, forget Alzheimer's", Nature Chemical Biology, 2012, 8(4), 325-326.
Legros, J. et al. "Applications of Catalytic Asymmetric Sulfide Oxidations to the Syntheses of Biologically Active Sulfoxides", Adv. Synth. Catal., 2005, 347, 19-31.
Liu, X. et al. "Rational Use of Plasma Protein and Tissue Binding Data in Drug Design", J. Med. Chem. 2014, 57, 8238-8248.
Marwaha, A. et al. "Bioisosteric Transformations and Permutations in the Triazolopyrimidine Scaffold to Identify the Minimum Pharmacophore Required for Inhibitory Activity against Plasmodium falciparum Dihydroorotate Dehydrogenase", J. Med. Chem., 2012, 55(17), 7425-7436.
Mariappa, D. et al. "A mutant O-GlcNAcase as a probe to reveal global dynamics of the Drosophila O-GlcNAc developmental proteome", Biochem J., 2015, 470(2), 255-262.
Marotta, N. P. et al., "O-GlcNAc modification blocks the aggregation and toxicity of the Parkinson's disease associated protein α-synuclein", Nat. Chem, 2015, 7(11), 913-920.
Masuda, N. et al. "Studies of nonnucleoside HIV-1 reverse transcriptase inhibitors. Part 1: Design and synthesis of thiazolidenebenzenesulfonamides", Bioorg. Med. Chem., 2004, 12, 6171-6182.
Mittur A. "Piribedil: Antiparkinsonian Properties and Potential Clinical Utility in Dopaminergic Disorders" Current Drug Therapy (2011), 6, pp. 17-34.
Moradi-Afrapoli, F. et al. "In vitro α-glucosidase inhibitory activity of phenolicconstituents from aerial parts of Polygonum hyrcanicum", DARU Journal of Pharmaceutical Sciences, 2012, 20(1), 37, 6 pages.
Nandi, A. et al. "Global Identification of O-GlcNAc-Modified Proteins", Anal. Chem., 2006, 78, 452-458.
Nelson, P. T. et al. "Correlation of Alzheimer Disease Neuropathologic Changes With Cognitive Status: A Review of the Literature", J. Neuropathol. Exp. Neurol., 2012, 71(5), 362-381.
Nettekoven, M. et al. "Synthetic Access to 2-Amido-5-aryl-8-methoxy-triazolopyridine and 2-Amido-5-morpholino-8-methoxy-

(56) References Cited

OTHER PUBLICATIONS triazolopyridine Derivatives as Potential Inhibitors of the Adenosine Receptor Subtypes", Synthesis, 2003, 1649-1652.
Obach, R. S. "Prediction of human clearance of twenty-nine drugs from hepatic microsomal intrinsic clearance data: and examination of in vitro half-life approach and nonspecific binding to microsomes", Drug. Metab. Dispos., 1999, 27(11), 1350-1359.
Okamura, H. et al. "Rhodium-Catalyzed Imination of Sulfoxides and Sulfides: Efficient Preparation of N-Unsubstituted Sulfoximines and Sulfilimines", Organic Letters, 2004, 6, 1305-1307.
O'Mahony, G. E. et al. "Synthesis of enantioenriched sulfoxides" Arkivoc, 2011, 1-110.
Orain, D. et al. "Synthesis of Orthogonally Protected 2,6-Diazaspiro[3.5]nonane and 2,6-Diazaspiro[3.4]octane Analogues as Versatile Building Blocks in Medicinal Chemistry", Synlett, 2015, 26(13), 1815-1818.
Papillon, J. P. N. et al. "Discovery of N-[5-(6-Chloro-3-cyano-1-methyl-1H-indol-2-yl)-pyridin-3-ylmethyl]-ethanesulfonamide, a Cortisol-Sparing CYP11B2 Inhibitor that Lowers Aldosterone in Human Subjects", J. Med. Chem., 2015, 58(23), 9382-9394.
Park, M.-J. et al. "High Glucose-induced O-GlcNAcylated Carbohydrate Response Element-binding Protein (ChREBP) Mediates Mesangial Cell Lipogenesis and Fibrosis", J. Biol. Chem., 2014, 289, 13519-13530.
Rouhi, A. M. et al. "The Right Stuff: From Research and Development to the Clinic, Getting Drug Crystals Right is Full of Pitfalls." Chem. Eng. News. (2003):32-35.
SantaCruz, K. et al. "Tau Suppression in a Neurodegenerative Mouse Model Improves Memory Function", Science, 2005, 309, 476-481.
Serajuddin, A. T. M. "Salt formation to improve drug solubility", Advanced Drug Delivery Reviews, 2007, 59(7), 603-616.
Shan, X. et al. "Reduced protein O-glycosylation in the nervous system of the mutant SOD1 transgenic mouse model of amyotrophic lateral sclerosis", Neuroscience Letters, 2012, 516, 296-301.
Shen, Q. et al. "Hydroxycoumarin Derivatives: Novel and Potent α-Glucosidase Inhibitors", J. Med. Chem., 2010, 53(23), 8252-8259.
Shirude, P. et al. "Lead Optimization of 1,4-Azaindoles as Antimycobacterial Agents", J. Med. Chem., 2014, 57(13), 5728-5737.
Sippy, K. B. et al. "Preparation and characterization of N-(3-pyridinyl) spirocyclic diamines as ligands for nicotinic acetylcholine receptors", Bioorganic & Med. Chemistry Letters, 2009, 19(6), 1682-1685.
Skedelj, V. et al. "Discovery of the first inhibitors of bacterial enzyme D-aspartate ligase from Enterococcus faecium (Asl$_{fm}$)", Eur. J. Med. Chem., 2013, 67, 208-220.
Song, S. et al. "Efficient and Practical Oxidative Bromination and Iodination of Arenes and Heteroarenes with DMSO and Hydrogen Halide: A Mild Protocol for Late-Stage Functionalization", Org. Lett., 2015, 17(12), 2886-2889.
Sperling, R. A. et al. "Toward defining the preclinical stages of Alzheimer's disease: Recommendations from the National Institute on Aging-Alzheimer's Association workgroups on diagnostic guidelines for Alzheimer's disease", Alzheimers Dement., 2011, 7, 280-292.
Spillantini, M. G.; Goedert, M. "Tau pathology and neurodegeneration", Lancet Neurol., 2013, 12, 609-622.
Tamura, B. K. et al. "Weight Loss in Patients with Alzheimer's Disease" J. Nutrition for the Elderly (2008), 26(3-4), pp. 21-38.
Tan, H. et al. "Rational Screening Approach for Classical Chiral Resolution under Thermodynamic Equilibrium: A Case Study of Diphenyl-Substituted N-Methyl-Piperazine", Organic Process Research and Development, 2011, 15(1), 53-63.
Tanuwidjaja, J. et al. "One-Pot Asymmetric Synthesis of Either Diastereomer of tert-Butanesulfinyl-protected Amines from Ketones", J. Org. Chem. 2007, 72, 626-629.
The U. S. Pharmacopeia 38—National Formulary 35 Chapter 941, Characterization of crystalline and partially crystalline solids by X-ray powder diffraction (XRPD) Official May 1, 2015, 427-431.
Thiel, O. R. et al. "Practical Synthesis of a Vanilloid Receptor-1 Antagonist" J. Org. Chem., (2008), 73(9), pp. 3508-3515.
Trapannone, R. et al. "O-GlcNAc transferase inhibitors: current tools and future challenges", Biochemical Society Transactions, 2016, 44(1), 88-93.
Vasudevan, A. et al. "Identification of aminopiperidine benzamides as MCHr1 antagonists", Bioorganic & Medicinal Chemistry Letters, 2005, 15(14), 3412-3416.
Volpe, D. A. "Application of Method Suitability for Drug Permeability Classification", The AAPS Journal, 2010, 12(4), 670-678.
Wall, G. M. "Pharmaceutical Applications of Drug Crystal Studies", Pharm. Manuf., 1986, 3, 32-42.
Wang, Z. et al. "Enrichment and Site Mapping of O-Linked N-Acetylglucosamine by a Combination of Chemical/Enzymatic Tagging, Photochemical Cleavage, and Electron Transfer Dissociation Mass Spectrometry", Mol. Cell Proteomics, 2010, 9(1), 153-160.
Waterman, K. C. "Improved Protocol and Data Analysis for Accelerated Shelf-Life Estimation of Solid Dosage Forms", Pharm. Res., 2007, 24(4), 780-790.
Weinberg, K. et al. "Synthesis and differential functionalisation of pyrrolidine and piperidine based spirodiamine scaffolds", Tetrahedron, 2013, 69(23), 4694-4707.
Wermuth, C. G. et al. "Designing Prodrugs and Bioprecursors I: Carrier Prodrugs", The Practice of Medicinal Chemistry: Chapter 31, Academic Press, 1996, 671-696.
Wiessner et al. "A novel non-carbohydrate o-linked beta-n-acetylglucosaminidase inhibitor increases tau o-glcnacylation In vivo", Abstracts of the Annual Meeting of the Society for Neuroscience, Society for Neuroscience, 2013, 43, 2 pages.
Williams, D. R. et al. "Pathological tau burden and distribution distinguishes progressive supranuclear palsy-parkinsonism from Richardson's syndrome", Brain, 2007, 130, 1566-1576.
Yoshida, M. et al. "Study of biodegradable copoly(L-lactic acid/glycolic acid) formulations with controlled release of Z-100 for application in radiation therapy", Int. J. Pharm., 1995, 115, 61-67.
Yuzwa, S. A. et al. "Mapping O-GlcNAc modification sites on tau and generation of a site-specific O-GlcNAc tau antibody", Amino Acids, 2011, 40, 857-868.
Yuzwa, S. A. et al. "A potent mechanism-inspired O-GlcNAcase inhibitor that blocks phosphorylation of tau in vivo", Nat. Chem. Biol., 2008, 4(8), 483-490.
Yuzwa, S. A. et al. "increasing O-GlcNAc slows neurodegeneration and stabilizes tau against aggregation", Nat. Chem. Biol., 2012, 8(4), 393-399.
Zenzola, M. et al. "Transfer of Electrophilic NH Using Convenient Sources of Ammonia: Direct Synthesis of NH Sulfoximines from Sulfoxides", Angew. Chem. Int. Ed., 2016, 55, 7203-7207.
U.S. Appl. No. 16/078,155, filed Aug. 21, 2018.
U.S. Appl. No. 16/078,159, filed Aug. 21, 2018.
U.S. Appl. No. 16/079,162, filed Aug. 23, 2018.
U.S. Appl. No. 16/412,689, filed May 15, 2019.
U.S. Appl. No. 16/488,139, filed Aug. 22, 2019.
Hiroshi Yamanaka, Hiroshi Miyazaki and Naomi chi Murakami, Chemical Abstract, "Separation of optical isomers", Japan, Gakkai Shopping Santa, 1989, No. 6, pp. 8, 9, 124, 212, and 213 (21 pages).

SUBSTITUTED DIHYDROBENZOFURAN GLYCOSIDASE INHIBITORS

RELATED APPLICATIONS

This application is a U.S. National Phase application, filed under U.S.C. § 371(c), of International Application No. PCT/EP2017/071384, filed Aug. 24, 2017, which claims priority to, and the benefit of, International Application No. PCT/EP2017/054268, filed Feb. 24, 2017, which claims the benefit of, and priority to, Indian Patent Application No. 201621006636, filed Feb. 25, 2016, and International Application No. PCT/EP2017/054280, filed Feb. 24, 2017, which claims the benefit of, and priority to, Indian Patent Application No. 201621006643, filed Feb. 25, 2016. Each of these documents is incorporated by reference herein in its entirety for all purposes.

The present invention relates to a medicament comprising a compound of formula (I)

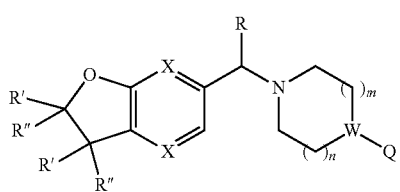

(I)

wherein R, R', R", X, W, Q, n and m have the meaning according to the claims, and/or physiologically acceptable salts, tautomers, solvates, stereoisomers and derivatives thereof. The compounds of formula (I) can be used as glycosidase inhibitors. Objects of the invention are also pharmaceutical compositions comprising the compounds of formula (I), and the use of the compounds of formula (I) for the treatment of one or more tauopathies and Alzheimer's disease.

A wide range of cellular proteins, both nuclear and cytoplasmic, are post-translationally modified by the addition of the monosaccharide 2-acetamido-2-deoxy-β-D-glucopyranoside (β-N-acetyl glucosamine) which is attached via an O-glycosidic linkage. This modification is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGTase). A second enzyme, known as O-GlcNAcase, removes this post-translational modification to liberate proteins making the O-GlcNAc-modification a dynamic cycle occurring several times during the lifetime of a protein.

O-GlcNAc-modified proteins regulate a wide range of vital cellular functions including, for example, transcription, proteasomal degradation and cellular signaling. O-GlcNAc is also found on many structural proteins. For example, it has been found on a number of cytoskeletal proteins, including neurofilament proteins, synapsins, synapsin-specific clathrin assembly protein AP-3 and Ankyrin-G. O-GlcNAc modification has been found to be abundant in the brain. It has also been found on proteins clearly implicated in the etiology of several diseases including tauopathies, Alzheimer's disease (AD), synucleinopathies, Parkinson's disease, amyotrophic lateral sclerosis, and cancer.

For example, it is well established that AD and a number of related tauopathies including Down's Syndrome, progressive supranuclear palsy (PSP), Pick's disease, corticobasal degeneration (CBD), argyrophilic grain disease (AGD), globular glial tauopathy (GGT), frontotemporal dementia and parkinsonism linked to chromosome-17 (FTLD-17, Niemann-Pick Type C disease are characterized, in part, by the development of neurofibrillary tangles (NFTs). NFTs are also a histopathological hallmark of chronic traumatic encephalopathy that is a consequence of traumatic brain injury. These NFTs are aggregates of paired helical filaments (PHFs) and are composed of an abnormal form of the cytoskeletal protein "tau". Normally, tau stabilizes a key cellular network of microtubules that is essential for distributing proteins and nutrients within neurons. In AD patients, however, tau becomes hyperphosphorylated, disrupting its normal function, forming PHFs and ultimately aggregating to form NFTs. Six isoforms of tau are found in the human brain. In AD patients, all six isoforms of tau are found in NFTs, and all are markedly hyperphosphorylated. Tau in healthy brain tissue bears only 2 or 3 phosphate groups, whereas those found in the brains of AD patients bear, on average, 8 phosphate groups. A clear parallel between NFT levels in the brains of AD patients and the severity of dementia strongly supports a key role for tau dysfunction in AD. The precise causes of this hyperphosphorylation of tau remain elusive. Accordingly, considerable effort has been dedicated toward: a) elucidating the molecular physiological basis of tau hyperphosphorylation; and b) identifying strategies that could limit tau hyperphosphorylation in the hope that these might halt, or even reverse, the progression of tauopathies and Alzheimer's disease. Several lines of evidence suggest that up-regulation of a number of kinases may be involved in hyperphosphorylation of tau, although very recently, an alternative basis for this hyperphosphorylation has been advanced.

In particular, it has recently emerged that phosphate levels of tau are regulated by the levels of O-GlcNAc on tau. The presence of O-GlcNAc on tau has stimulated studies that correlate O-GlcNAc levels with tau phosphorylation levels. The recent interest in this field stems from the observation that O-GlcNAc modification has been found to occur on many proteins at amino acid residues that are also known to be phosphorylated. Consistent with this observation, it has been found that increases in phosphorylation levels result in decreased O-GlcNAc levels and conversely, increased O-GlcNAc levels correlate with decreased phosphorylation levels. This reciprocal relationship between O-GlcNAc and phosphorylation has been termed the "Yin-Yang hypothesis" and has gained strong biochemical support by the recent discovery that the enzyme OGTase forms a functional complex with phosphatases that act to remove phosphate groups from proteins. Like phosphorylation, O-GlcNAc is a dynamic modification that can be removed and reinstalled several times during the lifespan of a protein. Suggestively, the gene encoding O-GlcNAcase has been mapped to a chromosomal locus that is linked to AD. Hyperphosphorylated tau in human AD brains has markedly lower levels of O-GlcNAc than are found in healthy human brains. Very recently, it has been shown that O-GlcNAc levels of soluble tau protein from human brains affected with AD are markedly lower than those from healthy brain. Furthermore, PHF from diseased brain was suggested to lack completely any O-GlcNAc modification whatsoever. The molecular basis of this hypoglycosylation of tau is not known, although it may stem from increased activity of kinases and/or dysfunction of one of the enzymes involved in processing O-GlcNAc. Supporting this latter view, in both PC-12 neuronal cells and in brain tissue sections from mice, a nonselective N-acetylglucosaminidase inhibitor was used to increase tau O-GlcNAc levels, whereupon it was observed that phosphorylation levels decreased. Moreover, it has been described that the O-GlcNAc modification of tau directly inhibits its aggregation without perturbing the conformational properties of tau monomers. The implication of these collective results is that by maintaining healthy O-GlcNAc levels in AD patients, such as by inhibiting the action of O-GlcNAcase (OGA), one should be able to block hyperphosphorylation of tau and all of the associated effects of tau hyperphosphorylation, including the formation of NFTs and downstream effects. However, because the proper functioning of the lysosomal β-hexosaminidases is critical, any potential therapeutic intervention for the treatment of AD that blocks the action of O-GlcNAcase would have to avoid the concomitant inhibition of both lysosomal hexosaminidases A and B.

Consistent with the known properties of the hexosamine biosynthetic pathway, the enzymatic properties of O-GlcNAc transferase (OGTase), and the reciprocal relationship between O-GlcNAc and phosphorylation, it has been shown that decreased glucose availability in brain leads to tau hyperphosphorylation. The gradual impairment of glucose transport and metabolism leads to decreased O-GlcNAc and hyperphosphorylation of tau (and other proteins). Accordingly, the inhibition of O-GlcNAcase should compensate for the age-related impairment of glucose metabolism within the brains of health individuals as well as patients suffering from AD or related neurodegenerative diseases.

These results suggest that a malfunction in the mechanisms regulating tau O-GlcNAc levels may be vitally important in the formation of NFTs and associated neurodegeneration. Good support for blocking tau hyperphosphorylation as a therapeutically useful intervention comes from studies showing that when transgenic mice harboring human tau are treated with kinase inhibitors, they do not develop typical motor defects and, in another case, show a decreased level of insoluble tau.

These studies provide a clear link between lowering tau phosphorylation levels and alleviating AD-like behavioral symptoms in a murine model of this disease.

There is evidence indicating that the modification with O-GlcNAc may have a general function in preventing harmful protein aggregation. This has been directly demonstrated for the tau protein and also for the protein alpha-synuclein that is a toxic aggregating protein associated with synucleinopathies, including Parkinson's disease. Two other aggregating proteins that are associated with amyotrophic lateraly sclerosis (Tar DNA binding protein-43 (TDP-43) and superoxide-dismutase I (SOD-I)) and frontotemporal lobar degeneration (TDP-43) are known to carry the O-GlcNAc modification. These results indicate that increasing O-GlcNAcylation with OGA inhibitors could be in general beneficial in diseases associated with protein aggregation.

There is also a large body of evidence indicating that increased levels of O-GlcNAc protein modification provides protection against pathogenic effects of stress in cardiac tissue, including stress caused by ischemia, hemorrhage, hypervolemic shock, and calcium paradox. For example, activation of the hexosamine biosynthetic pathway (HBP) by administration of glucosamine has been demonstrated to exert a protective effect in animal models of ischemia/reperfusion, trauma hemorrhage, hypervolemic shock and calcium paradox. Moreover, strong evidence indicates that these cardioprotective effects are mediated by elevated levels of protein O-GlcNAc modification. There is also evidence that the O-GlcNAc modification plays a role in a variety of neurodegenerative diseases, including Parkinson's disease and related synucleinopathies, and Huntington's disease.

Humans have three genes encoding enzymes that cleave terminal β-N-acetyl-glucosamine residues from glycoconjugates. The first of these encodes the enzyme O-glycoprotein-2-acetamido-2-deoxy-β-D-glucopyranosidase (O-GlcNAcase). O-GlcNAcase is a member of family 84 of glycoside hydrolases. O-GlcNAcase acts to hydrolyze O-GlcNAc off of serine and threonine residues of post-translationally modified proteins. Consistent with the presence of O-GlcNAc on many intracellular proteins, the enzyme O-GlcNAcase appears to have a role in the etiology of several diseases including type II diabetes, AD and cancer. Although O-GlcNAcase was likely isolated earlier on, about 20 years elapsed before its biochemical role in acting to cleave O-GlcNAc from serine and threonine residues of proteins was understood. More recently O-GlcNAcase has been cloned, partially characterized, and suggested to have additional activity as a histone acetyltra nsferase.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, existing compounds that act to block O-GlcNAcase function are non-specific and act potently to inhibit the lysosomal 1-hexosaminidases.

Low molecular weight OGA inhibitors are e.g. disclosed in the international applications WO 2008/025170 and WO 2014/032187, which are structurally different from the compounds of the present invention. Further compounds that have some structurally similar elements are disclosed in WO 2016/030443, U.S. Pat. Nos. 3,489,757, 3,299,067, WO 99/21850, WO 2005/110982 and WO 2009/053373. However, these compounds do not show the improved pharmacological properties more closely described below.

Presently, no OGA inhibitor has reached the market. Thus, there is a need for low molecular weight molecules that selectively inhibit OGA and provide improved pharmacological properties that are of high relevance in drug development.

The present invention has the object of providing novel compounds having valuable properties, in particular those which can be used for the preparation of medicaments.

In this regard, plasma protein binding (PPB) is an important differentiating factor in drug development as it determines at least in part the unbound, and thus, likely effective) drug concentrations at pharmacological target site. It is a well-acknowledged paradigm that, in the absence of energy-dependent processes (e.g. transporter-mediated active organ uptake or efflux), once steady state equilibrium has been reached, unbound drug concentration in plasma may be considered equal to unbound drug concentration in the target tissue(s), i.e. only the unbound drug in the tissues is available for binding to the target receptor and can therefore drive the desired pharmacologic activity (Free drug theory (FDT) (Bohnert, T. et al. J. Pharmaceutical Sciences 2013, 102, 2953-2994). As a consequence, high plasma protein binding may also have a negative impact on efficacy since it is the free fraction of drug that is responsible for the pharmacological action.

Plasma protein binding information can be used to estimate the unbound and thus effective concentration of drugs in order to establish pharmacokinetic/pharmacodynamic (PKPD) relationships in animals and humans. The extent of plasma protein binding across species provides important information for PKPD modelling and helps to better understand translational aspects and/or efficacy differences between animal models and humans.

In the present invention, the introduction of a sulfoximine group results in an increased unbound fraction (decreased PPB) for compounds of Formula (I). In addition, the preferred compounds of the invention provide a low variability of fractions unbound across several animal species including humans. As a consequence, free drug concentrations in tissues are increased, directly yielding higher unbound brain concentrations (as measured by cerebrospinal fluid concentrations as surrogate) with similar effects measurable across different species which often greatly improve predictability of human PK and result in lower effective human dose due to the same extent of increase of unbound fractions across species (Liu et al. J. Med. Chem. 2014, 57, 8238).

It has been surprisingly found that the compounds according to the invention and salts thereof have very valuable pharmacological properties. Due to the substitution at the dihydrobenzofurane ring system by R' and/or R", the compounds achieve increased metabolic stability, as e.g. shown in microsome stability assays as compared to their unsubstituted conterparts, without loosing their pharmaceutical potency.

Further, preferred glycosidase inhibitors of formula I provide increased unbound, i.e. free fractions in plasma. Moreover, the preferred compounds according to the invention and salts thereof consistently provide increased free fractions in plasma across species including humans (low inter-species variability), which make them ideal for pharmaceutical development and their application as a drug.

The invention relates to compounds of formula (I)

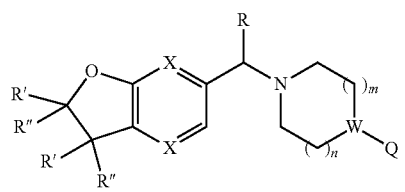

(I)

wherein
R is straight chain or branched alkyl having 1 to 6 carbon atoms, wherein 1 to 5 hydrogen atoms may be replaced by Hal or OH;
W is CH or N;
X is N or CR';
R', R" denote each independently H, Hal or straight chain or branched alkyl having 1 to 12 carbon atoms, wherein at least one of R and R" is different from H;
R'" denotes H, Hal, NR³R⁴, CHR³R⁴, OR³, CN or a straight chain or branched alkyl having 1 to 12 carbon atoms, wherein 1 to 3 CH₂-groups may be replaced by a group selected from O, NR³, S, SO, SO₂, S(O)(NR³'), N(SO)R³', CO, COO, OCO, CONR³, NR³CO,

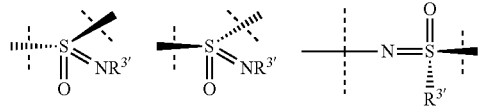

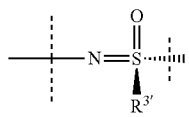

and wherein 1 to 5 hydrogen atoms may be replaced by Hal, NR³R⁴ or NO₂ or by one of the following groups:

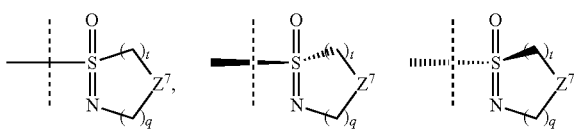

or R" denotes one of the following groups:

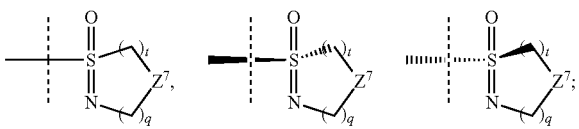

R³, R⁴ denote each independently H or a straight chain or branched alkyl group having 1 to 12 carbon atoms;
Q denotes one of the following groups:

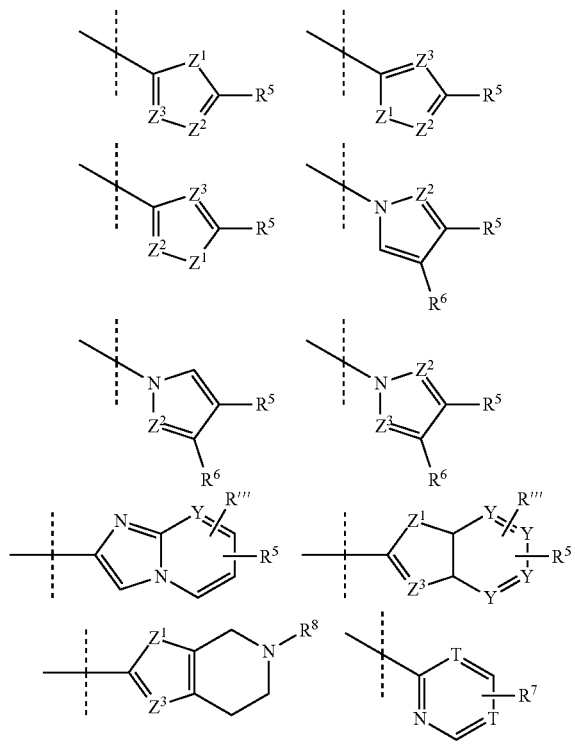

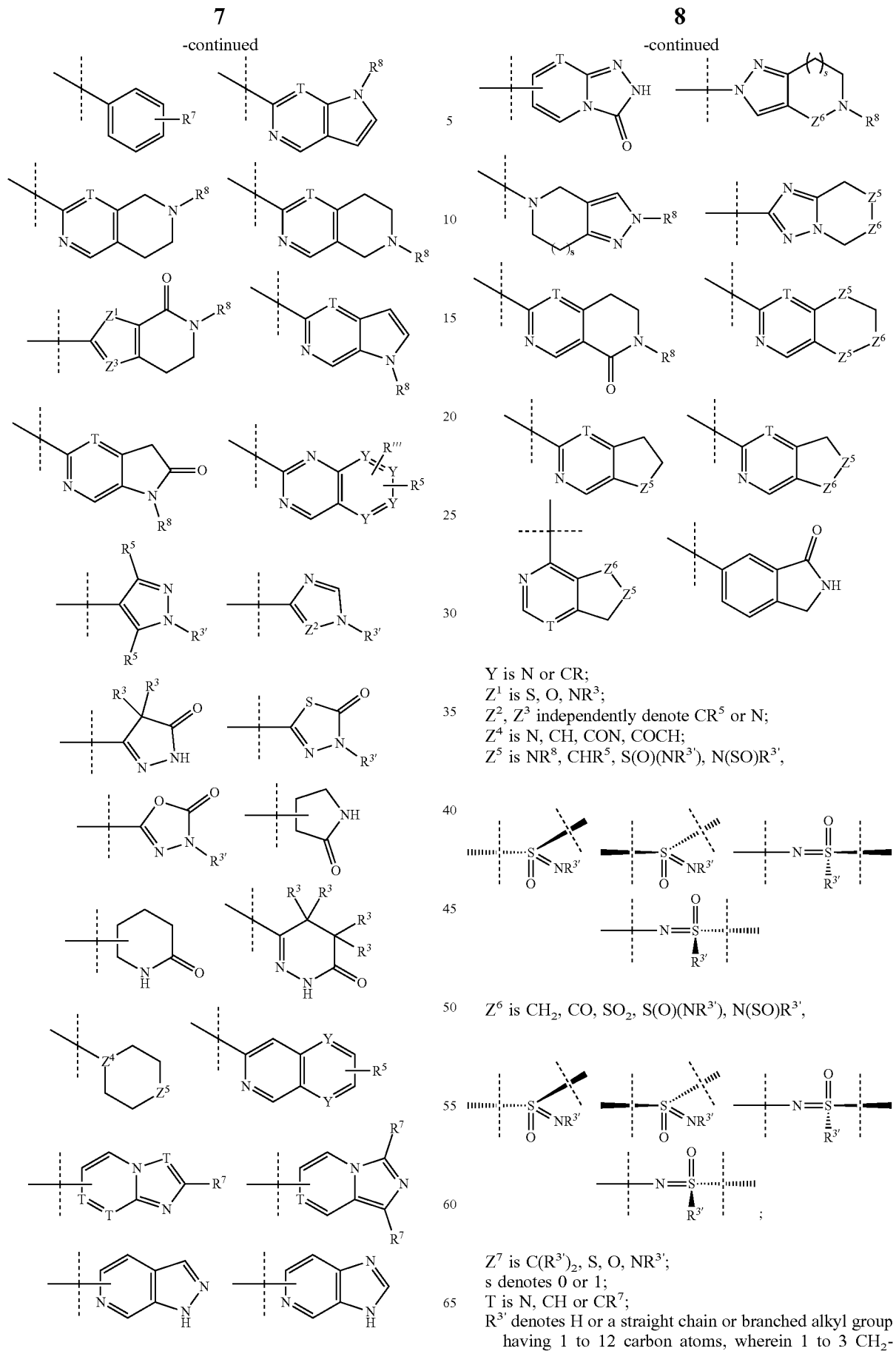
Y is N or CR;
$Z^1$ is S, O, $NR^3$;
$Z^2$, $Z^3$ independently denote $CR^5$ or N;
$Z^4$ is N, CH, CON, COCH;
$Z^5$ is $NR^8$, $CHR^5$, S(O)($NR^{3'}$), N(SO)$R^{3'}$,
$Z^6$ is $CH_2$, CO, $SO_2$, S(O)($NR^{3'}$), N(SO)$R^{3'}$,
$Z^7$ is C($R^{3'}$)$_2$, S, O, $NR^{3'}$;
s denotes 0 or 1;
T is N, CH or $CR^7$;
$R^{3'}$ denotes H or a straight chain or branched alkyl group having 1 to 12 carbon atoms, wherein 1 to 3 CH$_2$- groups may be replaced by a group selected from SO$_2$, CO, O and wherein 1 to 5 hydrogen atoms may be replaced by Hal;

R$^5$, R$^6$, R$^7$ independently denote H, Hal, NR$^3$R$^4$, NO$_2$ or a straight chain or branched alkyl having 1 to 12 carbon atoms, wherein 1 to 3 CH$_2$-groups may be replaced by a group selected from O, NR$^3$, S, SO, SO$_2$, S(O)(NR$^{3'}$), N(SO)R$^{3'}$, CO, COO, OCO, CONR$^3$, NR$^3$CO

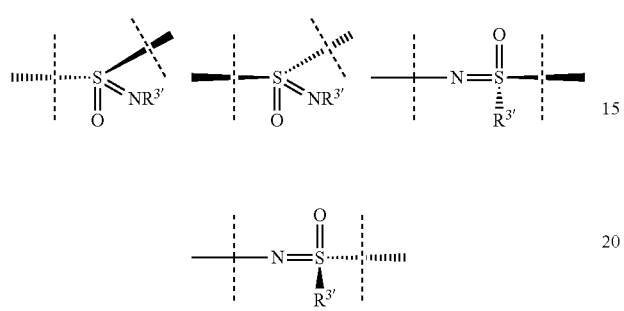

and wherein 1 to 5 hydrogen atoms may be replaced by Hal, NR$^3$R$^4$, NO$_2$, OR$^3$, Het, Ar, Cyc, or by one of the following groups:

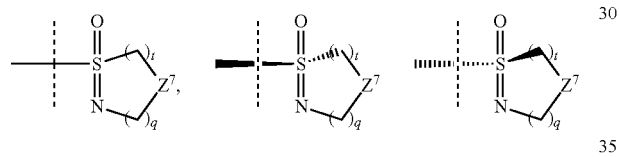

or R$^5$, R$^6$, R$^7$ denote Ar, Het or Cyc or one of the following groups:

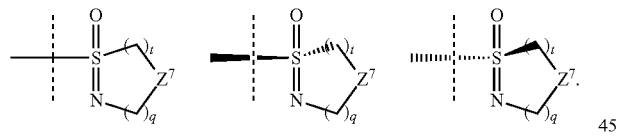

R$^8$ denotes H or straight chain or branched alkyl having 1 to 12 carbon atoms, wherein 1 to 3 CH$_2$-groups may be replaced by a group selected from SO, SO$_2$, S(O)(NR$^{3'}$), N(SO)R$^{3'}$, CO, COO, OCO, CONR$^3$, NR$^3$CO, and

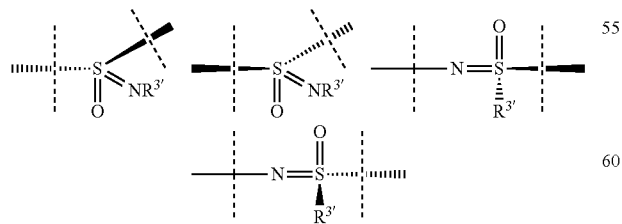

and further wherein 1 to 5 hydrogen atoms may be replaced by CN, OR$^3$, SR$^3$, Hal, NR$^3$R$^4$, NO$_2$ or by one of the following groups:

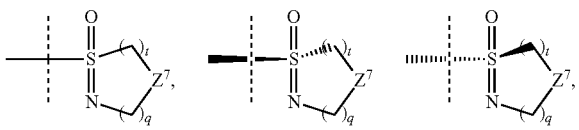

or R$^8$ denote one of the following groups:

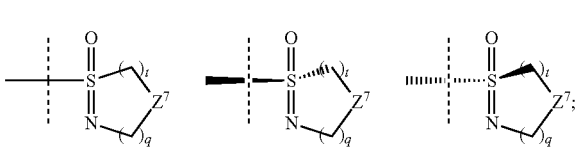

Hal denotes F, Cl, Br or I;

Het denotes a saturated, unsaturated or aromatic ring, being monocyclic or bicyclic or fused-bicyclic and having 3- to 8-members and containing 1 to 4 heteroatoms selected from N, O and S, which may be substituted by 1 to 3 substituents selected from R$^5$, Hal and OR$^3$;

Ar denotes a 6-membered carbocyclic aromatic ring or a fused or non-fused bicylic aromatic ring system, which is optionally substituted by 1 to 3 substituents independently selected from R$^5$, OR$^3$ and Hal;

Cyc denotes a saturated or an unsaturated carbocyclic ring having from 3 to 8 carbon atoms which is optionally substituted by 1 to 3 substituents independently selected from R$^5$ or Hal or OH;

m and n denote independently from one another 0, 1, 2 or 3, t and q denote independently from one another 0, 1, 2 or 3, with t+q>1;

and pharmaceutically usable derivatives, solvates, salts, prodrugs, tautomers, enantiomers, racemates and stereoisomers thereof, including mixtures thereof in all ratios and compounds of formula I, wherein one or more H atoms are replaced by D (deuterium).

Specifically, formula (I) includes the following two enantiomers of formula Ia and Ib:

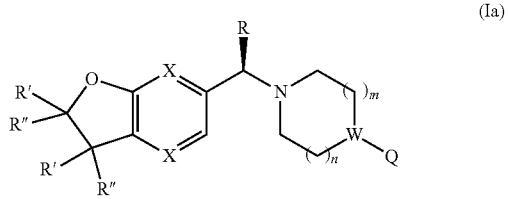
(Ia)

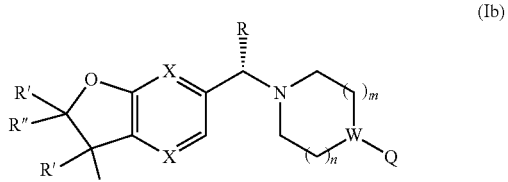
(Ib)

wherein R, R', R", X, W, Q, n and m have the meaning given above.

The invention also relates to a mixture of, i.e. a composition comprising, compounds Ia and Ib as set out above, having identical groups R, R', R", X, W, Q, n and m in equal or unequal amounts.

Throughout the specification, R in formula I, Ia and Ib is preferably methyl. The indices m and n in formula I, Ia, Ib and Ic are preferably simultaneously 1.

Compounds of formula Ic are most preferred:

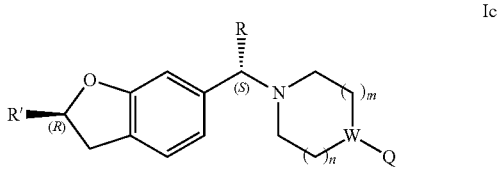

Ic wherein R, R', W, Q, n and m have the meaning given in above. In a very preferred embodiment, R and R' in formula Ic denote both methyl.

If individual groups and indices, such as R' and m, occur more than once in a compound of formula I, they can have the same or different meanings according to the respective definition of that group.

Preferred compounds of the present invention are preferably used as single isomer in their non-racemic form, i.e. as diasteromerically and enatiomerically pure compounds or their diastereomerically and enaniomerically enriched mixtures of the respective diastereomers and enantiomers. If R is an unsubstituted straight chain or branched alkyl having 1 to 6 carbon atoms, such as methyl, ethyl, n-propyl or iso-butyl, the S-configuration at this stereogenic center of compounds of formula I is preferred. Very preferred are formulae Ib and B.

A further preferred compound of formula I is a single enantiopure or enantiomerically enriched diastereoisomer, i.e. a compound wherein the stereogenic center bearing the group R has an S-configuration and any other stereogenic center within the compound has either an S- or an R-configuration.

In general, compounds of formula I are preferred that contain one ore more preferred groups such as R' and indices such as m or n. Compounds of formula I are the more preferred, the more preferred groups or indices they contain.

If substituents, such as the group $R^8$, are connected to the remainder of the molecule through a heteroatom, the connecting atom in the respective group is preferably a carbon atom, S-atom or the respective group is H.

The invention also relates to the use of compounds of formula (I) as a medicament.

In the meaning of the present invention, the compound is defined to include pharmaceutically usable derivatives, solvates, prodrugs, tautomers, enantiomers, racemates and stereoisomers thereof, including mixtures thereof in all ratios.

The term "pharmaceutically usable derivatives" is taken to mean, for example, the salts of the compounds according to the invention and also so-called prodrug compounds. The term "solvates" of the compounds is taken to mean adductions of inert solvent molecules onto the compounds, which are formed owing to their mutual attractive force. Solvates are, for example, mono- or dihydrates or alkoxides. The invention also comprises solvates of salts of the compounds according to the invention. The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention. It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in-vivo to provide the bioactive agent (i.e. compounds of the invention) is a prodrug within the scope and spirit of the invention. Various forms of prodrugs are well known in the art. It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as pure E or Z isomers, or in the form of mixtures of these double bond isomers. Where possible, the compounds of the invention may be in the form of the tautomers, such as keto-enol tautomers. All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or non-chiral phases or by re-crystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

An enantiomerically enriched mixture denotes a compound of Formula (I) or related formula having an enantiomeric excess, as measured by methods well known by one skilled in the art, of 10% or more, preferably 50% or more, and more preferably more than 95%. Most preferably an enantiomerically enriched mixture denotes a compound of Formula (I) or related Formulae having an enantiomeric excess of more than 98%.

The nomenclature as used herein for defining compounds, especially the compounds according to the invention, is in general based on the rules of the IUPAC-organization for chemical compounds and especially organic compounds. The compounds of invention have been named according to the standards used in the program AutoNom 2000 or ACD Lab Version 12.01 or Instant JChem Version: 15.12.7.0. The determination of the stereochemistry (S) or (R) is performed using standard rules of the nomenclature well known by one skilled in the art. The terms indicated for explanation of the above compounds of the invention always, unless indicated otherwise in the description or in the claims, have the following meanings:

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent the expression of such substituent may differ from each other (e.g. methyl and ethyl). It shall be understood accordingly that a multiple substitution by any radical of the invention may involve identical or different radicals. Hence, if individual radicals occur several times within a compound, the radicals can adopt any of the meanings indicated, independently of one another.

The term "alkyl" or "alkyl group" refers to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkanyls. Examples of suitable alkyl radicals are methyl, ethyl, n-propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl. In certain embodiments of the invention, 1 or more, preferable 1 to 3 $CH_2$ groups may be replaced by other divalent groups according to the definitions given above and below. In a particular embodiment, an H atom of alkyl may be replaced by Cyc.

In an embodiment of the invention, alkyl denotes unbranched or branched alkyl having 1-10 C atoms, in which 1-7 H atoms may be replaced independently from one another by Hal. A preferred embodiment of alkyl denotes unbranched or branched alkyl having 1-6 C atoms, in which 1-4 atoms may be replaced independently from one another by Hal. In a more preferred embodiment of the invention, alkyl denotes unbranched or branched alkyl having 1-4 C atoms, in which 1-3 H atoms can be replaced independently from one another by Hal, particularly by F and/or Cl. It is most preferred that alkly denotes unbranched or branched alkyl having 1-6 C atoms. Highly preferred is $C_{1-4}$-alkyl. A $C_{1-4}$-alkyl radical is for example a methyl, ethyl, propyl, isopropyl, butyl, isobutyl, tert-butyl, sec-butyl, tert-butyl, fluoromethyl, difluoromethyl, trifluoromethyl, pentafluoroethyl, 1,1,1-trifluoroethyl or bromomethyl, especially methyl, ethyl, propyl or trifluoromethyl. It shall be understood that the respective denotation of alkyl is independently of one another in any radical of the invention.

The terms "cycloalkyl" or "Cyc" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In an embodiment of the invention, Cyc denotes cycloalkyl having 3-7 C atoms, in which 1-4 H atoms may be replaced independently of one another by Hal. Preferred is $C_3$-$C_7$-cycloalkyl. More preferred is $C_4$-$C_7$-cycloalkyl. Most preferred is $C_5$-$C_7$-cycloalkyl, i.e. cyclopentyl, cyclohexyl or cycloheptyl, highly preferably cyclohexyl. It shall be understood that the respective denotation of Cyc is independently of one another in any radical of the invention.

The term "Ar", "aryl" or "carboaryl" for the purposes of this invention refers to a mono- or polycyclic aromatic hydrocarbon systems having 3 to 14, preferably 3-12, more preferably 4 to 12, most preferably 5 to 10, highly preferably 6 to 8 carbon atoms, which can be optionally substituted. The term "Ar" or "aryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the aryl radical. The bonding to the compounds of the general formula (I) can be effected via any possible ring member of the aryl radical. Examples of suited aryl radicals are phenyl, biphenyl, naphthyl, 1-naphthyl, 2-naphthyl and anthracenyl, but likewise indanyl, indenyl or 1,2,3,4-tetrahydronaphthyl. Preferred carboaryls of the invention are optionally substituted phenyl, naphthyl and biphenyl, more preferably optionally substituted monocylic carboaryl having 6-8 C atoms, most preferably optionally substituted phenyl.

Ar and aryl are preferably selected from the following group: phenyl, o-, m- or p-tolyl, o-, m- or p-ethylphenyl, o-, m- or p-propylphenyl, o-, m- or p-isopropylphenyl, o-, m- or p-tert.-butylphenyl, o-, m- or p-hydroxyphenyl, o-, m- or p-methoxyphenyl, o-, m- or p-ethoxyphenyl, o-, m- or p-fluoro-phenyl, o-, m- or p-bromophenyl, o-, m- or p-chlorophenyl, o-, m- or p-sulfonamidophenyl, o-, m- or p-(N-methyl-sulfonamido)phenyl, o-, m- or p-(N,N-dimethyl-sulfonamido)-phenyl, o-, m- or p-(N-ethyl-N-methyl-sulfonamido)phenyl, o-, m- or p-(N,N-diethyl-sulfonamido)-phenyl, particularly 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

Irrespective of further substitutions, Het denotes preferably 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazoM-, -4- or -5-yl, 1,2,4-triazo-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-iso-5indolyl, indazolyl, 1-, 2-, 4- or 5-benzimidazolyl, 1-, 3-, 4-, 5-, 6- or 7-benzo-pyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl, azabicyclo-[3.2.1]octyl or dibenzofuranyl.

The heterocyclic radicals may also be partially or fully hydrogenated.

Irrespective of further substitutions, Het can thus also denote, preferably, 2,3-dihydro-2-, -3-, -4- or -5-furyl, 2,5-dihydro-2-, -3-, -4- or 5-furyl, tetra-hydro-2- or -3-furyl, 1,3-dioxolan-4-yl, tetrahydro-2- or -3-thienyl, 2,3-di-hydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-(-2-, -3-, -4-, -5-, -6-, -7- or -8-quinolyl, 1,2,3,4-tetra-hydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydro-benzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1 H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2, 3-dihydrobenzimidazolyl.

Het preferably denotes piperidinyl, 4-hydroxypiperidinyl, piperazinyl, 4-methylpiperazinyl, pyrrolidinyl, morpholinyl, dihydro-pyrazolyl, dihydro-pyridyl, dihydropyranyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, quinolyl, isoquinolyl, benzimidazolyl, benzotriazolyl, indolyl, benzo-1,3-dioxolyl, 2,3-dihydro-benzo[1,4]dioxinyl, indazolyl or benzothiadiazolyl, each of which is unsubstituted or mono-, di- or trisubstituted.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro) or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. Halogen preferably means a fluorine, chlorine or bromine atom. Fluorine and chlorine are more preferred, particularly when the halogens are substituted on an alkyl (haloalkyl) or alkoxy group (e.g. $CF_3$ and $CF_3O$). It shall be understood that the respective denotation of Hal is independently of one another in any radical of the invention.

R is preferably straight chain alkyl having 1 to 4 carbon atoms, wherein 1 to 5 hydrogen atoms may be replaced by Hal or OH. More preferably R is methyl or ethyl, and most preferably methyl.

W is preferably N.

$R^{3'}$ denotes preferably H, methyl, ethyl, 2-hydroxyethyl or 2-methoxyethyl.

Preferably, the group $S(O)(NR^{3'})$ is selected from

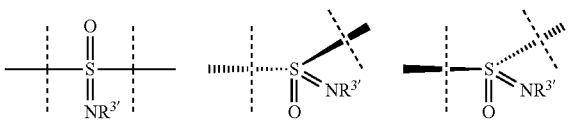

Preferably, the group $N(SO)R^{3'}$ is selected from

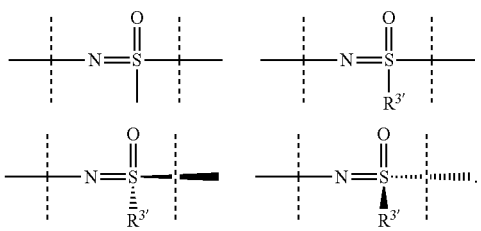

Q is preferably one of the following groups:

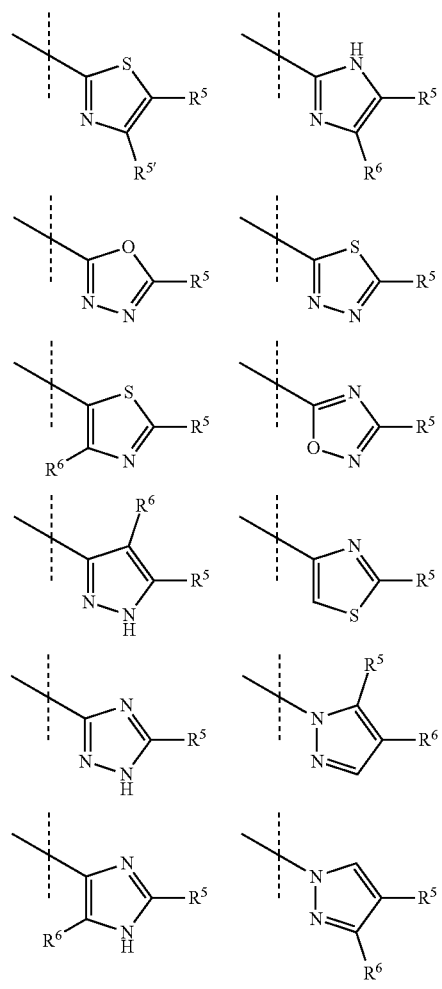

-continued
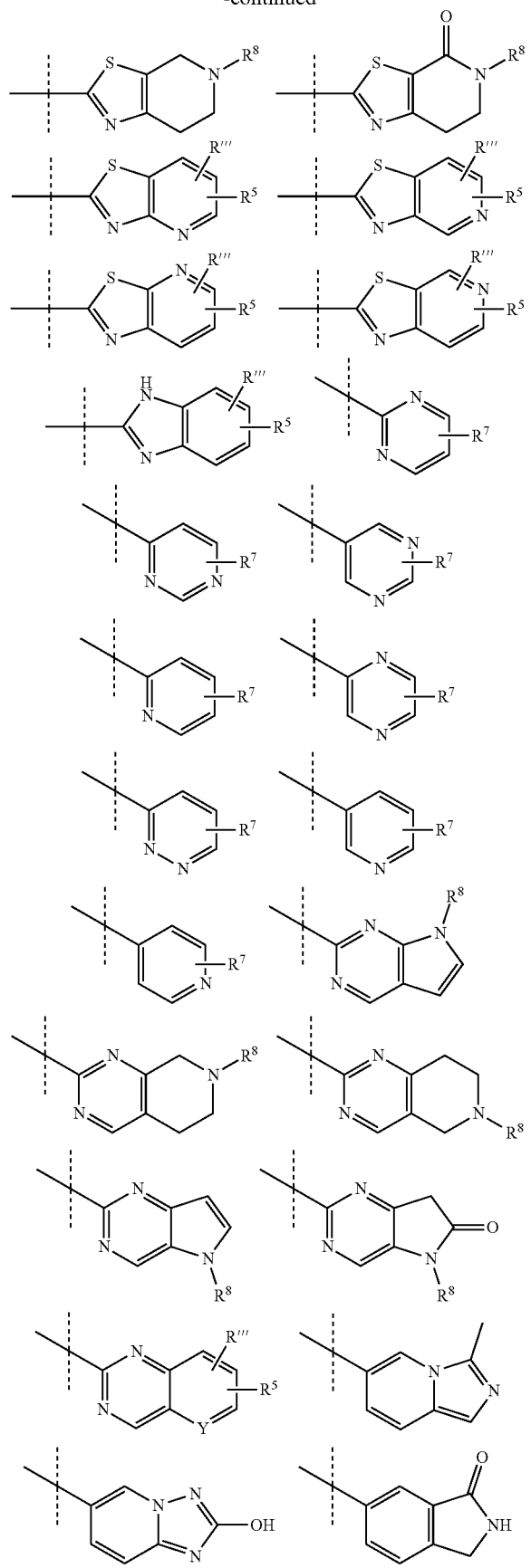
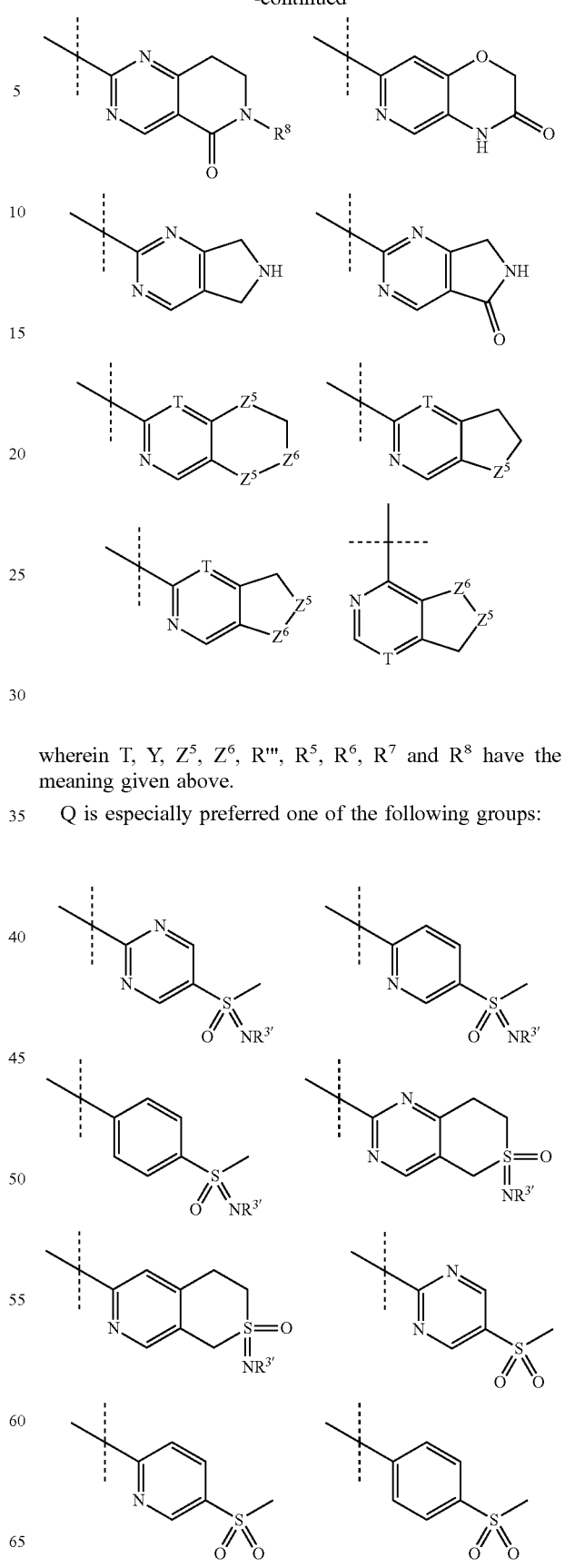
wherein T, Y, $Z^5$, $Z^6$, R''', $R^5$, $R^6$, $R^7$ and $R^8$ have the meaning given above.
Q is especially preferred one of the following groups:

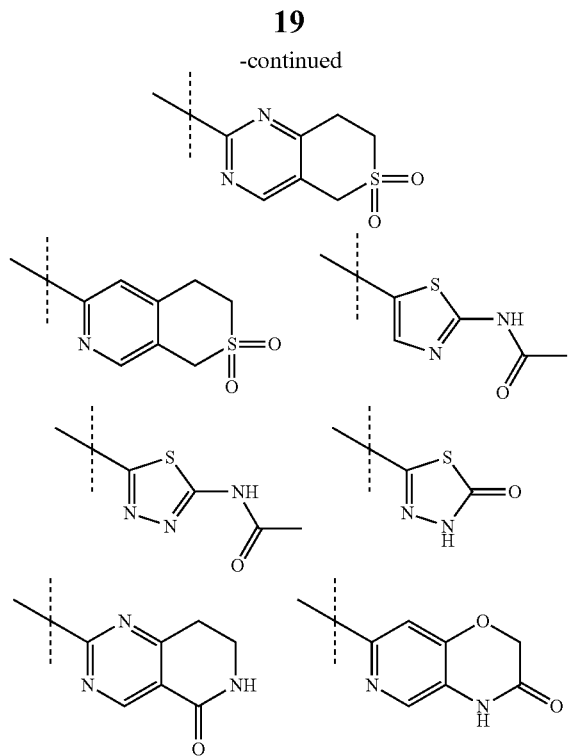

wherein R³' has the meaning given above and is preferably H, methyl, ethyl, 2-hydroxyethyl or 2-methoxyethyl.

R⁵, R⁶ and R⁷ are preferably independently H, SO₂CH₃, SO₂CH₂CH₃, SO₂CH₂CH₂OH, SO₂CH₂CH₂OCH₃, S(O)(NR³')CH₃, S(O)(NR³')CH₂CH₃, S(O)(NR³')CH₂CH₂OH, S(O)(NR³')CH₂CH₂OCH₃, N(SO)R³'CH₃, N(SO)R³'CH₂CH₃, N(SO)R³'CH₂CH₂OH, N(SO)R³'CH₂CH₂OCH₃,

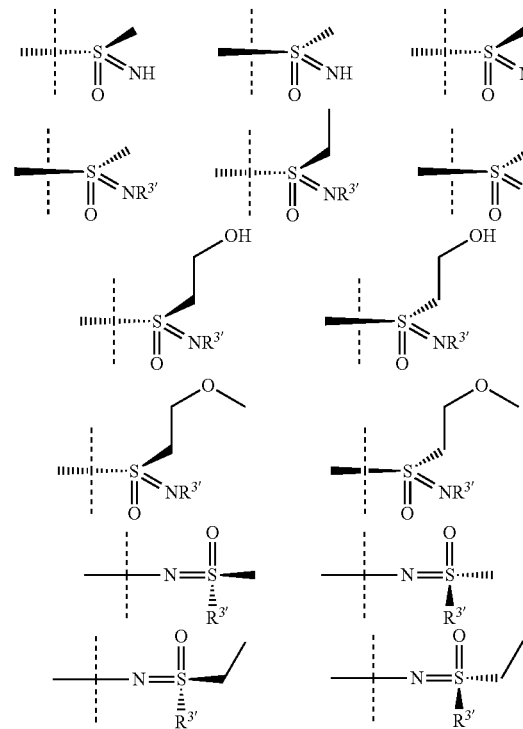

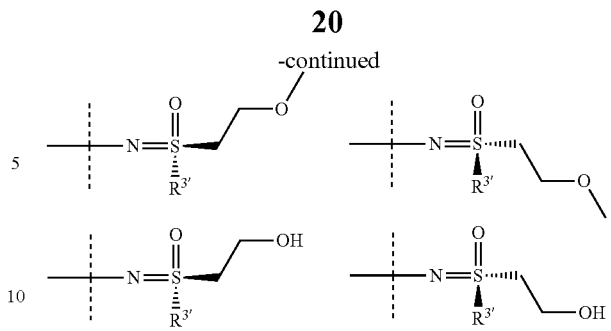

Hal, NR³R⁴, NO₂, phenyl, 2-, 3- or 4-hydroxy or methoxyphenyl, alkyl, preferably methyl, ethyl, isopropyl, isobutyl, tert-butyl, CF₃, alkoxy (Oalkyl), preferably methoxy or ethoxy, hydroxyalkylen, preferably CH₂OH, CH₂CH₂OH, alkoxyalkylen preferably CH₂CH₂OCH₃, COOH, COOalkyl, preferably COOCH₃, COOCH₂CH₃, CONHalkyl, preferably CONHCH₃, CONHCH₂CH₃, CONHisopropyl, CONHcyclohexyl, CONH₂, CON(CH₃)₂, NHCOalkyl, preferably NHCOCH₃, NHCOCH₂CH₃, NHCOPropyl, NHCOisopropyl, NHCOcyclopropyl, NHCO-4-Chloro-phenyl, NHCH₂CH₃, NHCH₂CH₂CH₃, NHCOCH₂CH₂OH, CO—N-morpholinyl, CON(CH₃) CH₂CH₂N(CH₃)₂, CO-1-piperidinyl, CO-4-hydroxy-1-piperidinyl, CO-1-piperazinyl, CO-4-methyl-1-piperazinyl, CH₂—N— morpholinyl, CH₂N(H)COCH₃, CH₂N(CH₃) COCH₃, CH₂NH₂, NH₂, CH(OH)CH₃, CH(OR³)CH₃ or a group selected from

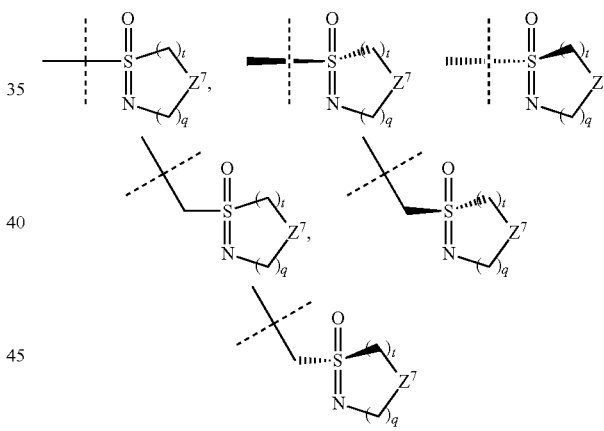

wherein t+q is 2 or 3.

R⁸ is preferably a group selected from H, COalkyl or alkyl or hydroxyl alkyl. More preferably, R⁸ is H, COmethyl or methyl.

T is preferably N or CH, most preferably N.

Z¹ is preferably S or NH.

Z², Z³ preferably denote independently CH or N.

Z⁴ is preferably N or CH.

Z⁵ is preferably is NR⁸, CHR⁵.

Z⁶ is preferably CH₂, CO or SO₂.

Z⁷ is preferably CH₂, S, O, NH. If Z⁷ is S, O, NR³', t and q are each 1 or one of t and q is 1 while the other denotes 2.

Most preferably, t and q simultaneously denote 1.

In a particularly preferred embodiment, compounds of formula Id are defined as given below:

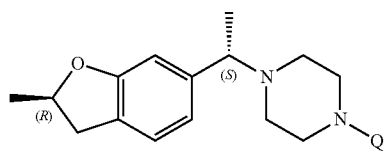

(Id)

Wherein Q has the meaning given above, and pharmaceutically usable derivatives, solvates, salts, prodrugs, tautomers, enantiomers, racemates and stereoisomers thereof, including mixtures thereof in all ratios and compounds of formula I, wherein one or more H atoms are replaced by D (deuterium).

Throughout the specification and claims, the individual groups such as COO, CONR³ can be attached through any of the linking atoms to the rest of the compound of formula I, i.e. a respective part of the compound of formula I may be attached to the right or left or lower or upper side of the individual group as presented in the specification.

Accordingly, the subject-matter of the invention relates to compounds of formula (I) as medicament, in which at least one of the aforementioned radicals has any meaning, particularly realize any preferred embodiment, as described above. Radicals, which are not explicitly specified in the context of any embodiment of formula (I), sub-formulae thereof or other radicals thereto, shall be construed to represent any respective denotations according to formula (I) as disclosed hereunder for solving the problem of the invention. That means that the aforementioned radicals may adopt all designated meanings as each described in the prior or following course of the present specification, irrespective of the context to be found, including, but not limited to, any preferred embodiments. It shall be particularly understood that any embodiment of a certain radical can be combined with any embodiment of one or more other radicals.

Particularly highly preferred embodiments are those compounds of formula (I) listed in Table 1 and/or physiologically acceptable salts thereof.

TABLE 1

Compounds of formulae (I). OGA enzyme inhibition assay:

| No | Structure | Configuration specification | OGA IC50 (M) |
|----|-----------|----------------------------|--------------|
| 1  | 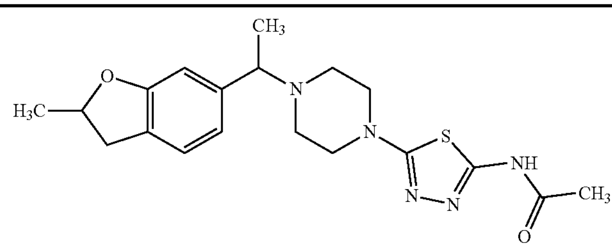          | Racemic                    | ++++         |
| 2  | 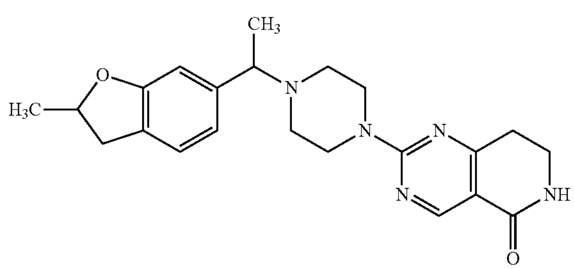 [SMILES: CC1Cc2ccc(C(C)N3CCN(c4ncc5c(n4)CCNC5=O)CC3)cc2O1]          | Racemic                    | ++++         |
| 3  | 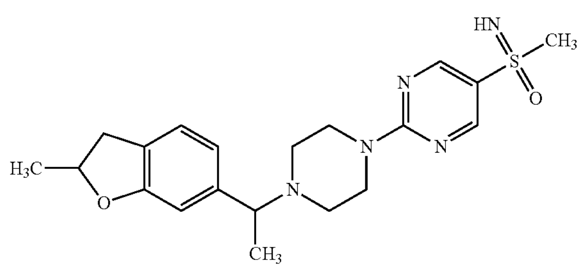          | Racemic                    | ++++         |
| 4  | 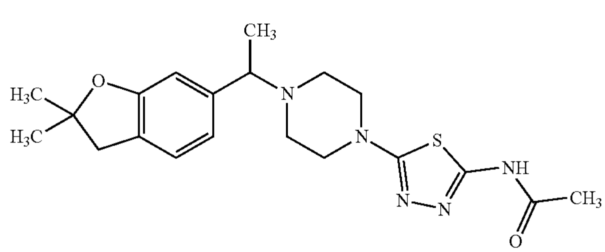 [SMILES: CC(=O)Nc1nnc(N2CCN(C(C)c3ccc4c(c3)OC(C)(C)C4)CC2)s1]          | Racemic                    | +            |

TABLE 1-continued

Compounds of formulae (I). OGA enzyme inhibition assay:

| No | Structure | Configuration specification | OGA IC50 (M) |
|---|---|---|---|
| 5 | (structure) | Racemic | + |
| 6 | (structure) | Racemic | + |
| 7 | (structure) | Racemic | +++ |
| 8 | (structure) | Racemic | ++ |
| 9 | (structure) | Synthesized from (R)-propane-1,2-diol | ++++ |

TABLE 1-continued

Compounds of formulae (I). OGA enzyme inhibition assay:

| No | Structure | Configuration specification | OGA IC50 (M) |
|---|---|---|---|
| 10 | 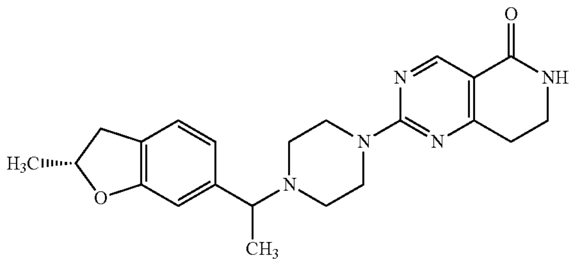 [SMILES: CC(c1ccc2c(c1)O[C@H](C)C2)N1CCN(c2ncc3c(n2)CCNC3=O)CC1] | Synthesized from (R)-propane-1,2-diol | ++++ |
| 11 | 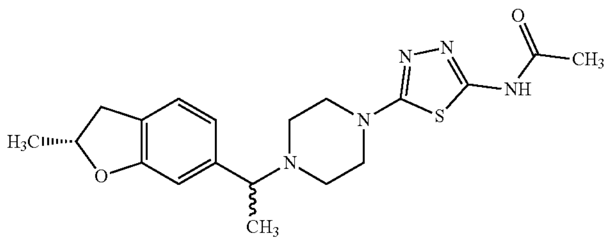 [SMILES: CC(=O)Nc1nnc(N2CCN(C(C)c3ccc4c(c3)O[C@H](C)C4)CC2)s1] | Chiral SFC Method A: 1st eluting compound | ++ |
| 12 | 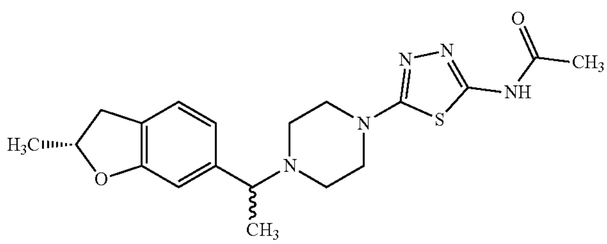 [SMILES: CC(=O)Nc1nnc(N2CCN(C(C)c3ccc4c(c3)O[C@H](C)C4)CC2)s1] | Chiral SFC Method A: 2nd eluting compound | ++++ |
| 13 | 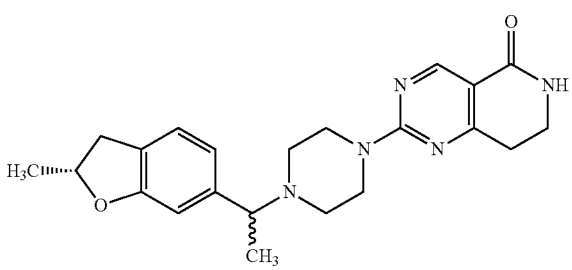 [SMILES: CC(c1ccc2c(c1)O[C@H](C)C2)N1CCN(c2ncc3c(n2)CCNC3=O)CC1] | Chiral SFC Method A: 1st eluting compound | ++++ |
| 14 | 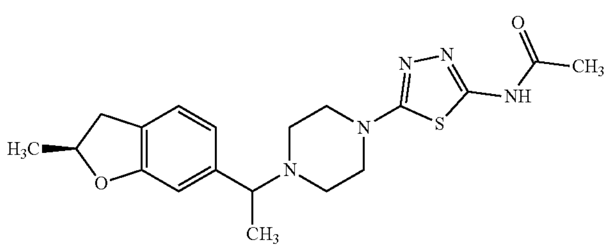 [SMILES: CC(=O)Nc1nnc(N2CCN(C(C)c3ccc4c(c3)O[C@@H](C)C4)CC2)s1] | Synthesized from (S)-propane-1,2-diol | ++ |
| 15 | 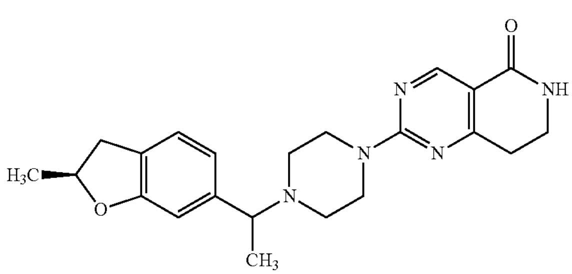 [SMILES: CC(c1ccc2c(c1)O[C@@H](C)C2)N1CCN(c2ncc3c(n2)CCNC3=O)CC1] | Synthesized from (S)-propane-1,2-diol | ++ |

TABLE 1-continued

Compounds of formulae (I). OGA enzyme inhibition assay:

| No | Structure | Configuration specification | OGA IC50 (M) |
|----|-----------|-----------------------------|--------------|
| 16 | 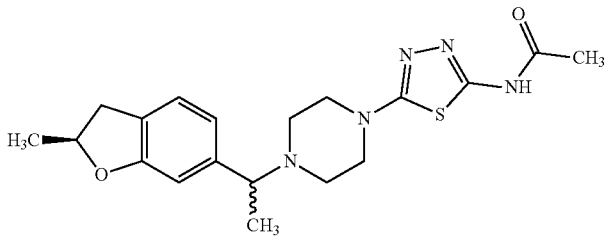 [SMILES: CC(=O)Nc1nnc(N2CCN(C(C)c3ccc4c(c3)O[C@@H](C)C4)CC2)s1] | Chiral SFC Method B: 1st eluting compound | ++ |
| 17 | 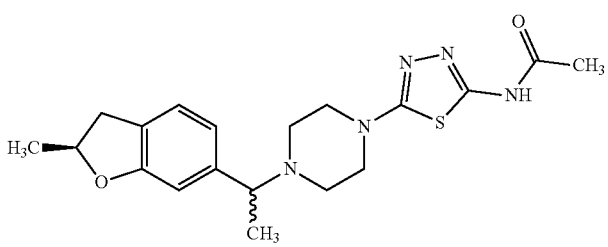 [SMILES: CC(=O)Nc1nnc(N2CCN(C(C)c3ccc4c(c3)O[C@@H](C)C4)CC2)s1] | Chiral SFC Method B: 2nd eluting compound | +++ |
| 18 | 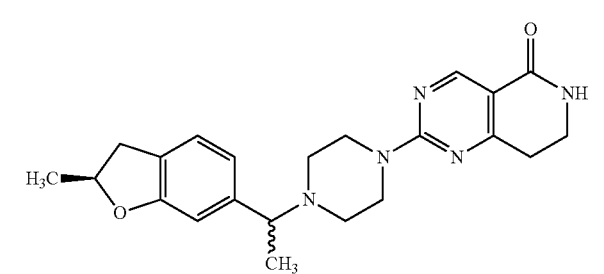 [SMILES: CC(c1ccc2c(c1)O[C@@H](C)C2)N1CCN(c2ncc3c(n2)CCNC3=O)CC1] | Chiral SFC Method C: 1st eluting compound | +++ |
| 19 | 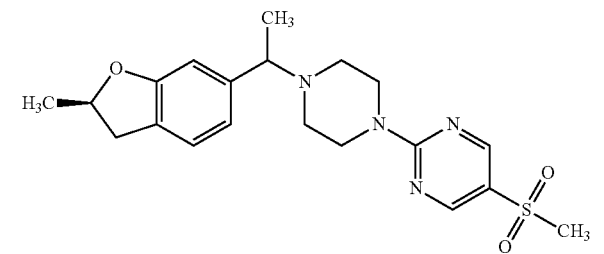 | Synthesized from (R)-propane-1,2-diol | ++++ |
| 20 | 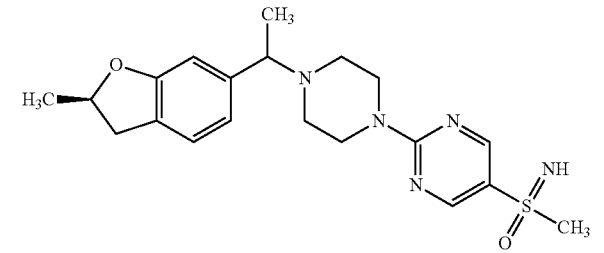 | Synthesized from (R)-propane-1,2-diol | ++++ |
| 21 | 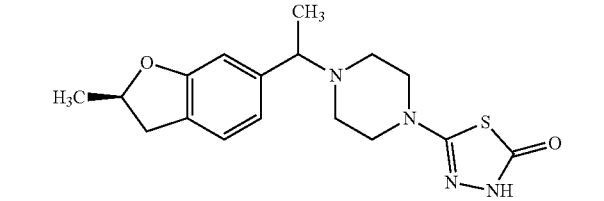 [SMILES: CC(c1ccc2c(c1)O[C@H](C)C2)N1CCN(c2n[nH]c(=O)s2)CC1] | Synthesized from (R)-propane-1,2-diol | +++ |

Activity range of the compounds of Formula (I) is the following:

| | |
|---|---|
| + | 1 to 10 µM |
| ++ | 0.2 to 1 µM |
| +++ | 0.2 to 0.05 µM |
| ++++ | below 0.05 µM |

Preferred compounds of the present invention demonstrate adequate properties for use as a drug. In particular, such preferred compounds show a high solid state stability, high stability in the presence of liver microsome, high oxidation stability and suitable permeability. Further preferred compounds of the present invention demonstrate their suitability as drugs by potent biological activity, such as the level of O-GlcNAcylation of total proteins measured in brain extracts. Relevant tests for determining such parameters are known by the person skilled in the art, e.g. solid state stability (Waterman K. C. (2007) *Pharm Res* 24(4); 780-790), stability in the presence of liver microsome (Obach R. S. (1999) *Drug Metab Dispos* 27(11); 1350-135) and the permeability (e.g. Caco-2 permeability assay, Calcagno A. M. (2006) *Mol Pharm* 3(1); 87-93); alternatively, they are described in Examples below, such as Example B02 describing the determination of O-GlcNAcylation level of total proteins measured in brain extracts. Compounds of the present invention that show a high potency in OGA inhibition assays and one or more of the above properties are especially suitable as a drug for the indications mentioned in the present specification.

The compounds according to formula (I) and the starting materials for its preparation, respectively, are produced by methods known per se, as described in the literature, i.e. under reaction conditions that are known and suitable for said reactions.

Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The following abbreviations refer respectively to the definitions below:

Ac (acetyl), aq (aqueous), h (hour), g (gram), L (liter), mg (milligram), MHz (Megahertz), µM (micromolar), min (minute), mm (millimeter), mmol (millimole), mM (millimolar), m.p. (melting point), equiv (equivalent), mL (milliliter), µL (microliter), ACN (acetonitrile), AcOH (acetic acid), BINAP (2,2'-bis(disphenylphosphino)-1,1'-binaphthalene, BOC (tert-butoxy-carbonyl), CBZ (carbobenzoxy), CDCl$_3$ (deuterated chloroform), CD$_3$OD (deuterated methanol), CH$_3$CN (acetonitrile), c-hex (cyclohexane), DCC (dicyclohexyl carbodiimide), DCM (dichloromethane), DHP (O-(2,4-dinitrophenyl)-hydroxylamine), dppf (1,1'-bis(diphenylphosphino)ferrocene), DIC (diisopropyl carbodiimide), DIEA (diisopropylethyl-amine), DMF (dimethylformamide), DMSO (dimethylsulfoxide), DMSO-d$_6$ (deuterated dimethylsulfoxide), EDC (1-(3-dimethyl-amino-propyl)-3-ethylcarbodiimide), ESI (Electro-spray ionization), EtOAc (Ethyl acetate), Et$_2$O (diethyl ether), EtOH (ethanol), FMOC (fluorenylmethyloxycarbonyl), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), K$_2$CO$_3$ (potassium carbonate), LC (Liquid Chromatography), m-CPBA (3-chloroperbenzoic acid), MD Autoprep (Mass directed Autoprep), MeOH (methanol), MgSO$_4$ (magnesium sulfate), MS (mass spectrometry), MTBE (Methyl tert-butyl ether), Mtr. (4-Methoxy-2,3,6-trimethylbenzen-sulfonyl), MW (microwave), NBS (N-bromo succinimide), NaHCO$_3$ (sodium bicarbonate), NaBH$_4$ (sodium borohydride), NMM (N-methyl morpholine), NMR (Nuclear Magnetic Resonance), MSH (O-mesitylenesulfonylhydroxylamine), POA (phenoxyacetate), Py (pyridine), PyBOP® (benzotriazole-1-yl-oxy-tris-pyrrolidino-phosphonium hexafluorophosphate), RT (room temperature), Rt (retention time), SFC (supercritical fluid chromatography), SPE (solid phase extraction), T3P (propylphosphonic anhydride), TBAF (tetra-n-butylammonium fluoride), TBTU (2-(1-H-benzotriazole-1-yl)-1,1,3,3-tetramethyluromium tetrafluoroborate), TEA (triethylamine), TFA (trifluoroacetic acid), THF (tetrahydrofurane), TLC (Thin Layer Chromatography), UV (Ultraviolet).

In general, the compounds according to Formula (I) and related formulae of this invention may be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those having ordinary skill in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by a person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

A "leaving group" LG denotes a chemical moiety which can be removed or replaced by another chemical group. Throughout the specification, the term leaving group preferably denotes Cl, Br, I or a reactively modified OH group, such as, for example, an activated ester, an imidazolide or alkylsulfonyloxy having 1 to 6 carbon atoms (preferably methylsulfonyloxy or trifluoromethylsulfonyloxy) or arylsulfonyloxy having 6 to 10 carbon atoms (preferably phenyl- or p-tolylsulfonyloxy). When a leaving group LG is attached to an aromatic or heteroaromatic ring, LG can denote in addition SO$_2$-alkyl or F. Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example through addition of HOBt, N-hydroxysuccinimide or HATU.

Depending on the nature of R', R", X, R, W, Q, m and n, different synthetic strategies may be selected for the synthesis of compounds of Formula (I). In the process illustrated in the following schemes, R', R", X, R, W, Q, m and n are as above-defined in the description unless otherwise mentioned.

Compounds of Formula (I), wherein R', R", X, R, W, Q, m and n are defined as above, can be prepared from alternative compounds of Formula (I), using suitable interconversion procedures such as those described hereinafter in the examples, or conventional interconversion procedures well known by one skilled in the art.

Compound of formula (I) can be separated into compounds of formula (Ia) and (Ib) by chiral chromatography or by chiral resolution, re-crystallization with use of an optically active acid, using methods known by one skilled in the art and as described below in the examples (Scheme 1).

Scheme 2

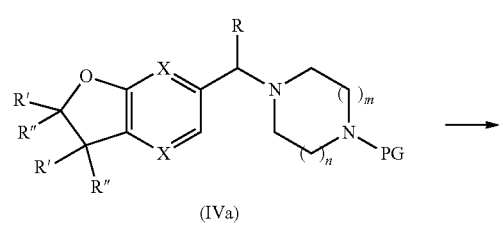

(IVa)

Scheme 1

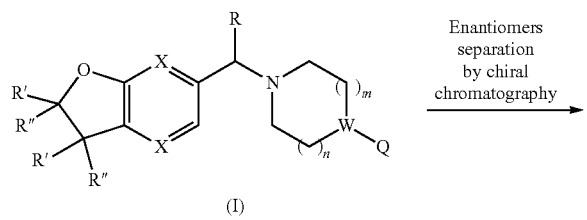

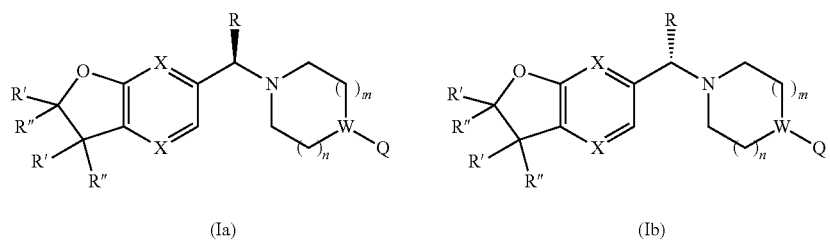

Compounds of formula (Ic), wherein R', R", X, R, Q, m and n are defined as above and W=N, can be prepared by the addition of an amine of formula (II) to a heterocycle of formula (III), where LG is a leaving group as defined above. This addition can be performed under thermic conditions, heating both compounds at a temperature between 50° C. and 200° C., using regular heating or microwave irradiation, in the presence of a base, such as but not limited to TEA, DIEA, $K_2CO_3$ or $Cs_2CO_3$, in a polar solvent, e.g. DMF, DMA or NMP. Alternatively, this addition can be catalysed by a metal complex, such as but not limited to $PdCl_2$, $Pd(OAc)_2$, $Pd_2(dba)_3$ in the presence of a ligand, e.g. BINAP, o-Tol$_3$P, X-Phos, and a base, e.g. NaOtBu, $Cs_2CO_3$ or $K_2CO_3$, in a suitable solvent or solvent mixture, for example dioxane, Toluene/MeOH, at a temperature between RT to 150° C., preferably at RT, for a few hours, e.g. one hour to 24 h (Scheme 2). Amine of formula (II) is obtained after deprotection of compound (IVa). PG is a suitable protecting group, which is compatible with the chemistry described below, such as but not limited to BOC. It can be removed under acidic conditions, such as but not limited to HCl in MeOH or dioxane or TFA in DCM, yielding isolation of amine (II).

Compounds of formula (Id), wherein R', R", X, R, Q, m and n are defined as above and W=CH, can be prepared from an ester (IVb) using method known by a person killed in the art and as described in the examples below. Different heterocycles Q can be prepared from ester functionality, such as but not limited to oxadiazole, thiadiazole and thiazole, (Jakopin, Z. et al. *Curr. Org. Chem.* 2008, 12, 850-898. Hemming, K. *Science of Synthesis*, 2004, 13, 127-184. Augustine, J. K. et al. *Tetrahedron*, 2009, 65, 9989-9996. 37. Kempson, J. *Name Reactions in Heterocyclic Chemistry II* (2011), 299-308). Depending on the nature of Q, compound of formula (Id) can be obtained from compound (IVc) by displacement of the leaving group LG, as defined above, in the presence of a base such as but not limited to Cs$_2$CO$_3$ in a polar solvent, e.g. DMF, DMSO or NMP (Scheme 3). Alternatively compound of formula (Id) can be prepared by metal catalysed cross coupling reaction with a suitable boronic acid (Va) or ester (Vb) and an heterocycle of formula (III), using conditions known by a person skilled in the art, such as but not limited to Pd(PPh$_3$)$_4$ as catalyst, K$_2$CO$_3$ as base, dioxane as solvent at temperature ranging from RT to 180° C. (Scheme 3). Hydrogenation of the resulting coupling product in the presence of a catalyst such as Pd(OH)$_2$, would yield compound of formula (Id) (e.g. Andres, J.-I. et al. *J. Med. Chem.* 2012, 55, 8685-8699) (Scheme 3).

Compound of formula (IV), wherein R', R", X, R, W, m and n are defined as above and Y$^1$ is a protecting group PG when W=N or an ester when W=CH, can be prepared from the corresponding ketone (IX) by reductive amination with amine (VI), using conditions known to the one skilled in the art, such as but not limited to the use of NaBH(OAc)$_3$ as reducing agent, in the presence of one equivalent of AcOH in DCE. Alternatively, reductive amination can be performed in two steps, with first imine formation, that can be catalysed by Ti(OiPr)$_4$, followed by reduction with suitable reducing agent, such as but not limited to NaBH$_4$ in MeOH (Abdel-Magid, A. F. at al. *J. Org. Chem.* 1996, 61, 3849-3862). Alternatively, ketone (IX) can be reduced into the corresponding alcohol (VIII) using usual reductive agents such as NaBH$_4$ in an alcoholic solvent, such as MeOH. Alcohol functionality can be then transformed into a suitable leaving group, such as but not limited to Cl or OMs, using conditions known to a person skilled in the art. The addition of amine (VI) to intermediate (VII) would yield the formation of compound (IV).

Scheme 3

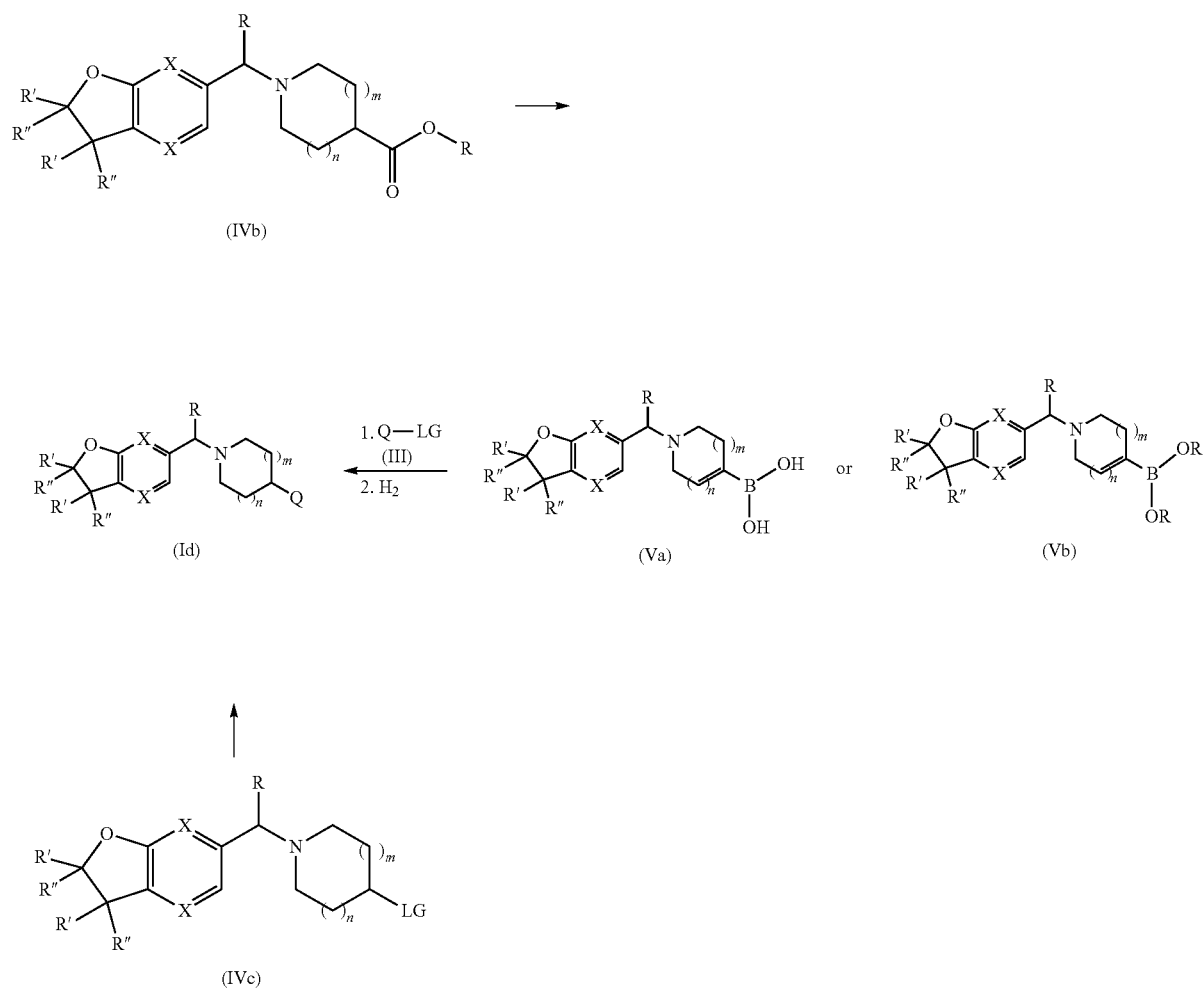

Scheme 4

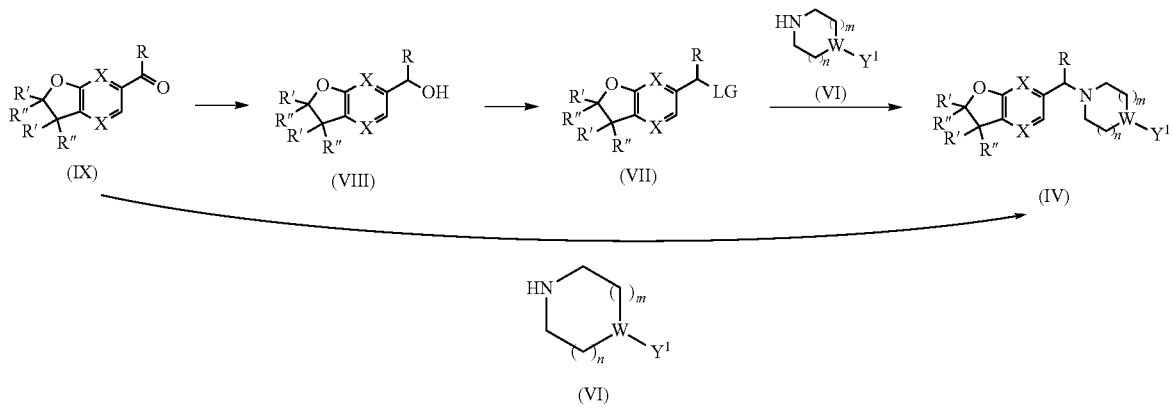

Alternatively, compound of formula (X), wherein W, Q, m and n are defined as above and PG is a suitable protecting group, such as but not limited to BOC, can be prepared from amine (XI), from compounds (XII), wherein m, n and PG are defined as above and $Y^2$ is an ester or a leaving group, or from compounds (XIIIa) or (XIIIb) (Scheme 5).

When W is N, compound of formula (X) can be prepared by the addition of an amine of formula (XI) to a heterocycle of formula (III), where LG is a leaving group as defined above. This addition can be performed under thermic conditions or can be catalysed by a metal complex, using conditions known by a person skilled in the art and as described below in the examples.

When W is CH, compound of formula (X) can be prepared from an ester (XII), wherein $Y^2$=COOR and W=CH, using method known by a person skilled in the art and as described in the examples below. Different heterocycles Q can be prepared from ester functionality, such as but not limited to oxadiazole, thiadiazole and thiazole, (Jakopin, Z. et al. *Curr. Org. Chem.* 2008, 12, 850-898. Hemming, K. *Science of Synthesis,* 2004, 13, 127-184. Augustine, J. K. et al. *Tetrahedron,* 2009, 65, 9989-9996. 37. Kempson, J. *Name Reactions in Heterocyclic Chemistry II* (2011), 299-308). Depending on the nature of Q, compound of formula (X) can be obtained from compound (XII), wherein W is CH and $Y^2$=LG as defined above, by displacement of the leaving group LG in the presence of a base such as but not limited to $Cs_2CO_3$ in a polar solvent, e.g. DMF, DMSO or NMP. Compound of formula (X), wherein Q is a thiazole, can be obtained from compound (XII), wherein $Y^2$ is an aminomethanecarbothioyl group, and a suitable alpha-bromo ketone, using conditions know by a person skilled in the art.

Alternatively, compound of formula (X) can be prepared by metal catalysed cross coupling reaction with a suitable boronic acid (XIIIa) or ester (XIIIb), and a heterocycle of formula (III), using conditions known by a person skilled in the art, such as but not limited to $Pd(PPh_3)_4$ as catalyst, $K_2CO_3$ as base, dioxane as solvent at temperature ranging from RT to 180° C. (Scheme 5). Hydrogenation of the resulting coupling product in the presence of a catalyst such as $Pd(OH)_2$, would yield compound of formula (X) (e.g. Andres, J.-I. et al. *J. Med. Chem.* 2012, 55, 8685-8699) (Scheme 5).

PG is a suitable protecting group, which is compatible with the chemistry described above, such as but not limited to BOC. It can be removed under acidic conditions, such as but not limited to HCl in MeOH or dioxane or TFA in DCM, yielding isolation of amine (XIV). It can be further transformed into compound of formula (I) by reductive alkylation with ketone of formula (IX), following conditions well known by a person skilled in the art, as described in the examples (Abdel-Magid, A. F. at al. *J. Org. Chem.* 1996, 61, 3849-3862). Alternatively, amine (XIV) addition to compound (VII), prepared as described above and in the examples, would yield the formation of compound of formula (I).

Scheme 5

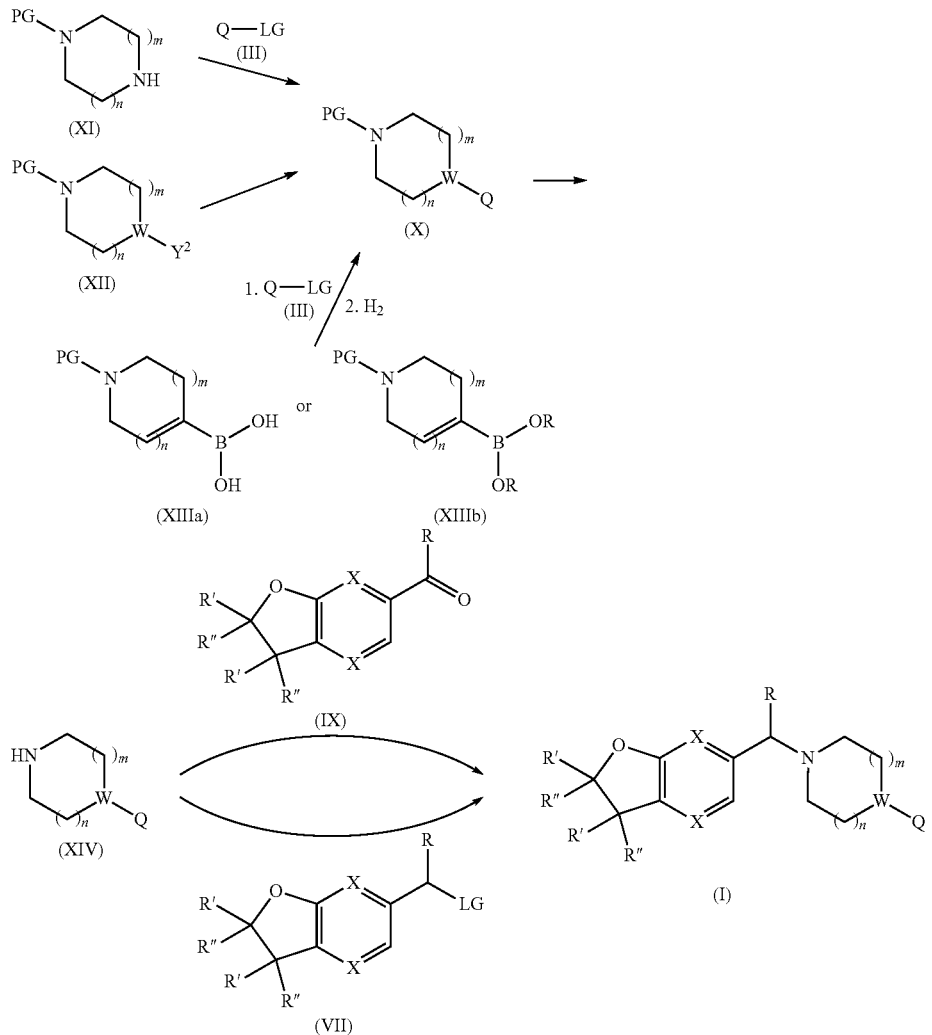

Amine of formula (II) can be separated into amines of formula (IIa) and (IIb) by chiral chromatography or chiral resolution by re-crystallization with an optically active acid, using methods known by one skilled in the art and as described below in the examples (Scheme 6).

Scheme 6

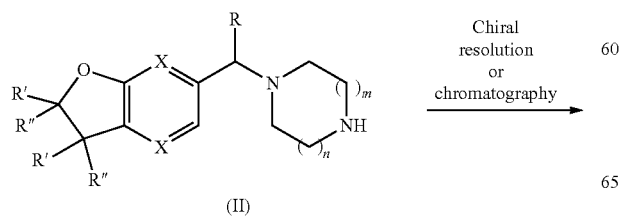

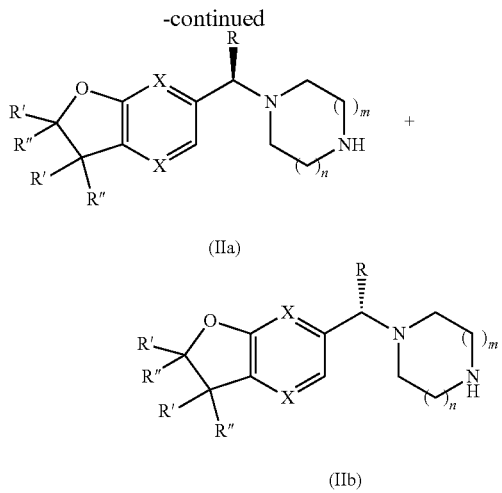

Alternatively, amines of formula (IIa) and (IIb) can be synthesized from chiral amines (XVIa) and (XVIb) respectively, wherein R', R", X, R are defined as above. Addition of amines (XVIa) and (XVIb) to reagent (XV), wherein PG is a protecting group, e.g. BOC or SO$_2$Tol and LG is a leaving group, e.g. Cl, would yield the formation of protected amines (IVe) and (IVf) respectively (Thiel, O. R. et al. *J. Org. Chem.* 2008, 73, 3508-3515). Deprotection conditions need to be selected based on the nature of the PG, such as HCl in dioxane or MeOH or TFA in DCM for BOC protecting group. Alternatively a mixture of HBr, AcOH and 4-hydroxybenzoic acid or a mixture of H$_2$SO$_4$ and trifluoroacetic acid at temperatures ranging from RT to 100° C. would be used to cleave a sulfonamide protecting group, such as para-toluene sulfonamide.

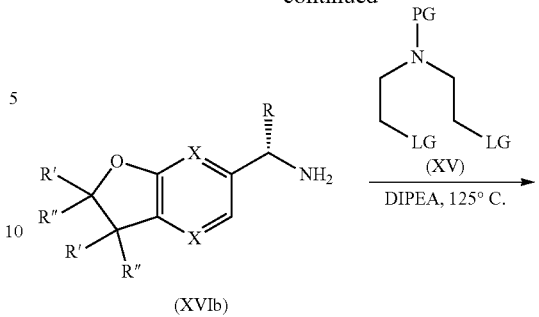

Scheme 7

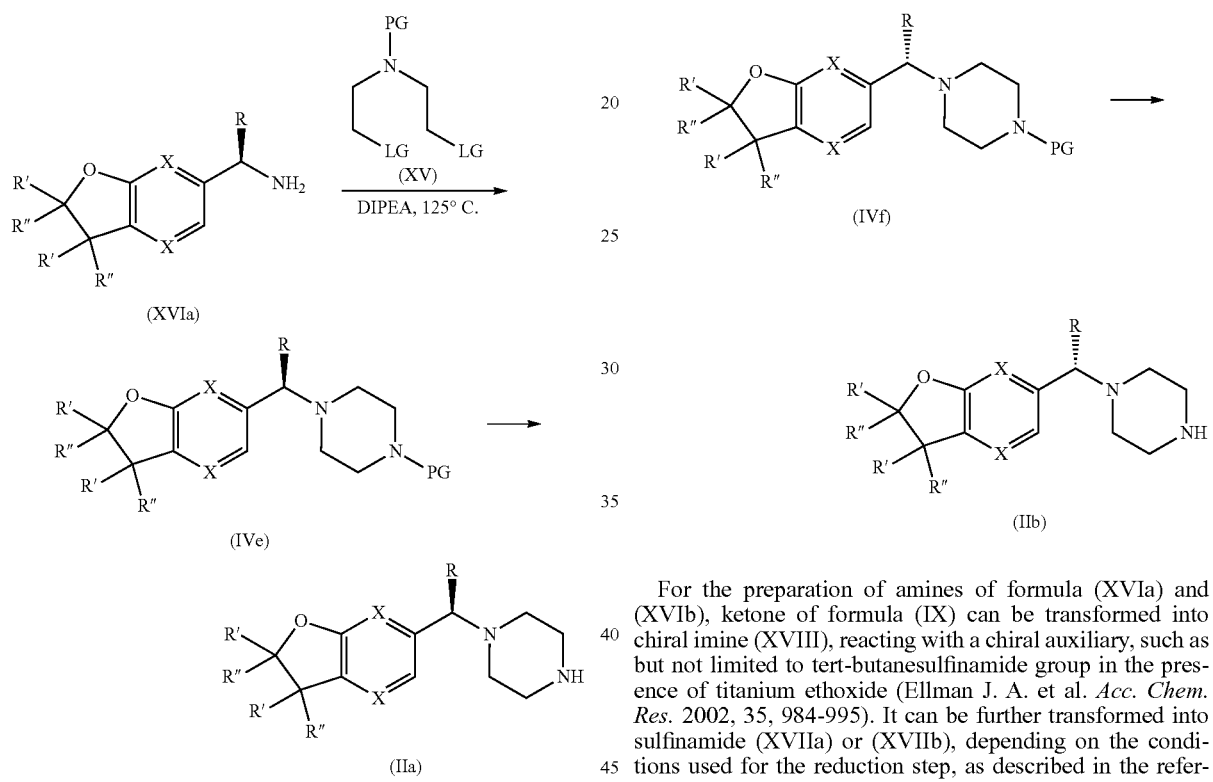

For the preparation of amines of formula (XVIa) and (XVIb), ketone of formula (IX) can be transformed into chiral imine (XVIII), reacting with a chiral auxiliary, such as but not limited to tert-butanesulfinamide group in the presence of titanium ethoxide (Ellman J. A. et al. *Acc. Chem. Res.* 2002, 35, 984-995). It can be further transformed into sulfinamide (XVIIa) or (XVIIb), depending on the conditions used for the reduction step, as described in the reference from Ellman J. A. et al. *J. Org. Chem.* 2007, 72, 626-629.

Scheme 8

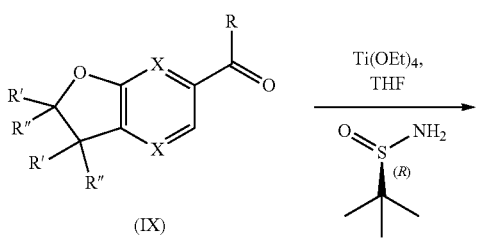

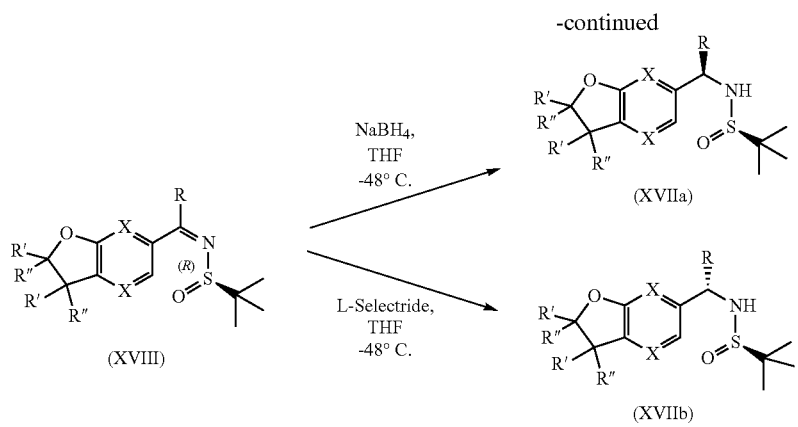

(XVIII)

(XVIIa) → (XVIa)

(XVIIb) → (XVIb)

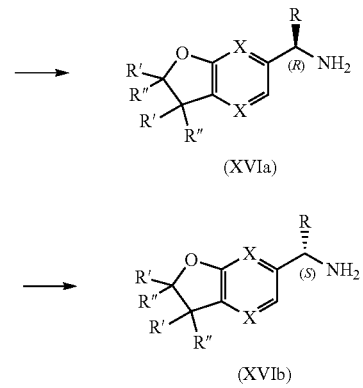

Alternatively aldehyde of formula (XIX) can be transformed into alcohol of formula (VIII) with addition of a suitable nucleophile, such as but not limited to a Grignard reagent (Scheme 9). In another process, ketone of formula (IXa) can be obtained by Stille cross coupling reaction between aryl halide (XX) and tributyl(1-ethoxyvinyl)tin in the presence of a catalyst, such as but not limited to Pd(PPh$_3$)$_2$Cl$_2$ in toluene at temperatures ranging from RT to 110° C. (Scheme 10).

Scheme 9

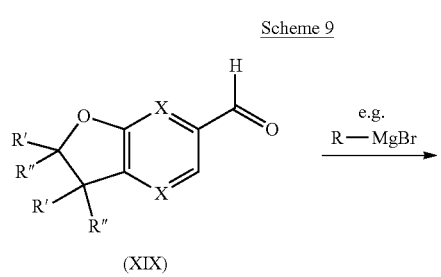

Ketone of formula (IXb), wherein R" is defined as above and R' is methyl, can be obtained from 3-acetylphenol (XXIa). Its alkylation with R"-substituted allyl bromide in the presence of a base, such as but not limited to K$_2$CO$_3$ or Cs$_2$CO$_3$, followed by a Claisen rearrangement, yields a mixture of regioisomers (XXIc) and (XXId). Metal catalyzed cyclization of (XXId) regioisomer, using for example ZrCl$_4$ as metal catalyst, yields ketone of formula (IXb) (Scheme 11).

Scheme 11

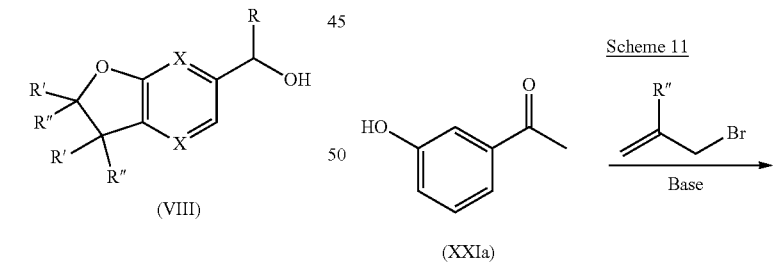

Scheme 10

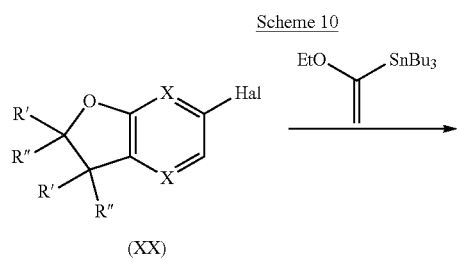

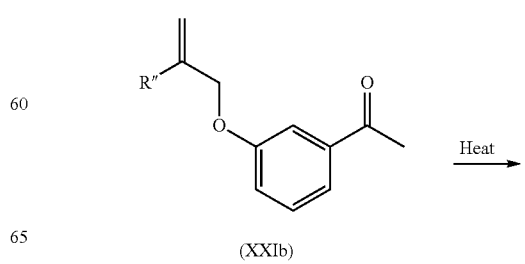

-continued

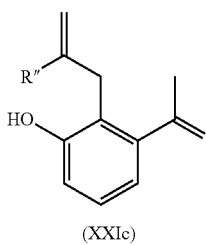
(XXIc)

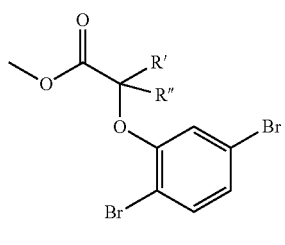
(XXIII)
Reduction →

+

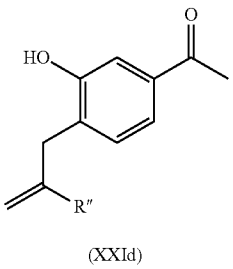
(XXId)

| metal catalyst

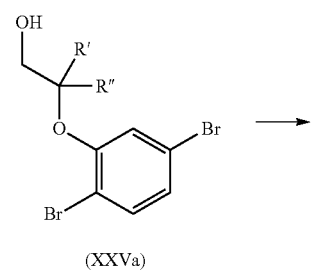
(XXVa)

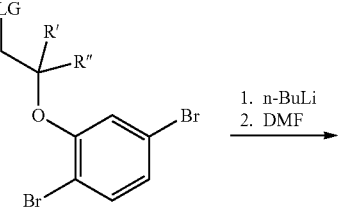
(XXVIa)

1. n-BuLi
2. DMF
→

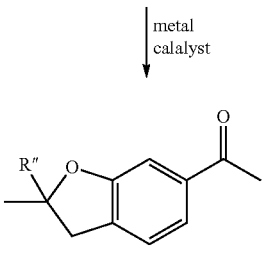
(IXb)

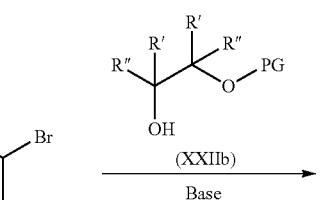
(XIXa)

Alternatively, aldehydes of formula (XIXa) or (XIXb) can be obtained starting from 1,4-dibromo-2-fluorobenzene (Scheme 12). Aromatic substitution with alcohols of formula (XXIIa) followed by ester reduction, yielded alcohol (XXVa). Alternatively, compound (XXIIb) can be obtained by addition of alcohols of formula (XXIIb) to 1,4-dibromo-2-fluorobenzene, followed by a deprotection step. Alcohol functionalities of (XXVa) or (XXVb) can be then transformed into a suitable leaving group LG, such as but not limited to Br, Cl or OMs, using conditions known to a person skilled in the art. Halogen metal exchange using for example n-butyl lithium, trigger dihydrobenzofuran cyclization and followed by the addition of a formyl group with the subsequent addition of DMF.

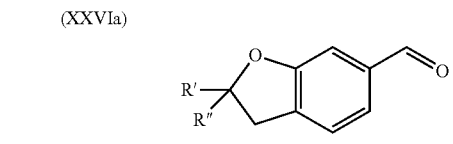
(XXIIb)
Base →

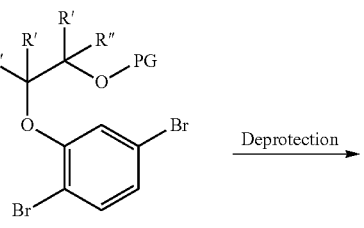
(XXIV)
Deprotection →

Scheme 12

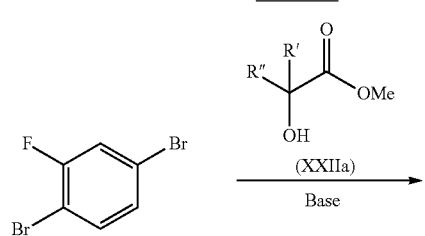
(XXIIa)
Base →

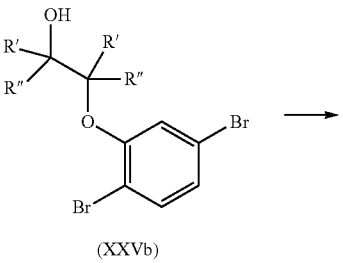
(XXVb)

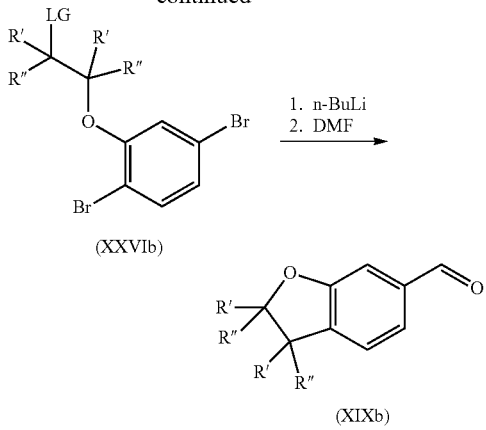

The sulfoximine group and related functionalities as indicated in the definitions can be introduced or generated at any stage of the synthesis of compounds of formula (I), as described below in the examples using methods known by one skilled in the art (Frings, M. et al. *Eur. J. Med. Chem.* 2017, 126, 225-245 and cited references).

When a reaction is preferably performed under basic conditions, a suitable base might be selected from metal oxides, e.g. aluminum oxide, alkaline metal hydroxide (potassium hydroxide, sodium hydroxide and lithium hydroxide, inter alia), alkaline earth metal hydroxide (barium hydroxide and calcium hydroxide, inter alia), alkaline metal alcoholates (potassium ethanolate and sodium propanolate, inter alia), alkaline metal carbonates (e.g., sodium bicarbonate) and several organic bases (e.g., N,N-diisopropylethylamine, piperidine or diethanolamine, inter alia).

The reaction is generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid, acetic acid or trifluoroacetic acid (TFA); nitro compounds, such as nitromethane or nitrobenzene; esters, such as ethyl acetate, or mixtures of the said solvents. Particular preference is given to TFA, DMF, dichloromethane, THF, H$_2$O, methanol, tert. butanol, tert. amylalcohol, triethylamine or dioxane.

Depending on the conditions used, the reaction time is between a few minutes and 14 days, the reaction temperature is between about −80° C. and 140° C., normally between −50° C. and 120° C., preferably between −20° C. and 100° C.

The compounds of formula (I) and sub-formulae thereof are accessible via the routes above. The starting materials, are usually known to the skilled artisan, or they can be easily prepared by known methods.

The compounds of formula (I) can be modified, like hydrogenated or metal-reduced, to remove the chlorine, or put into a substitution reaction, and/or to be transformed with an acid or base into a salt, preferably with a strong acid. Numerous papers and methods are available and useful for the one skilled in the art in respect for organic chemistry, chemical strategies and tactics, synthetic routes, protection of intermediates, cleavage and purification procedure, isolation and characterization. General chemical modifications are known to the one skilled in the art. Halogenation of aryls or hydroxy substitution by halogens of acids, alcohols, phenols, and their tautomeric structures can be preferably carried out by use of POCl$_3$, or SOCl$_2$, PCl$_5$, SO$_2$Cl$_2$. In some instances oxalyl chloride is also useful. Temperatures can vary from 0° C. to reflux depending on the task to halogenate a pyridone structure or a carboxylic acid or a sulfonic acid. Time will also be adjusted from minutes to several hours or even over night. Similarly, alkylation, ether formation, ester formation, amide formation are known to the one skilled in the art. Arylation with aryl boronic acids can be performed in presence of a Pd catalyst, appropriate ligand and base, preferably a carbonate, phosphate, borate salt of sodium, potassium or cesium. Organic bases, like Et$_3$N, DIPEA or the more basic DBU can also be used. Solvents can vary too, from toluene, dioxane, THF, diglyme, monoglyme, alcohols, DMF, DMA, NMP, acetonitrile, in some cases even water, and others. Commonly used catalysts like Pd (PPh$_3$)$_4$, or Pd(OAc)$_2$, PdCl$_2$ type precursors of PdO catalysts have advanced to more complex ones with more efficient ligands. In C—C arylations, instead of boronic acids and esters, aryl-trifluoroborate potassium salts (Suzuki-Miyaura coupling), organo silanes (Hiyama coupling), Grignard reagents (Kumada), organozinc compounds (Negishi coupling) and stannanes (Stille coupling) may be useful. This experience can be transferred to N- and O-arylations. Numerous papers and methods are available and useful for the one skilled in the art in respect of N-arylation and even of electron deficient anilines, and with aryl chlorides and anilines as well as for O-arylation by using Cu catalysis and Pd catalysis.

In the final step of the processes above, a salt of the compounds, preferably those of formula (I), is optionally provided. The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by the reaction of the compound with a suitable base to give the corresponding base-addition salt. Such bases are, for example, alkali metal hydroxides, including potassium hydroxide, sodium hydroxide and lithium hydroxide; alkaline earth metal hydroxides, such as magnesium hydroxide, calcium hydroxide and barium hydroxide; alkali metal alkoxides, for example potassium ethoxide and sodium propoxide; and various organic bases, such as piperidine, diethanolamine and N-methyl-glucamine (meglumine), benzathine, choline, diethanolamine, ethylenediamine, benethamine, diethylamine, piperazine, lysine, L-arginine, ammonia, triethanolamine, betaine, ethanolamine, morpholine and tromethamine. The aluminum salts of the compounds according to the invention are likewise included. In the case of certain compounds of the formula I, which contain a basic center, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as methanesulfonate, ethanesulfonate, toluenesulfonate and benzenesulfonate, and other organic acids and corresponding salts thereof, such as carbonate, acetate, trifluoroacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphorsulfonate, caprate, caprylate, chloride, chlorobenzoate, citrate, cyclamate, cinnamate, cyclopentanepropionate, digluconate, dihydrogenphosphate, dinitrobenzoate, dodecylsulfate, ethanesulfonate, formate, glycolate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Both types of salts may be formed or interconverted preferably using ion-exchange resin techniques.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, me-glumine, nitrate, oleate, phosphonate, pivalate, sodium phosphate, stearate, sulfate, sulfosalicylate, tartrate, thiomalate, tosylate and tro-meth-amine, but this is not intended to represent a restriction.

The acid-addition salts of basic compounds of the formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine. This is not intended to represent a restriction.

The base-addition salts of acidic compounds of the formula I are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound of the formula (I) contains more than one group which is capable of forming pharmaceutically acceptable salts of this type, the formula I also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula (I) can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the Intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the (R) and (S) forms of tartaric acid, diacetyltartaric acid, dibenzoyltartaric acid, di-O-p-toluoyl-tartaric acid, mandelic acid, malic acid, lactic acid, suitable N-protected amino acids (for example N-benzoyl-proline or N-benzenesulfonylproline), or the various optically active camphorsulfonic acids. The suitably formed salt with optically active acid is crystallized using various combinations of solvents, such as but not limited to methanol, ethanol, isopropanol, THF, water, diethyl ether, acetone, methyl tert-butyl ethers and other solvents known to the person skilled in the art. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

When discovering and developing therapeutic agents, the person skilled in the art attempts to optimize pharmacokinetic parameters while retaining desirable in-vitro properties. It is reasonable to assume that many compounds with poor pharmacokinetic profiles are susceptible to oxidative metabolism. In-vitro liver microsomal assays currently available provide valuable information on the course of oxidative metabolism of this type, which in turn permits the rational design of deuterated compounds of the formula (I) with improved stability through resistance to such oxidative metabolism. Significant improvements in the pharmacokinetic profiles of compounds of the formula (I) are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

A further aspect of the invention relates to the use of compounds according to formula (I) and/or physiologically acceptable salts thereof for inhibiting a glycosidase. Such use may be therapeutic or non-therapeuic in character. The term "inhibition" denotes any reduction in glycosidase activity, which is based on the action of the specific inventive compounds capable to interact with the target glycosidase in such a manner that makes recognition, binding and blocking possible. It shall be understood that the compounds of the invention finally interact with the target to unfold the effect. The compounds are characterized by such an appreciable affinity to at least one glycoside hydrolase which ensures a reliable binding and preferably a complete blocking of glycosidase activity. More preferably, the substances are mono-specific in order to guarantee an exclusive and directed recognition with the chosen single glycosidase target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is preferably characterized by high affinity, high selectivity and minimal or even lacking cross-reactivity to other target molecules to exclude unhealthy and harmful impacts to the treated subject.

In a preferred embodiment of the present invention, the glycosidase comprises glycoside hydrolases, more preferably family 84 glycoside hydrolases, most preferably O-glycoprotein-2-acetamido-2deoxy-3-D-glucopyranosidase (OGA), highly preferably a mammalian O-GlcNAcase. It is particularly preferred that the compounds of formula (I) according to the invention selectively bind an O-GlcNAcase, e.g. thereby selectively inhibiting the cleavage of 2-acetamido-2-deoxy-3-D-glucopyranoside (O-GlcNAc) while they do not substantially inhibit a lysosomal 1-hexosaminidase.

The compounds according to the invention preferably exhibit an advantageous biological activity, which is easily demonstrated in enzyme activity assays as described herein or known from prior art. In such in-vitro assays, the compounds preferably exhibit and cause an inhibitory effect. $IC_{50}$ is the concentration of a compound that produces 50% of the maximal inhibition for that compound. The glycosidase target is especially half inhibited by the compounds described herein if the concentration of the compounds amounts to less than 100 μM, preferably less than 10 μM, more preferably less than 1 μM, most preferably less than 0.2 μM. Most preferably, compounds of Formula (I) exhibit an $IC_{50}$ less than 0.02 μM.

A further aspect of the present invention relates to a method for inhibiting a glycosidase, wherein a system capable of expressing the glycosidase, particularly expressing said glycosidase, is contacted with at least one compound of formula (I) according to the invention and/or physiologically acceptable salts thereof, under conditions such that said glycosidase is inhibited. In a preferred embodiment of the method, the glycosidase is contacted with a compound selectively inhibiting O-GlcNAcase and more preferably having an $IC_{50}$ of less than 0.2 μM. It is also preferred that the method is performed in-vitro and/or that the method is not practiced on the human body. A cellular system is preferred in the scope of the method. The cellular system is defined to be any subject provided that the subject comprises cells. The cell refers to any type of primary cells or genetically engineered cells, whether in the isolated status, in culture, as cell line, assembled in tissue, organs or intact laboratory mammals, provided that they are capable of expressing the glycosidase. It shall also be understood that the cell expresses the glycosidase as inherent pre-condition to put the methods of inhibition into practice. Although it is particularly preferred that the cells are capable of expressing or do express the glycosidase, it shall not be excluded that glycosidase-deficient cells can be used and the glycosidase is artificially added to the cellular system. The assay of the invention can be even completely performed in-vitro such that the cell is waived but a glycosidase is contacted with at least one compound of formula (I) according to the invention and/or physiologically acceptable salts thereof. Hence, an amount of isolated glycosidase is provided in crude or purified form for this purpose.

As discussed herein, the glycosidase-signaling pathways are relevant for various diseases, preferably neurodegenerative diseases, diabetes, cancer, cardiovascular diseases and stroke. Accordingly, the compounds according to the invention are useful in the prophylaxis and/or treatment of diseases that are dependent on the said signaling pathways by interaction with one or more of them. The present invention therefore relates to the therapeutic and non-therapeutic use of compounds according to the invention as inhibitors of the signaling pathways described herein, preferably of the OGA-mediated signaling.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to modulate glycosidase activity, usually between about one hour and one week. In-vitro treatment can be carried out using cultivated cells from any sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing OGA-dependent signal transduction pathways in animals and/or cell culture models or in the clinical diseases mentioned in this application.

The use according to the previous paragraphs of the specification may be either performed in-vitro or in-vivo models. The inhibition can be monitored by the techniques described in the course of the present specification. The in-vitro use is preferably applied to samples of humans suffering from neurodegenerative diseases, diabetes, cancer, cardiovascular diseases and stroke. Testing of several specific compounds and/or derivatives thereof makes the selection of that active ingredient possible that is best suited for the treatment of the human subject. The in-vivo dose rate of the chosen derivative is advantageously pre-adjusted to the glycosidase susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of glycosidase activity, preferably OGA activity, if expedient.

A further aspect of the invention relates to a medicament comprising at least one compound according to the invention and/or pharmaceutically usable derivatives, salts, solvates and stereoisomers thereof, including mixtures thereof in all ratios. A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with OGA activity, in such a way that a pathogenic modification of their overall condition or of the condition of particular regions of the organism could establish at least temporarily.

Consequently, the invention also relates to a pharmaceutical composition comprising as active ingredient an effective amount of at least one compound of formula (I) according to the invention and/or physiologically acceptable salts thereof together with pharmaceutically tolerable adjuvants and/or excipients.

In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols.

Furthermore, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially. The present compounds are suitable for combination with agents known to those of skill in the art (e.g., WO 2008/025170) and are useful with the compounds of the invention.

In some embodiments, a compound according to the invention, or for use according to the invention, may be provided in combination with any other active agents or pharmaceutical compositions where such combined therapy may be useful to modulate O-GlcNAcase activity, for example to treat neurodegenerative, inflammatory, cardiovascular, or immunoregulatory diseases or any condition described herein. In some embodiments, a compound according to the invention, or for use according to the invention, may be provided in combination with one or more agents useful in the prevention or treatment of tauopathies and Alzheimer's disease. Examples of such agents may include, without limitation, Acetylcholine esterase inhibitors (AChEIs) such as Aricept® (Donepezil), Exelon® (Rivastigmine), Razadyne® (Razadyne ER®, Reminyl®, Nivalin®, Galantamine), Cognex® (Tacrine), NMDA antagonists such as memantine (Axura®, Ebixa®), Huperzine A, Phenserine, Debio-9902 SR (ZT-1 SR), Zanapezil (TAK0147), ganstigmine, NP7557, a7 nicotinic acetylcholine receptor agonists, 5-HT6 receptor antagonists, M1 muscarinic acetylcholine receptor agonists and positive allosteric modulators, etc Tau aggregation inhibitors such as methylene blue, etc Agents blocking tau aggregation seeding and propagation such as tau antibodies and tau vaccines, etc Microtubule stabilizers such as AL-108, AL-208, paclitaxel, etc Amyloid-β (Aβ) peptide lowering agents such as 1-secretase (BACE-1) inhibitors, senile plaque-clearing biologics such as Aβ antibodies and Aβ vaccines The invention also relates to a set (kit) consisting of separate packs of an effective amount of a compound according to the invention and/or pharmaceutically acceptable salts, derivatives, solvates and stereoisomers thereof, including mixtures thereof in all ratios, and an effective amount of a further medicament active ingredient. The set comprises suitable containers, such as boxes, individual bottles, bags or ampoules. The set may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further medicament active ingredient in dissolved or lyophilized form.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intra-dermal) methods. Such formulations can be prepared using processes known in the pharmaceutical art by, e.g., combining the active ingredient with the excipient(s) or adjuvant(s).

The pharmaceutical composition of the invention is produced in a known way using common solid or liquid carriers, diluents and/or additives and usual adjuvants for pharmaceutical engineering and with an appropriate dosage.

The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with compounds of formula (I) or salts thereof. Examples of suitable excipients are water, vegetable oils, benzyl alcohols, alkylene glycols, polyethylene glycols, glycerol triacetate, gelatin, carbohydrates, e.g. lactose or starch, magnesium stearate, talc and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is adapted for oral administration. The preparations can be sterilized and/or can comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

Accordingly, the invention also relates to a pharmaceutical composition comprising as active ingredient an effective amount of at least one compound of formula (I) according to the invention and/or physiologically acceptable salts thereof together with pharmaceutically tolerable adjuvants for oral administration, optionally in combination with at least another active pharmaceutical ingredient. The prior teaching of the present specification concerning administration route and combination product, respectively, is valid and applicable without restrictions to the combination of both features if expedient.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease. A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

The respective dose or dosage range for administering the pharmaceutical composition according to the invention is sufficiently high in order to achieve the desired prophylactic or therapeutic effect of reducing symptoms of the aforementioned diseases. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation. The prior teaching of the present specification is valid and applicable without restrictions to the pharmaceutical composition comprising the compounds of formula (I) if expedient.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of neurodegenerative diseases, for example tauopathies and Alzheimer's disease, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The pharmaceutical composition of the invention can be employed as medicament in human and veterinary medicine. According to the invention, the compounds of formula (I) and/or physiologically salts thereof are suited for the prophylactic or therapeutic treatment and/or monitoring of diseases that are caused, mediated and/or propagated by OGA activity. It is particularly preferred that the diseases are neurodegenerative diseases, diabetes, cancer, cardiovascular diseases and stroke, more preferably neurodegenerative diseases, most preferably one or more tauopathies, highly preferably Alzheimer's disease and dementia. It shall be understood that the host of the compound is included in the present scope of protection according to the present invention.

Another aspect of the present invention relates to compounds of formula (I) according to the invention and/or physiologically acceptable salts thereof for use in the prophylactic or therapeutic treatment and/or monitoring of diseases that are caused, mediated and/or propagated by OGA activity. Another aspect of the invention concerns compounds of formula (I) according to the invention and/or physiologically acceptable salts thereof for use in the prophylactic or therapeutic treatment and/or monitoring of neurodegenerative diseases, diabetes, cancer, cardiovascular diseases and stroke. The prior teaching of the present specification concerning the compounds of formula (I), including any preferred embodiment thereof, is valid and applicable without restrictions to the compounds according to formula (I) and their salts for use in the prophylactic or therapeutic treatment and/or monitoring of neurodegenerative diseases, diabetes, cancer, cardiovascular diseases and stroke.

Another aspect of the invention relates to a method for treating a disease that is caused, mediated and/or propagated by OGA activity, wherein an effective amount of at least one compound of formula (I) according to the invention and/or physiologically acceptable salts thereof is administered to a mammal in need of such treatment. Another aspect of the invention relates to a method for treating neurodegenerative diseases, diabetes, cancer, cardiovascular diseases and stroke, preferably a tauopathy, wherein an effective amount of at least one compound of formula (I) according to the invention and/or physiologically acceptable salts thereof is administered to a mammal in need of such treatment. The preferred treatment is an oral administration. The prior teaching of the invention and its embodiments is valid and applicable without restrictions to the methods of treatment if expedient.

The neurodegenerative disease or condition is more preferably selected from the group of one or more tauopathies and Alzheimer's disease, Amyotrophic lateral sclerosis (ALS), Amyotrophic lateral sclerosis with cognitive impairment (ALSci), Argyrophilic grain disease, Behavior variant frontotemporal dementia (bvFTD), Bluit disease, Corticobasal degeneration (CBP), Dementia pugilistica, Dementia with Lewy Bodies, Diffuse neurofibrillary tangles with calcification, Down's syndrome, Familial British dementia, Familial Danish dementia, Frontotemporal dementia with parkinsonism linked to chromosome 17 (FTDP-17), Frontotemporal Lobar Degeneration (FTLD), Ganglioglioma, Gangliocytoma, Gerstmann-Straussler-Scheinker disease, Globular glial tauopathy, Guadeloupean parkinsonism, Hallevorden-Spatz disease (neurodegeneration with brain iron accumulation type 1), Lead encephalopathy, Lipofuscinosis, Meningioangiomatosis, Multiple system atrophy, Myotonic dystrophy, Niemann-Pick disease (type C), Pallido-ponto-nigral degeneration, Parkinson's disease, Parkinson's disease dementia (PDD), Parkinsonism-dementia complex of Guam, Pick's disease (PiD), Postencephalitic parkinsonism (PEP), Primary progressive aphasia, Prion diseases (including Creutzfeldt-Jakob Disease (GJD), Variant Creutzfeldt-Jakob Disease (vCJD), Fatal Familial Insomnia, Kuru, Progressive supercortical gliosis, Progressive supranuclear palsy (PSP), Pure Autonomic Failure, Richardson's syndrome, Subacute sclerosing panencephalitis, Tangle-only dementia, Tuberous Sclerosis, Huntington's disease. Most preferred are one ore more tauopathies and Alzheimer's disease.

The invention also relates to the use of compounds according to formula (I) and/or physiologically acceptable salts thereof for the prophylactic or therapeutic treatment and/or monitoring of diseases that are caused, mediated and/or propagated by OGA activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by OGA activity. Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to booster the response and eradicate the pathogens and/or symptoms of the disease completely. Either the identical compound or different compounds can be applied. The medicament can also be used to reducing the likelihood of developing a disorder or even prevent the initiation of disorders associated with OGA activity in advance or to treat the arising and continuing symptoms. The disorders as concerned by the invention are preferably neurodegenerative diseases, diabetes, cancer, cardiovascular diseases and stroke.

In the meaning of the invention, prophylactic treatment is advisable if the subject possesses any preconditions for the aforementioned physiological or pathological conditions, such as a familial disposition, a genetic defect, or a previously passed disease.

In the scope of the present invention, compounds of formula (I) are provided for the first time. The low molecular weight compounds of the invention are strong and selective glycosidase inhibitors with improved passive permeability. The compounds of formula (I) have been shown to be competitive with PUGNAc, a known OGA inhibitor that binds in the substrate pocket. The endogenous substrate is an O-GlcNAcylated protein. O-GlcNAcylation of nuclear and cytoplasmic proteins is one of the most common post-translational modifications in animals and plants. 0-GlcNAc cycling modulates a number of cellular processes, and evidence is mounting that dysregulation of O-GlcNAcylation plays a role in the etiology of several diseases, including tauopathies and Alzheimer's disease. O-GlcNAc transferase (OGT) and O-GlcNAcase (OGA) are the two enzymes that regulate O-GlcNAc cycling. Emerging data suggest that inhibitors that block OGA may help maintain healthy O-GlcNAc levels in tauopathies and Alzheimer's disease patients and thereby inhibit the formation of neurofibrillary tangles. Hence, the current invention comprises the use of compounds of formula (I) in the regulation, modulation and/or inhibition of the glycosidase signal cascade, which can be advantageously applied as research tool, for diagnosis and/or in treatment of any disorders that are responsive to OGA signaling and inhibition.

The low molecular weight inhibitors can be applied either themselves and/or in combination with physical measurements for diagnostics of treatment effectiveness. Medicaments and pharmaceutical compositions containing said compounds and the use of said compounds to treat glycosidase-mediated conditions is a promising, novel approach for a broad spectrum of therapies causing a direct and immediate improvement in the state of health, whether in man and animal. The impact is of special benefit to efficiently combat tauopathies and Alzheimer's disease, either alone or in combination with other neurodegenerative treatments.

Due to the surprisingly appreciable inhibitory activity on OGA, along with passive permeability, the compounds of the invention can be advantageously administered at lower doses compared to other less potent or selective inhibitors of prior art while still achieving equivalent or even superior desired biological effects. In addition, such a dose reduction advantageously leads to less or even no medicinal adverse effects.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

All the references cited herein are incorporated by reference in the disclosure of the invention hereby.

The techniques that are essential according to the invention are described in detail in the specification. Other techniques which are not described in detail correspond to known standard methods that are well known to a person skilled in the art, or the techniques are described in more detail in cited references, patent applications or standard literature. Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The examples are particularly to be construed such that they are not limited to the explicitly demonstrated combinations of features, but the exemplified features may be unrestrictedly combined again provided that the technical problem of the invention is solved. Similarly, the features of any claim can be combined with the features of one or more other claims.

EXPERIMENTAL PART

The compounds according to Formula (I) can be prepared from readily available starting materials by several synthetic approaches, using both solution-phase and solid-phase chemistry protocols or mixed solution and solid phase protocols. Examples of synthetic pathways are described below in the examples. All reported yields are non optimized yields. Unless otherwise stated, compounds of Formula (I) and related formulae obtained as a racemic mixture can be separated to provide an enantiomerically enriched mixture or a pure enantiomer.

The commercially available starting materials used in the following experimental description were purchased from Aldrich, Sigma, ACROS, ABCR, Combi-Blocks, Matrix, Apollo scientific, Alfa Aesar, etc. unless otherwise reported.

The HPLC, MS and NMR data provided in the examples described below are obtained as followed:

$^1$H NMR analyses were carried out using BRUKER NMR, model AV-II and AV-III 400 MHz FT-NMR. Residual signal of deuterated solvent was used as internal reference. Chemical shifts (δ) are reported in ppm in relative to the residual solvent signal (δ=2.50 for $^1$H NMR in DMSO-$d_6$, and 7.26 in $CDCl_3$). s (singlet), d (doublet), t (triplet), q (quadruplet), br (broad), quint (quintuplet).

LCMS Analysis Condition:
Instrument Name:
Agilent Technologies 1290 infinity 11.
Method A:
Method: A-0.1% TFA in $H_2O$, B-0.1% TFA in ACN; flow rate: 2.0 mL/min; column: XBridge C8 (50×4.6 mm, 3.5 μm), +ve mode
Method B:
Method: A-10 mM $NH_4HCO_3$ in $H_2O$, B-ACN; flow rate: 1.0 mL/min; column: XBridge C8 (50×4.6 mm, 3.5 μm), +ve mode HPLC Analysis Condition:
Instrument Name:
Agilent 1200 Series instruments as followed using % with UV detection (maxplot).
Method A:
Method: A-0.1% TFA in $H_2O$, B-0.1% TFA in ACN; flow rate: 2.0 mL/min; column: XBridge C8 (50×4.6 mm, 3.5 μm).
Method B:
Method: A-10 mM $NH_4HCO_3$ in $H_2O$, B-ACN; flow rate: 1.0 mL/min; column: XBridge C8 (50×4.6 mm, 3.5 μm).

Chiral SFC Analysis Condition:
Instrument Name:
THAR-SFC 80 and THAR-SFC 200 (analytical) and Pic SFC 10-150 Ratio between $CO_2$ and co-solvent is ranging between 50:50 and 90:10
Method A:
Mobile Phase: 20 mM Ammonia in Methanol flow: 4 mL/min; COLUMN: Lux C3 (250×4.6) mm, 5 μm
Method B:
Mobile Phase: 0.5% Isopropyl Amine in Methanol, 3 mL/min column: Chiracel OD-H (250×4.6) mm, 5 μm Method C:

Mobile Phase: 20 mmol ammonia in Methanol, 3 mL/min column: Chiracel OJ-H (250×4.6) mm, 5 µm Chiral Preparative SFC Analysis Condition:

Instrument Name:

THAR-SFC 80, THAR-SFC 200 and Pic SFC 10-150

Ratio between $CO_2$ and co-solvent is ranging between 50:50 and 90:10

Method A:

Co-solvent: 20 mM Ammonia in Methanol flow: 5 mL/min; COLUMN: Lux C3 (250×30) mm, 5 µm Method B:

Co-solvent: 0.5% Isopropyl Amine in Methanol, 5 mL/min column: Chiracel OD-H (250×30) mm, 5 µm Method C:

Co-solvent: 20 mmol ammonia in Methanol, 5 mL/min column: Chiracel OJ-H (250×30) mm, 5 µm The microwave chemistry was performed on a single mode microwave reactor Initiator™ Sixty from Biotage.

General flash chromatography conditions used for the purification of intermediates or compounds of Formula I: silica gel 230-400 mesh; gradients used as elutent: 10 to 80% EtOAc in petroleum ether or 1 to 15% MeOH in DCM Intermediate 1:
6-(1-chloroethyl)-2-methyl-2,3-dihydrobenzofuran

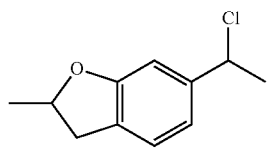

Step 1: 1-(3-(allyloxy)phenyl)ethan-1-one

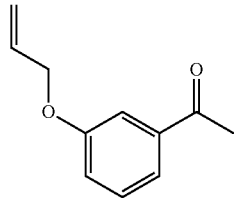

To a stirred solution of 1-(3-hydroxyphenyl)ethan-1-one (25 g, 18.36 mol) in dry acetone (60 mL), potassium carbonate (81.2 g, 58.75 mol) was added at RT and the reaction mixture was stirred RT for 10 min. Allyl bromide (24 ml, 27.54 mol) was then added and the resulting mixture was refluxed for 6 h. Completion of the reaction was monitored by TLC, the reaction mixture was then filtered. The resulting filtrate was concentrated under vacuum to afford the title compound. Yield: 93% (30 g, brown liquid). $^1$H NMR (400 MHz, CDCl$_3$): δ 7.56 (d, J=8.0 Hz, 1H), 7.52 (t, J=2.0 Hz, 1H) 7.39 (t, J=7.6 Hz, 1H), 7.15 (dd, J=8.2, 2.8 Hz, 1H), 6.12-6.11 (m, 1H), 5.46 (dd, J=14.2, 1.2 Hz, 1H), 5.33 (dd, J=10.6, 1.2 Hz, 1H), 4.63-4.61 (m, 2H), 2.62 (s, 3H).

Step 2: Mixture of 1-(4-allyl-3-hydroxyphenyl) ethan-1-one and 1-(2-allyl-3-hydroxyphenyl) ethan-1-one

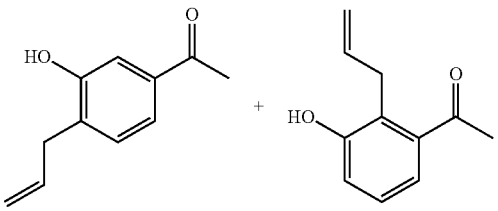

A solution of 1-(3-(allyloxy)phenyl)ethan-1-one (5.0 g, 36.7 mmol) in polyethylene glycol (10 mL) was stirred at 250° C. for 2 h under microwave irradiation. After completion of the reaction (monitored by TLC), water (10 mL) was added to the resulting mixture and the aqueous layer was extracted with EtOAc (2×50 mL). The combined organic layer was dried over anhydrous Na$_2$SO$_4$ and concentrated under vacuum. The resulting crude material was purified by flash chromatography (Biotage Isolera, eluent: 30-50% EtOAc in hexane) to afford the title compound. Based on the LCMS analysis, the ratio between the two regio-isomers was 1.5:1. The mixture of regioisomer was forwarded to the next step as such. Yield: 57% (17 g, pale brown liquid). $^1$H NMR (400 MHz, CDCl$_3$): δ 7.50-7.49 (m, 1H), 7.24-7.20 (m, 2H), 7.01-6.99 (m, 1H), 6.08-6.02 (m, 1H), 5.19-5.08 (m, 1H), 4.15 (s, H), 3.49 (d, J=6.4 Hz, 2H), 2.08 (s, 3H). LCMS: (Method B) 175.2 (M−H), Rt 1: 4.9 min, 53.8%; Rt 2: 2.5 min, 34.3% (Max).

Step 3: 1-(2-methyl-2,3-dihydrobenzofuran-6-yl) ethan-1-one (Isomer A) and 1-(2-methyl-2,3-dihydrobenzofuran-4-yl)ethan-1-one (Isomer B)

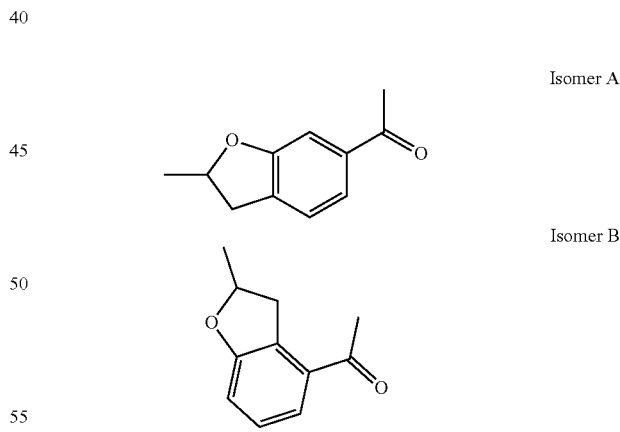

To a stirred solution of 1-(4-allyl-3-hydroxyphenyl) ethan-1-one and 1-(2-allyl-3-hydroxyphenyl) ethan-1-one (17 g, 96.4 mmol) in dry DCM (60 mL), zirconium chloride (44 g, 0.19 mol) was added at RT and the reaction mixture was stirred at RT for 12 h. The reaction mixture was then filtered and the filtrate was concentrated under vacuum. The resulting crude material was purified by flash chromatography (Biotage Isolera, run time: 1.5 h (long run), eluent: 4% EtOAc in hexane) to give title compound to afford isomer A and isomer B.

Analysis of isomer A: Yield: 6.0% (1.5 g, brown liquid). $^1$H NMR (400 MHz, CDCl$_3$): δ 7.49 (t, J=9.2 Hz, 1H), 7.33 (d, J=1.2 Hz, 1H), 7.24 (d, J=7.6 Hz, 1H), 5.03-5.01 (m, 1H), 3.41-3.35 (m, 1H), 2.90-2.84 (m, 1H), 2.57 (t, J=1.2 Hz, 3H), 1.50 (d, J=6.4 Hz, 3H). HPLC: (Method A) Rt. 3.5 min, 99.4% (Max).

Analysis of isomer B: $^1$H NMR (400 MHz, DMSO-d$_6$): δ 7.37 (d, J=7.6 Hz, 1H), 7.24-7.18 (m, 1H), 6.95 (d, J=7.6 Hz, 1H), 5.00-4.94 (m, 1H), 3.72-3.65 (m, 1H), 3.18-3.11 (m, 1H), 2.60 (s, 3H), 1.49-1.47 (m, 3H). LCMS: (Method A) 177.3 (M+H), Rt. 3.7 min, 74.5% (Max).

Step 4:
1-(2-methyl-2,3-dihydrobenzofuran-6-yl)ethan-1-ol

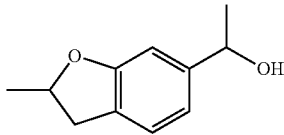

To a stirred solution of 1-(2,3-dihydrobenzofuran-6-yl)ethan-1-one (0.32 g, 1.82 mmol) in methanol (7.4 mL, 20V) at 0° C., NaBH$_4$ (0.14 mL, 3.60 mmol) was added and the reaction mixture was stirred at RT for 60 min. After completion (monitored by TLC), the reaction mixture was quenched with ice-cold water (5 mL) and the aqueous layer was extracted with DCM (2×10 mL). The combined organic layer was washed with brine (5 mL), dried over Na$_2$SO$_4$ and concentrated under vacuum to afford the title compound. Yield: 82.5% (crude, 0.25 g, brown liquid). $^1$H NMR (400 MHz, CDCl$_3$): δ 7.12 (d, J=7.4 Hz, 1H), 6.85 (d, J=7.4 Hz, 1H), 6.80 (s, 1H), 4.97-4.95 (m, 1H), 4.87-4.86 (m, 1H), 3.33-3.31 (m, 1H), 2.83-2.78 (m, 1H), 1.48-1.47 (m, 6H). LCMS: (Method A) 161.2 (M−H$_2$O+H), Rt. 3.1 min, 99.7% (Max).

Step 5:
6-(1-chloroethyl)-2-methyl-2,3-dihydrobenzofuran

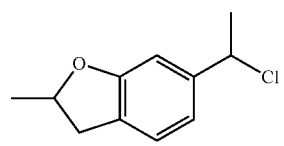

To a stirred solution of 1-(2-methyl-2,3-dihydrobenzofuran-6-yl)ethan-1-ol (0.25 mg, 1.90 mmol) in DCM (10 mL), SOCl$_2$ (0.5 mL, 5.8 mmol) was added at 0° C., and the resulting mixture was stirred at RT for 2 hr. After completion of the reaction (monitored by TLC), the reaction mixture was concentrated under vacuum and the resulting crude was co-distilled with DCM (2×10 mL) to afford the title compound. The resulting solid was used for the next step without further purification. Yield: 80% (275 mg, pale brown gummy solid). $^1$H NMR (300 MHz, CDCl$_3$): δ 7.13 (d, J=7.5 Hz, 1H), 6.85 (m, 2H), 5.09-4.90 (m, 2H), 3.35-3.27 (m, 1H), 2.85-2.77 (m, 1H), 1.83 (d, J=8.00 Hz, 3H), 1.46 (d, J=6.3 Hz, 3H). LCMS: (Method A) 161.2 (M−HCl+H), Rt. 4.3 min 65.2% (Max).

Intermediate 2: N-(5-(piperazin-1-yl)-1,3,4-thiadiazol-2-yl)acetamide hydrochloride

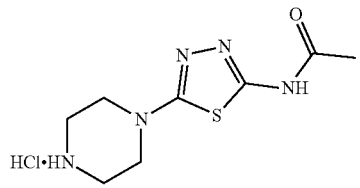

Step 1: tert-Butyl 4-(5-amino-1,3,4-thiadiazol-2-yl)piperazine-1-carboxylate

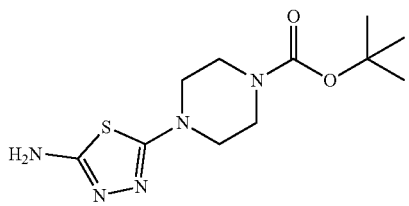 [SMILES: CC(C)(C)OC(=O)N1CCN(c2nnc(N)s2)CC1]

To a stirred solution of 2-amino 5-bromo-1,3,4-thiadiazole (10.0 g, 55.5 mmol) in dry DMF (100 mL), K$_2$CO$_3$ (15.3 g, 111.1 mmol) and 1-boc piperazine (12.4 g, 66.65 mmol) were added at 0° C. and the reaction mixture was stirred at 80° C. overnight. Completion of the reaction was monitored by TLC, then the reaction mixture was concentrated under vacuum. To the resulting mixture DCM (200 mL) was added, the organic layer was washed with water (100 mL), brine (100 mL) and dried over anhydrous Na$_2$SO$_4$. Then the organic layer was concentrated under vacuum and the resulting crude material was purified by flash chromatography (Biotage Isolera, eluent: 2-5% methanol in DCM) to afford the title compound. Yield: 76% (12 g, pale brown solid). $^1$H NMR (400 MHz, DMSO-d$_6$): δ 6.51 (s, 2H), 3.39 (d, J=6.9 Hz, 4H), 3.19 (d, J=7.7 Hz, 4H), 1.39 (s, 9H). LCMS: (Method A) 286.1 (M+H), Rt. 2.7 min, 97.6% (Max).

Step 2: tert-Butyl 4-(5-acetamido-1,3,4-thiadiazol-2-yl)piperazine-1-carboxylate

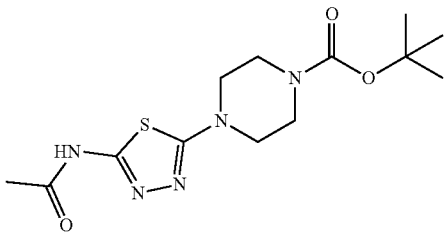 [SMILES: CC(=O)Nc1nnc(N2CCN(C(=O)OC(C)(C)C)CC2)s1]

To a stirred solution of tert-butyl 4-(5-amino-1,3,4-thiadiazol-2-yl)piperazine-1-carboxylate (12.0 g, 42.09 mmol) in pyridine (120 mL), acetic anhydride (5.1 g, 50.5 mmol) was added at 0° C. and the reaction mixture was stirred at 50° C. overnight. After completion of the reaction (monitored by TLC), the reaction mixture was concentrated under vacuum and the obtained material was triturated with diethyl ether (100 mL). The resulting crude material was filtered, dried under vacuum and forwarded to the next step as such without any further purification. Yield: 87% (12 g, off white solid). $^1$H NMR (400 MHz, DMSO-d$_6$): δ 12.07 (bs, 1H), 3.45-3.34 (m, 8H), 2.11 (s, 3H), 1.42 (s, 9H). LCMS: (Method A) 328.0 (M+H), Rt. 3.1 min, 86.3% (Max).

Step 3: N-(5-(Piperazin-1-yl)-1,3,4-thiadiazol-2-yl)acetamide hydrochloride

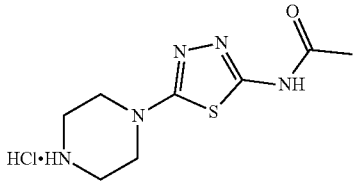

To a stirred solution of tert-butyl 4-(5-acetamido-1,3,4-thiadiazol-2-yl)piperazine-1-carboxylate (12.0 g) in dry 1,4-dioxane (100 mL) at 0° C., HCl solution in dioxane (100 mL, 4M) was added dropwise and the reaction mixture was stirred at RT for 3 h. After completion of the reaction (monitored by TLC), the reaction mixture was concentrated under vacuum and the obtained material was triturated with diethyl ether (50 mL). The resulting material was dried under vacuum and forwarded to the next step as such. Yield: 93% (9 g, white solid). $^1$H NMR (400 MHz, DMSO-d$_6$): δ 12.07 (bs, 1H), 3.67 (s, 4H), 3.21 (s, 4H), 2.13 (s, 3H). LCMS: (Method A) 228.0 (M+H), Rt. 0.7 min, 85.3% (Max).

Intermediate 3: 2-(piperazin-1-yl)-7,8-dihydropyrido[4,3-d]pyrimidin-5 (6H)-one hydrochloride

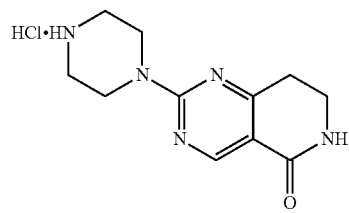

Step 1: tert-butyl 4-carbamimidoylpiperazine-1-carboxylate

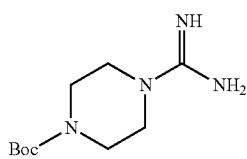 [SMILES: CC(C)(C)OC(=O)N1CCN(C(=N)N)CC1]

To the stirred solution of tert-butyl piperazine-1-carboxylate (20 g, 107.5 mmol) in DMF (200 mL), DIPEA (19.0 mL, 107.5 mmol) followed by 1H-pyrazole-1-carboxamide hydrochloride (15.76 g, 107.5 mmol) were added at RT and the reaction mixture was stirred at 60° C. for 6 h. After completion of the reaction (monitored by TLC), the reaction mixture was cooled at 0° C., MTBE (200 mL) was added and the reaction mixture was stirred for 1 h. The resulting solid material was washed with MTBE (2×50 mL), Et$_2$O (50 mL) and dried under vacuum to afford the title compound. Yield: 83% (20 g, white solid). $^1$H NMR (400 MHz, DMSO-d$_6$): δ 7.71-7.69 (m, 3H), 3.44-3.34 (m, 8H), 1.42 (s, 9H).

Step 2: 3-((dimethylamino) methylene)piperidine-2,4-dione

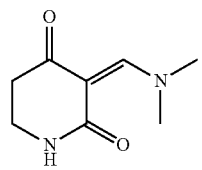

To a stirred solution of 2,4-piperidinedione (10 g, 88.4 mmol) in ACN (100 mL), N, N-dimethyl formamide dimethylacetal (23.5 mL, 176.8 mmol) was added and the reaction mixture was stirred at RT overnight. After completion of the reaction (monitored by TLC), the resulting reaction mixture was evaporated under vacuum, the obtained crude material was triturated with diethyl ether (2×20 mL) and dried to afford the title compound. Yield: 92% (13.6 g, brown solid). $^1$H NMR (300 MHz, DMSO-d$_6$): δ 7.83 (s, 1H), 7.15 (s, 1H), 3.29 (s, 3H), 3.16 (t, J=6.3 Hz, 2H), 3.06 (s, 3H), 2.30 (t, J=6.3 Hz, 2H). LCMS: (Method A) 169.2 (M+H), Rt. 1.2 min, 90.4%.

Step 3: tert-butyl-4-(5-oxo-5,6,7,8-tetrahydropyrido[4,3-d]pyrimidin-2-yl)piperazine-1-carboxylate

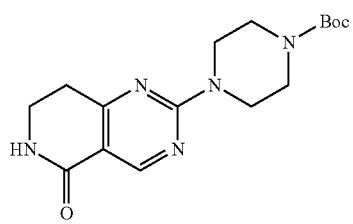 [SMILES: CC(C)(C)OC(=O)N1CCN(c2ncc3c(n2)CCNC3=O)CC1]

To a stirred solution of tert-butyl 4-carbamimidoylpiperazine-1-carboxylate (18.32 g, 80.2 mmol) and 3-((dimethylamino) methylene) piperidine-2,4-dione (13.5 g, 80.2 mmol) in EtOH (135 mL), K$_2$CO$_3$ (26.66 g, 193.0 mmol) was added and the reaction mixture was heated at 80° C. for 6 h. After completion of the reaction (monitored by TLC), the reaction mixture was cooled to RT and the obtained precipitate was collected by filtration. The resulting crude material was washed with EtOH (30 mL), water (3×30 mL), diethyl ether (2×20 mL) and dried under vacuum to afford the title compound. Yield: 85% (22.7 g, white solid). $^1$H NMR (300 MHz, DMSO-d$_6$): δ 8.63 (s, 1H), 7.74 (s, 1H), 3.85-3.81 (m, 4H), 3.41-3.39 (m, 6H), 2.82 (t, J=6.3 Hz, 2H), 1.43 (s, 9H). LCMS: (Method A) 334.2 (M+H), Rt. 3.4 min, 99.4% (Max).

Step 4: 2-(piperazin-1-yl)-7,8-dihydropyrido[4,3-d] pyrimidin-5 (6H)-one hydrochloride

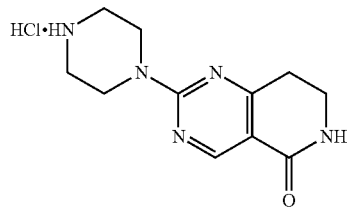

To a stirred solution of tert-butyl-4-(5-oxo-5,6,7,8-tetrahydropyrido[4,3-d]pyrimidin-2-yl)piperazine-1-carboxylate (22 g, 66.0 mmol) in 1,4-dioxane (66 mL) at 0° C., HCl solution in dioxane (110 mL, 5V, 4M) was added dropwise and the reaction mixture was stirred at RT for 4 h. After completion of the reaction (monitored by TLC), the reaction mixture was filtered and the obtained solid was washed with EtOAc (3×30 mL). The resulting material was dried under vacuum to afford the title compound which was forwarded to the next step as such. Yield: 94% (19 g, white solid). LCMS: (Method A) 234.2 (M+H), Rt. 0.6 min, 94.8% (Max).

Intermediate 4: (2R)-6-(1-chloroethyl)-2-methyl-2, 3-dihydrobenzofuran

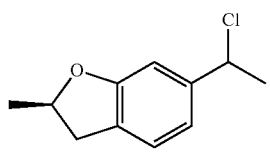

Step 1: (R)-1-(trityloxy)propan-2-ol

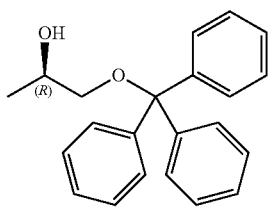

To a stirred solution of (R)-propane-1, 2-diol (15.0 g, 0.19 mol) in DCM (300 mL) at 0° C., TEA (44.37 mL, 0.31 mol) and tritylchloride (56 g, 0.20 mol) in DCM (100 mL) were added slowly under nitrogen atmosphere and the reaction mixture was stirred at RT overnight. After completion of the reaction (monitored by TLC), the reaction mixture was quenched with sat. NH$_4$Cl (150 mL) and the aqueous layer was extracted with DCM (2×100 mL). The combined organic layer was washed with water (100 mL), brine (100 mL), dried over anhydrous Na$_2$SO$_4$ and evaporated under vacuum to afford the title compound. Yield: 84% (52.09 g, pale yellow gummy liquid). $^1$H NMR (400 MHz, CDCl$_3$): δ 7.49-7.42 (m, 6H), 7.35-7.29 (m, 6H), 7.28-7.25 (m, 3H), 4.03-3.98 (m, 1H), 3.16 (dd, J=9.2, 3.2 Hz, 1H), 3.02 (dd, J=9.2, 8.0 Hz, 1H), 2.39 (s, 1H), 1.09 (d, J=6.4 Hz, 3H).

Step 2: (R)-((2-(2,5-dibromophenoxy)propoxy) methanetriyl)tribenzene

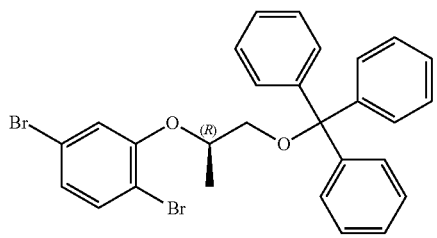

To a stirred solution of 1, 4-dibromo-2-fluorobenzene (32 g, 0.13 mmol) and (R)-1-(trityloxy)propan-2-ol (44.24 g, 0.14 mmol) in THF (300 mL), KOtBu (56.8 g, 0.5 mmol) was added batchwise over 25 min at 5° C. and the reaction mixture was heated at 70° C. overnight. After completion of the reaction (monitored by TLC), the mixture was cooled to RT, diluted with water (150 mL) and the aqueous layer was extracted with EtOAc (2×150 mL). The combined organic layer was washed with water (100 mL), brine (100 mL), dried over anhydrous Na$_2$SO$_4$ and concentrated under vacuum. The resulting crude material was purified by flash chromatography (Biotage Isolera, eluent: 6% EtOAc in hexane) to afford the title compound. Yield: 65% (45.3 g, off white solid). $^1$H NMR (400 MHz, CDCl$_3$): δ 7.48-7.41 (m, 7H), 7.36-7.12 (m, 11H), 4.60-4.57 (m, 1H), 3.46 (dd, J=10.0, 6.4 Hz, 1H), 3.17 (dd, J=10.0, 6.2 Hz, 1H), 1.33 (d, J=6.4, Hz, 3H).

Step 3: (R)-2-(2, 5-dibromophenoxy) propan-1-ol

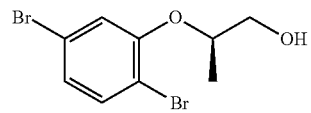

To a stirred solution of (R)-((2-(2,5-dibromophenoxy) propoxy)methanetriyl)tribenzene (25 g, 32.54 mmol) in dry DCM (250 mL), 10% TFA in DCM (50 mL) was added dropwise at 0° C. and the reaction mixture was stirred at RT for 1 h. After completion of the reaction (monitored by TLC), the mixture was cooled to 0° C., quenched with sat. NaHCO$_3$ and the aqueous layer was extracted with DCM (2×150 mL). The combined organic layer was washed with brine (30 mL), dried over anhydrous Na$_2$SO$_4$ and concentrated under vacuum. The resulting crude material was purified by flash chromatography (Biotage Isolera, eluent: 18% EtOAc in hexane) to afford the title compound. Yield: 32% (7.5 g, pale brown gummy oil). $^1$H NMR (400 MHz, CDCl$_3$): δ 7.41 (d, J=8.4 Hz, 1H), 7.12 (s, 1H), 7.02 (d, J=8.8 Hz, 1H), 4.52-4.48 (m, 1H), 3.79 (m, 2H), 1.36 (d, J=6.4 Hz, 3H). HPLC: (Method A), Rt. 4.2 min, 99.7% (Max). Chiral SFC: (Method D), Rt 2.7 min, 96.6%.

Step 4: (R)-1, 4-dibromo-2-((1-bromopropan-2-yl)oxy)benzene

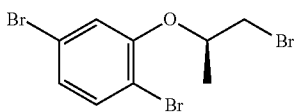

To a stirred solution of (R)-2-(2, 5-dibromophenoxy)propan-1-ol (7.0 g, 22.5 mmol) in DCM (70 mL), TPP (7.09 g, 27.09 mmol) and CBr$_4$ (8.98 g, 27.09 mmol) were added under nitrogen atmosphere at 0° C. and the reaction mixture was stirred for 2 h at RT. After completion of the reaction (monitored by TLC), the mixture was evaporated under vacuum and the resulting crude material was purified by flash chromatography (Biotage Isolera, eluent: 10% EtOAc in hexane) to afford the title compound. Yield: 62% (5.1 g, pale brown gummy solid). $^1$H NMR (400 MHz, CDCl$_3$): δ 7.43 (dd, J=8.4, 1.6 Hz, 1H), 7.09 (d, J=2.0 Hz, 1H), 7.09-7.03 (m, 1H), 4.58 (m, 1H), 3.61 (dd, J=10.6, 5.2 Hz, 1H), 3.50 (dd, J=8.4, 1.2 Hz, 1H), 1.53 (d, J=6.0 Hz, 3H).

Step 5: (R)-2-methyl-2, 3-dihydrobenzofuran-6-carbaldehyde

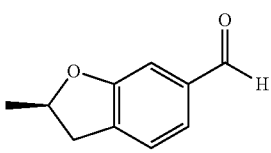

To a stirred solution of (R)-1, 4-dibromo-2-((1-bromopropan-2-yl)oxy)benzene (4.8 g, 0.013 mol) in dry THF (40 mL) under nitrogen atmosphere, n-butyl lithium (8.8 mL, 0.014 mol, 1.6 M in hexane) was added slowly over 10 min at −78° C. and stirred for 1 h. Second lot of n-butyl lithium (8.8 mL, 0.014 mol, 1.6 M in hexane) was added slowly over 10 min at −78° C. and stirring was continued for another 1 h. Then DMF (1.0 mL, 12.8 mmol) was added slowly, maintained for 45 min at −78° C. and completion of reaction was monitored by TLC. The reaction mixture was then warmed to 10° C., quenched with sat.NH$_4$Cl solution (20 mL) and the aqueous layer was extracted with EtOAc (2×25 mL). The combined organic layer was washed with water (10 mL), brine solution (5 mL), dried over anhydrous Na$_2$SO$_4$ and evaporated under vacuum. The resulting crude material was purified by flash chromatography (Biotage Isolera, eluent: 15-20% EtOAc in hexane) to afford the title compound. Yield: 78% (1.7 g, brown gummy oil). $^1$H NMR (400 MHz, CDCl$_3$): δ 9.92 (s, 1H), 7.39 (dd, J=7.4, 1.2 Hz, 1H), 7.31 (d, J=7.8 Hz, 1H), 7.24 (s, 1H), 5.04-4.99 (m, 1H), 3.40 (dd, J=16.4, 8.8 Hz, 1H), 2.89 (dd, J=14.0, 2.8 Hz, 1H), 1.51 (d, J=6.4 Hz, 3H). LCMS: (Method A) 163.1 (M+H), Rt. 3.4 min, 64.6% (Max).

Step 6: 1-((R)-2-methyl-2, 3-dihydrobenzofuran-6-yl)ethan-1-ol

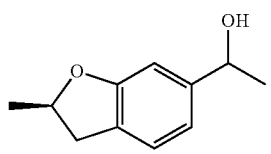

To a stirred solution of (R)-2-methyl-2, 3-dihydrobenzofuran-6-carbaldehyde (1.6 g, 9.80 mmol) in dry THF (10 mL) under nitrogen atmosphere, methyl magnesium chloride solution (4.9 mL, 0.02 mol, 3 M in THF) was added slowly over 10 min at 0° C. and stirred for 2 h. Completion of the reaction was monitored by TLC, then the reaction mixture quenched by sat.NH$_4$Cl solution (10 mL) and the aqueous layer was extracted with EtOAc (2×15 mL). The combined organic layer was washed with water (5 mL), brine solution (2 mL), dried over anhydrous Na$_2$SO$_4$ and evaporated under vacuum. The resulting crude material was purified by flash chromatography (Biotage Isolera, eluent: 18% EtOAc in pet ether) to afford the title compound. Yield: 91% (1.0 g, pale yellow liquid). $^1$H NMR (400 MHz, CDCl$_3$): δ 7.14 (d, J=7.6 Hz, 1H), 6.86 (dd, J=7.4, 1.6 Hz, 1H), 6.81 (s, 1H), 4.98-4.92 (m, 1H), 4.86 (q, J=6.4 Hz, 1H), 3.31 (dd, J=15.2, 8.8 Hz 1H), 2.81 (dd, J=15.6, 7.6 Hz, 1H), 1.52 (s, 3H), 1.51 (d, J=6.8 Hz, 3H). LCMS: (Method A) 161.0 (M−H$_2$O+H), Rt 2.2 min, 81.1% (Max).

Step 7: (2R)-6-(1-chloroethyl)-2-methyl-2, 3-dihydrobenzofuran

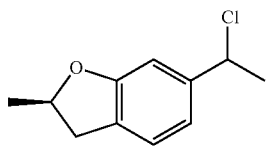

To a stirred solution of 1-((R)-2-methyl-2, 3-dihydrobenzofuran-6-yl)ethan-1-ol (0.5 g, 2.80 mmol) in DCM (20 mL), SOCl$_2$ (0.48 mL, 4.79 mmol) was added 0° C. and the reaction mixture was stirred at RT for 1 h. After completion of reaction (monitored by TLC), the mixture was concentrated under vacuum and the resulting crude material was co-distilled with dry DCM (2×500 mL) to afford the title compound. Yield: 98% (crude, 500 mg, brown gummy oil). LCMS: (Method A) 161.0 (M−HCl+H), Rt. 4.9 min, 35.9% (Max).

Intermediate 5: (2S)-6-(1-chloroethyl)-2-methyl-2,3-dihydrobenzofuran

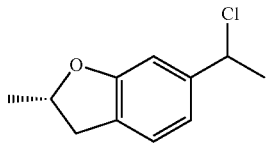

Step 1: (S)-1-(trityloxy)propan-2-ol

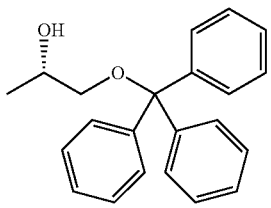 [SMILES: C[C@H](O)COC(c1ccccc1)(c1ccccc1)c1ccccc1]

To a stirred solution of (S)-propane-1, 2-diol (10 g, 0.13 mol) in DCM (200 mL), TEA (30 ml 0.21 mol) and tritylchloride (36.63 g, 0.13 mol) in DCM (100 mL) were added slowly at 0° C. under nitrogen atmosphere and the reaction mixture was stirred at RT overnight. Completion of the reaction was monitored by TLC, then the reaction mixture was quenched with sat. NH$_4$Cl (150 mL) and the aqueous layer was extracted with DCM (2×100 mL). The combined organic layer was washed with water (100 mL), brine (50 mL), dried over anhydrous Na$_2$SO$_4$ and concentrated under vacuum to afford the title compound. Yield: 71% (30 g, pale yellow gummy oil). $^1$H NMR (400 MHz, CDCl$_3$): δ 7.49-7.463 (m, 6H), 7.39-7.28 (m, 6H), 7.28-7.23 (m, 3H), 4.04-3.99 (m, 1H), 3.18 (dd, J=9.4, 3.6 Hz, 1H), 3.06-3.00 (m, 1H), 2.46 (d, J=3.2 Hz 1H), 1.14 (d, J=6.4 Hz, 3H). HPLC: (Method A), Rt. 5.5 min, 85.1% (Max).

Step 2: (S)-((2-(2, 5-dibromophenoxy)propoxy)methanetriyl)tribenzene

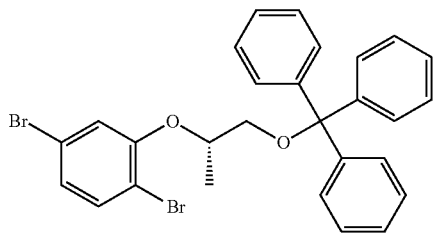 [SMILES: C[C@@H](COC(c1ccccc1)(c1ccccc1)c1ccccc1)Oc1cc(Br)ccc1Br]

To a stirred solution of 1, 4-dibromo-2-fluorobenzene (22 g, 0.09 mol) and (S)-1-(trityloxy)propan-2-ol (27.65 g, 0.09 mol) in THF (300 mL), K$^t$OBu (21.48 g, 0.191 mol) was added batchwise over 25 min at 5° C. and the reaction mixture was stirred at 70° C. overnight. After completion of the reaction (monitored by TLC), the mixture was cooled to RT, diluted with water (100 mL) and the aqueous layer was extracted with EtOAc (2×100 mL). The combined organic layer was washed with water (100 mL), brine (100 mL), dried over anhydrous Na$_2$SO$_4$ and concentrated under vacuum. The resulting crude material was triturated with EtOAc to afford the title compound. Yield: 66% (25 g, off white solid). $^1$H NMR (400 MHz, CDCl$_3$): δ 7.56 (d J=8.0 Hz 1H), 7.49 (s, 1H), 7.31-7.25 (m, 15H), 7.10 (dd, J=8.2, 1.2 Hz, 1H), 4.93 (s, 1H), 3.19 (dd, J=9.8, 6.8 Hz, 1H), 3.07 (d, J=7.6 Hz, 1H), 1.22 (d, J=6.4 Hz, 3H).

Step 3: (S)-2-(2, 5-dibromophenoxy) propan-1-ol

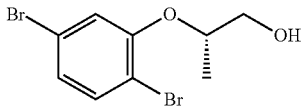

To a stirred solution of (S)-((2-(2, 5-dibromophenoxy)propoxy)methanetriyl)tribenzene (25 g, 45.28 mol) in dry DCM (250 mL), 10% TFA in DCM (100 mL) was added slowly at −20° C. and the reaction mixture was stirred for 2 h. Completion of the reaction was monitored by TLC, then the reaction mixture was quenched with sat. Na$_2$CO$_3$ at 0° C. and the aqueous layer was extracted with DCM (2×150 mL). The combined organic layer was washed with brine (40 mL), dried over anhydrous Na$_2$SO$_4$ and concentrated under vacuum. The resulting crude material was purified by recrystallization using methanol to afford the title compound. Yield: 57% (8.0 g, pale brown gummy oil). $^1$H NMR (400 MHz, CDCl$_3$): δ 7.41 (d, J=8.3 Hz, 1H), 7.12 (d, J=2.0 Hz, 1H), 7.02 (dd, J=6.4, 2.1 Hz, 1H), 4.50 (t, J=4.4 Hz, 1H) 3.78 (t, J=4.1 Hz, 2H), 1.36 (d, J=6.2 Hz, 3H). HPLC: (Method A), Rt. 4.4 min, 97.1% (Max). Chiral SFC: (Method D) Rt. 3.3 min, 99.1% (Max).

Step 4: (S)-1, 4-dibromo-2-((1-bromopropan-2-yl)oxy)benzene

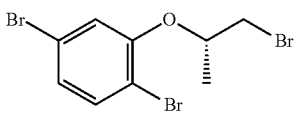

To a stirred solution of TPP (14.21 g, 0.06 mol) in DCM (50 ml), CBr$_4$ (19.8 g, 0.06 mmol) was added slowly portion wise at 0° C. over 15 min, then (S)-2-(2, 5-dibromophenoxy)propan-1-ol (5.6 g, 0.02 mol) in DCM (20 mL) was added to it and the reaction mixture was stirred for 2 h at RT. Completion of the reaction was monitored by TLC, then the reaction mixture was evaporated under vacuum. The resulting crude material was purified by flash chromatography (Biotage Isolera, eluent: 10% EtOAc in hexane) to afford the title compound. Yield: 83% (5.1 g, pale brown gummy solid). $^1$H NMR: (400 MHz, DMSO-d$_6$): δ 7.53 (d, J=8.4 Hz, 1H), 7.43 (d, J=1.6 Hz, 1H), 7.11 (dd, J=8.4, 2.0 Hz, 1H), 4.90-4.88 (m, 1H), 3.77 (dd, J=11.0, 3.6 Hz, 1H), 3.67 (dd, J=11.2, 5.2, Hz, 1H), 1.34 (d, J=6.0 Hz, 3H).

Step 5: (S)-2-methyl-2, 3-dihydrobenzofuran-6-carbaldehyde

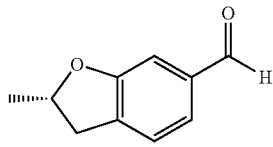

To a stirred solution of (S)-1, 4-dibromo-2-((1-bromopropan-2-yl)oxy)benzene (5.1 g, 0.01 mol) in dry THF (51 mL) under nitrogen atmosphere, n-Butyl lithium (9.42 mL, 0.02 mol, 1.6 M in hexane) was added slowly over 10 min at −78° C. After 1 h at the same temperature second lot of n-Butyl lithium (9.42 mL, 0.02 mol, 1.6 M in hexane) was added slowly over 10 min and stirring was continued for another 1 h. Then DMF (2.15 mL, 27.4 mmol) was added slowly maintaining at −78° C. for 45 min and completion of the reaction was monitored by TLC. The reaction mixture was then warmed to 10° C., quenched with sat. NH$_4$Cl solution (20 mL) and the aqueous layer was extracted with EtOAc (2×25 mL). The combined organic layer was washed with water (10 mL), brine solution (5 mL), dried over anhydrous Na$_2$SO$_4$ and evaporated under vacuum. The resulting crude material was purified by flash chromatography (Biotage Isolera, eluent: 8% EtOAc in hexane) to afford the title compound. Yield: 72% (1.6 g, brown gummy oil). $^1$H NMR (400 MHz, CDCl$_3$): δ 9.93 (s, 1H), 7.39 (d, J=7.2 Hz, 1H), 7.33 (d, J=2.4 Hz, 1H), 7.29 (dd, J=7.8, 1.6, Hz, 1H), 5.05-5.01 (m, 1H), 3.40 (dd, J=16.4, 8.8 Hz, 1H), 2.90 (dd, J=16.6, 7.6 Hz, 1H), 1.51 (d, J=6.2 Hz, 3H). LCMS: (Method A) 163.1 (M+H), Rt. 2.5 min, 69.9% (Max).

Step 6: 1-((S)-2-methyl-2, 3-dihydrobenzofuran-6-yl)ethan-1-ol

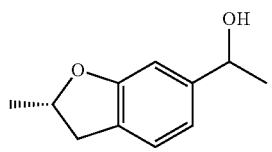

To a stirred solution of (S)-2-methyl-2, 3-dihydrobenzofuran-6-carbaldehyde (1.6 g, 9.80 mmol) in dry THF (16 mL) under nitrogen atmosphere, methyl magnesium chloride solution (4.9 mL, 0.02 mol, 3 M in THF) was added dropwise over 10 min at 0° C. and stirred for 2 h at the same temperature. After completion of the reaction (monitored by TLC), the mixture was quenched by sat. $NH_4Cl$ solution (10 mL) and the aqueous layer was extracted with EtOAc (2×15 mL). The combined organic layer was washed with water (5 mL), brine solution (2 mL), dried over anhydrous $Na_2SO_4$ and evaporated at 45° C. under vacuum. The resulting crude material was purified by flash chromatography (Biotage Isolera, eluent: 18% EtOAc in pet ether) to afford the title compound. Yield: 69% (1.22 g, pale yellow liquid). $^1$H NMR (400 MHz, $CDCl_3$): δ 7.14 (d, J=7.6 Hz, 1H), 6.86 (dd, J=7.6, 1.8, Hz, 1H), 6.81 (s, 1H), 4.98-4.93 (m, 1H), 4.84 (q, J=6.4 Hz, 1H), 3.32 (dd, J=15.2, 8.8 Hz, 1H), 2.82 (dd, J=15.6, 7.6 Hz, 1H), 1.56 (d, J=6.2 Hz, 3H), 1.47 (d, J=6.8 Hz, 3H). LCMS: (Method A) 161.1 (M–$H_2O$+H), Rt 2.2 min, 97.3% (Max).

Step 7: (2S)-6-(1-chloroethyl)-2-methyl-2, 3-dihydrobenzofuran

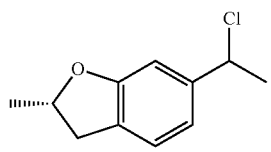

To a stirred solution of 1-((S)-2-methyl-2, 3-dihydrobenzofuran-6-yl)ethan-1-ol (1.2 g, 6.7 mmol) in DCM (12 mL), $SOCl_2$ (1.5 mL, 20.1 mmol) was added at 0° C. and the reaction mixture was stirred at RT for 1 h. After completion of the reaction, the reaction mixture was concentrated under vacuum and the resulting crude material was co-distilled with dry DCM (3×5 mL) to afford the title compound. Yield: 98% (crude) (1.2 g, brown gummy oil).

Intermediate 6: 6-(1-chloroethyl)-2,2-dimethyl-2,3-dihydrobenzofuran

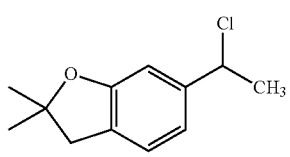

Step 1: 1-bromo-3-((2-methylallyl) oxy)benzene

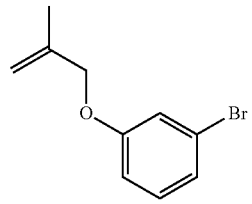

To a stirred solution of 3-bromophenol (Oakwood products, 10.0 g, 28.90 mmol) in dry acetone (60 mL), $K_2CO_3$ (8 g, 86.7 mmol) was added at RT and stirred for 10 min. Then 2-methyl-3-bromopropene (3.2 mL, 31.7 mmol) was added and the reaction mixture was refluxed for 6 h. Completion of the reaction was monitored by TLC, the reaction mixture was then filtered and the filtrate part was concentrated under vacuum. The resulting crude material was used in the next step without any further purification. Yield: 84% (11.0 g, brown liquid). $^1$H NMR (400 MHz, $CDCl_3$): 7.28 (s, 1H), 7.17-7.01 (m, 2H), 6.89-6.86 (m, 1H), 5.10 (s, 1H), 5.02 (s, 1H), 4.44 (s, 2H), 1.85 (s, 3H).

Step 2: 5-bromo-2-(2-methylallyl) phenol and 3-bromo-2-(2-methylallyl) phenol

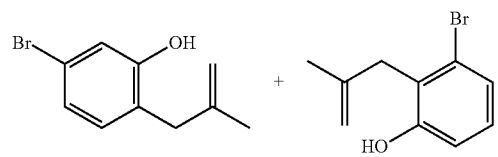

1-Bromo-3-((2-methylallyl)oxy) benzene (11.0 g, 48.4 mmol) was added in polyethylene glycol (50 mL) at RT and the reaction mixture was stirred at 250° C. for 1 h under microwave irradiation. After completion of the reaction (monitored by TLC), water (100 mL) was added to the resulting mixture and the aqueous layer was extracted with EtOAc (2×100 mL). The combined organic layer was dried over $Na_2SO_4$ and concentrated under vacuum. The resulting crude material was purified by flash chromatography (Biotage Isolera, eluent: 30-50% EtOAc in pet ether) to afford the title compound. The mixture of regioisomers (1.4:1) was used as such for the next step. Yield: 91% (10 g, brown liquid). $^1$H NMR (400 MHz, $CDCl_3$): δ 7.28 (s, 1H), 7.21-6.90 (m, 2H), 6.96-6.80 (m, 2H), 3.34 (s, 2H), 1.82 (s, 3H). LCMS: (Method B) 225.0 (M–H), Rt1: 6.4 min, 52.3%, Rt 2: 6.6 min, 36.3% (Max).

Step 3: 6-bromo-2, 2-dimethyl-2, 3-dihydrobenzofuran and 4-bromo-2, 2-dimethyl-2, 3-dihydrobenzofuran

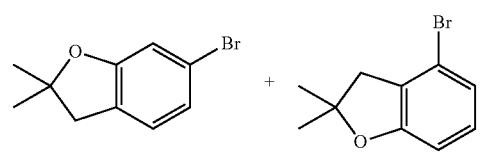

A stirred solution of 5-bromo-2-(2-methylallyl)phenol and 3-bromo-2-(2-methylallyl)phenol regioisomer mixture (10 g, 44.0 mmol) in formic acid (30 mL) was refluxed for 10 h. Completion of the reaction was monitored by TLC and the reaction mixture was concentrated completely under vacuum. The resulting crude material was purified by flash chromatography (Biotage Isolera, eluent: 15% EtOAc in pet ether) to afford the title compound. The mixture of regioisomer was forwarded to the next step as such. Yield: 80% (8 g, dark brown liquid). $^1$H NMR (400 MHz, CDCl$_3$): δ 6.98 (t, J=2.0 Hz, 1H), 6.96 (s, 1H), 6.66 (dd, J=6.8, 2.4 Hz, 1H), 3.03 (d, J=1.2 Hz, 1H), 2.96 (s, 1H), 1.51 (d, J=2.0 Hz, 3H), 1.48 (d, J=2.0 Hz, 3H).

Step 4: 1-(2,2-dimethyl-2, 3-dihydrobenzofuran-6-yl)ethan-1-one (Isomer A) and 1-(2,2-dimethyl-2,3-dihydrobenzofuran-4-yl)ethan-1-one (Isomer B)

Isomer A

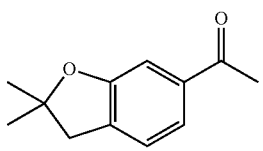

Isomer B

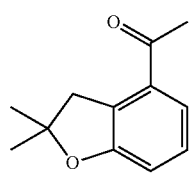

To a degassed solution of 6-bromo-2, 2-dimethyl-2, 3-dihydrobenzofuran and 3-bromo-2, 2-dimethyl-2, 3-dihydrobenzofuran regioisomer mixture (7.6 g, 33.5 mmol) in dry toluene (100 mL), 1-ethoxy vinyl tributyl tin (14 ml, 40.15 mmol) and Pd(PPh$_3$)$_2$Cl$_2$ (940 mg, 1.2 mmol) were added and the resulting mixture was heated at 90° C. overnight. Completion of the reaction was monitored by TLC, then an aqueous solution of HCl (6N, 50 mL) was added and the mixture was stirred at 40° C. for 1 h. The reaction mixture was basified (pH-8) by using solid NaHCO$_3$, filtered through celite and washed with EtOAc (100 mL). The organic layer was separated, washed with brine solution (100 mL), dried over anhydrous Na$_2$SO$_4$ and evaporated under vacuum. The resulting crude material was purified by flash chromatgraphy (Biotage Isolera, eluent: 55% EtOAc in pet ether) to afford the isomer A and isomer B.

Isomer A analysis: Yield: 30% (2.2 g, pale yellow liquid). $^1$H NMR (400 MHz, CDCl$_3$): δ 7.45 (dd, J=7.6, 1.2 Hz, 1H), 7.29 (d, J=1.2 Hz, 1H), 7.21 (d, J=7.6 Hz, 1H), 3.05 (s, 2H), 2.56 (s, 3H), 1.50 (s, 6H). LCMS: (Method A) 191.0 (M+H), Rt 4.0 min, 98.4% (Max).

Isomer B analysis: Yield: 15% (500 mg, pale yellow liquid). $^1$H NMR (400 MHz, CDCl$_3$): δ 7.37 (d, J=8.0 Hz, 1H), 7.23 (t, J=8.0 Hz, 1H), 6.93 (d, J=8.0 Hz, 1H), 3.36 (s, 2H), 2.59 (s, 3H), 1.48 (s, 6H). LCMS: (Method A) 191.0 (M+H), Rt. 4.2 min, 99.2% (Max).

Step 5: 1-(2, 2-dimethyl-2, 3-dihydrobenzofuran-6-yl)ethan-1-ol

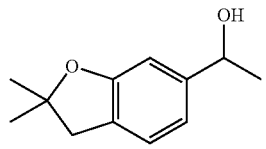

To a stirred solution of 1-(2, 2-dimethyl-2, 3-dihydrobenzofuran-6-yl)ethan-1-one (Isomer A, 2.1 g, 11.0 mmol) in methanol (11 mL) at 0° C., NaBH$_4$ (838 mg, 22.0 mmol) was added and the reaction mixture was stirred at RT for 60 min. After completion of the reaction (monitored by TLC), the mixture was quenched with ice-cold water (5 mL) and extracted with DCM (2×30 mL). The combined organic layer was washed with brine (20 mL), dried over Na$_2$SO$_4$ and concentrated under vacuum to afford the title compound. Yield: 76% (crude) (1.6 g, brown liquid). $^1$H NMR (400 MHz, CDCl$_3$): δ 7.28 (s, 1H), 7.12 (d, J=7.6 Hz, 1H), 6.85 (d, J=1.2 Hz, 1H), 4.88-4.83 (m, 1H), 3.01 (s 2H), 1.50-1.48 (m, 9H). LCMS: (Method A) 175.0 (M+H), Rt. 3.5 min, 96.9% (Max).

Step 6: 6-(1-chloroethyl)-2, 2-dimethyl-2, 3-dihydrobenzofuran

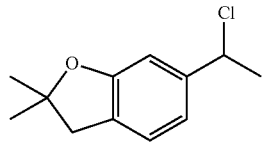

To a stirred solution of 1-(2, 2-dimethyl-2, 3-dihydrobenzofuran-6-yl)ethan-1-ol (1.6 g, 8.32 mmol) in DCM (10 mL), SOCl$_2$ (2.0 mL, 24.9 mmol) was added at 0° C. and the mixture was stirred at RT for 2 hr. After completion of the reaction (monitored by TLC), the mixture was then concentrated under vacuum to afford the title compound which was used in the next step without any further purification. Yield: 91% (1.75 g, pale brown gummy solid).

Intermediate 7: 1-(1-(2-methyl-2,3-dihydrobenzofuran-6-yl)ethyl)piperazine dihydrochloride

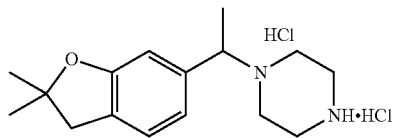

Step 1: tert-butyl 4-(1-(2-methyl-2,3-dihydrobenzofuran-6-yl)ethyl)piperazine-1-carboxylate

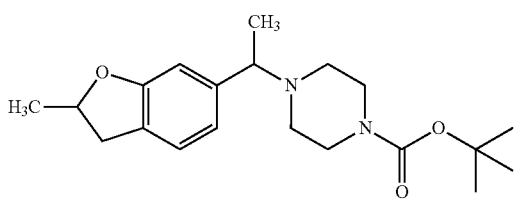 [SMILES: CC1Cc2ccc(C(C)N3CCN(C(=O)OC(C)(C)C)CC3)cc2O1]

To a stirred solution of 1-Boc-piperazine (658 mg, 11.7 mmol) in DMF (3 mL), intermediate 1 (580 mg, 2.9 mmol) and TEA (1.60 mL, 11.7 mmol) were added and the reaction mixture was heated at 70° C. overnight. Completion of the reaction was monitored by TLC, then the reaction mixture was evaporated under vacuum. To the resulting mixture, water (5 mL) was added and the aqueous layer was extracted with EtOAc (2×15 mL). The combined organic layer was dried over anhydrous $Na_2SO_4$, filtered and concentrated under vacuum. The resulting crude material was purified by flash chromatography (Biotage Isolera, eluent: 35% EtOAc in pet ether) to afford the title compound. Yield: 31% (250 mg, pale brown gum). $^1$H NMR (400 MHz, $CDCl_3$): δ 7.06 (d, J=7.6 Hz, 1H), 6.75 (d, J=8.0 Hz, 1H), 6.70 (s, 1H), 4.96-4.92 (m, 1H), 3.47-3.27 (m, 5H), 2.86-2.82 (m, 1H), 2.45-2.42 (m, 5H), 1.47-1.42 (m, 12H), 1.36 (d, J=6.4 Hz, 3H). LCMS: (Method A) 347.3 (M+H), Rt. 3.7 min, 63.4% (Max).

Step 2: 1-(1-(2-methyl-2, 3-dihydrobenzofuran-6-yl)ethyl)piperazine dihydrochloride

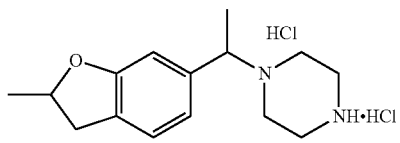

To a stirred solution of tert-butyl 4-(1-(2-methyl-2,3-dihydrobenzofuran-6-yl)ethyl)piperazine-1-carboxylate (250 mg, 0.08 mmol) in dry 1, 4 dioxane (5 mL), HCl solution in dioxane (10 mL, 4M) was added at 0° C. dropwise and the reaction mixture was stirred at RT for 2 h. After completion of the reaction (monitored by TLC), the mixture was concentrated under vacuum to afford the tittle compound. Yield: 93% (600 mg, off white solid). $^1$H NMR (400 MHz, DMSO-$d_6$): 9.79-9.61 (m, 2H), 7.26 (d, J=7.6 Hz, 1H), 7.09-7.03 (m, 2H), 4.97-4.51 (m, 1H), 3.51 (q, J=6.6 Hz, 1H), 3.83-3.31 (m, 8H), 3.16-3.13 (m, 2H), 1.67 (d, J=6.6 Hz, 3H), 1.52 (d, J=6.4 Hz, 3H).

Intermediate 8: N-((2-chloropyrimidin-5-yl)(methyl)(oxo)-λ$^6$-sulfanylidene)-2,2,2-trifluoroacetamide

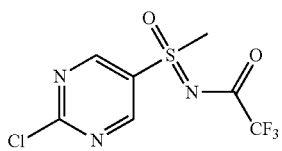 [SMILES: CS(=O)(=NC(=O)C(F)(F)F)c1cnc(Cl)nc1]

Step 1: 2-chloro-5-(methylthio)pyrimidine

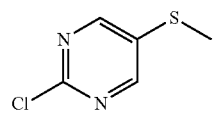

To a stirred solution of 5-bromo-2-chloropyrimidine (5 g, 25.8 mmol) and 1, 2-dimethyldisulfane (2.92 g, 31.02 mmol) in THF (15 mL), n-BuLi (16.0 mL, 25.8 mmol, 1.6 M in hexane) was added at -78° C. and stirred for 1 h under the same temperature. After completion of the reaction (monitored by TLC), the reaction was then quenched with the addition of sat.$NH_4Cl$ (15 mL) and the aqueous layer was extracted with EtOAc (50 mL). The organic layer was washed with water (10 mL), brine (10 mL) and dried over anhydrous $Na_2SO_4$. The resulting crude material was purified by flash chromatography (silica gel: 60-120 mesh, eluent: 15% EtOAc in pet ether) to afford the title compound. Yield: 13% (0.6 g, white solid). $^1$H NMR (400 MHz, $CDCl_3$): δ 8.50 (s, 2H), 2.56 (s, 3H). LCMS: (Method A) 161.1 (M+H), Rt. 2.1 min, 95.2% (Max). HPLC: (Method A) Rt. 2.4 min, 98.5% (Max).

Step 2: 2-chloro-5-(methylsulfinyl)pyrimidine

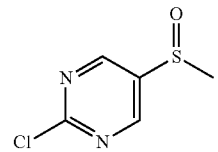

To a stirred solution of 2-chloro-5-(methylthio)pyrimidine (0.6 g, 2.49 mmol) in DCM (2 mL, 10 V), m-CPBA (0.644 g, 3.23 mmol) was added portion wise at 0° C. for 30 min. Completion of the reaction was monitored by TLC, the reaction mixture was then quenched with 10% $NaHCO_3$ solution and extracted with DCM (2×100 mL). The combined organic layer was washed with brine (30 mL), dried over anhydrous $Na_2SO_4$ and concentrated under vacuum. The resulting crude material was purified by flash chromatography (Biotage Isolera, eluent: 10-12% EtOAc in pet ether) to afford the title compound. Yield: 33% (330 mg, off white solid). $^1$H NMR (400 MHz, DMSO-$d_6$): δ 8.88 (s, 2H), 2.92 (s, 3H). LCMS: (Method A) 177.1 (M+H), Rt. 0.8 min, 99.1% (Max). HPLC: (Method A) Rt. 1.9 min, 99.6% (Max).

Step 3: N-((2-chloropyrimidin-5-yl) (methyl)(oxo)-λ$^6$-sulfanylidene)-2,2,2-trifluoroacetamide

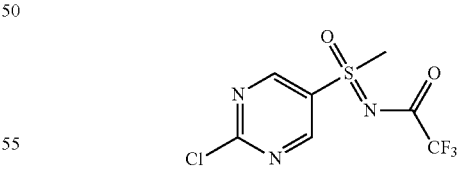

To a stirred solution of 2-chloro-5-(methylsulfinyl)pyrimidine (0.9 g, 5.09 mmol) in DCM (18.0 mL, 20 V), trifluoroacetamide (1.15 g, 10.19 mmol), MgO (0.8 g, 20.38 mmol), $Rh_2(OAc)_4$ (0.12 g, 0.25 mmol) and $PhI(OAC)_2$ (2.46 g, 7.64 mmol) were added and the reaction mixture was stirred at RT overnight. Completion of the reaction was monitored by TLC, the reaction mixture was then filtered through celite and the filtrate was concentrated under vacuum. The resulting crude material was purified by flash chromatography (Biotage Isolera, eluent: 16-18% EtOAc in pet ether) to afford the title compound. Yield: 74% (1.1 g, white solid). LCMS: (Method A) 288.0 (M+H), Rt. 3.8 min, 71.1% (Max).

Intermediate 9: 1-(1-((R)-2-methyl-2,3-dihydrobenzofuran-6-yl)ethyl)piperazine dihydrochloride

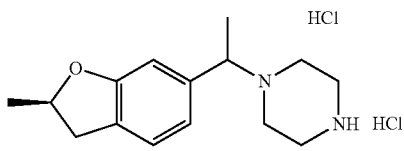 [SMILES: CC(c1ccc2c(c1)O[C@H](C)C2)N1CCNCC1 ; Cl ; Cl]

Step 1: tert-butyl 4-(1-((R)-2-methyl-2,3-dihydrobenzofuran-6-yl)ethyl)piperazine-1-carboxylate

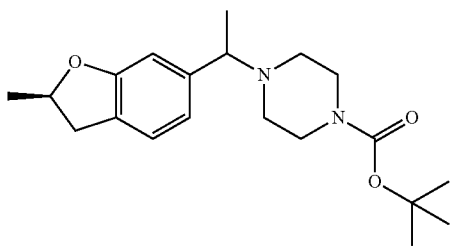 [SMILES: CC(c1ccc2c(c1)O[C@H](C)C2)N1CCN(C(=O)OC(C)(C)C)CC1]

To a stirred solution of 1-Boc-piperazine (3.18 g, 17.08 mmol) in DMF (5.6 mL), intermediate 4 (2.8 g, 14.23 mmol) followed by TEA (8.00 mL, 56.94 mmol) were added slowly at RT and the reaction mixture was heated at 80° C. overnight. Completion of the reaction was monitored by TLC, then the reaction mixture was evaporated under vacuum. To the resulting mixture, water (20 mL) was added and the aqueous layer was extracted with EtOAc (2×25 mL). The combined organic layer was washed with brine solution (10 mL), dried over anhydrous $Na_2SO_4$, filtered and concentrated under vacuum. The resulting crude material was purified by flash chromatography (Biotage Isolera, eluent: 12% EtOAc in pet ether) to afford the title compound. Yield: 71% (3.45 g, pale brown gummy liquid). $^1$H NMR (400 MHz, $CDCl_3$): δ 7.08 (d, J=7.6 Hz, 1H), 6.75 (t, J=7.6 Hz, 2H), 4.96-4.92 (m, 1H), 3.40-3.25 (m, 6H), 2.80 (dd, J=15.4, 8.4 Hz, 1H), 2.41-2.37 (m, 4H), 1.49-1.44 (m, 12H), 1.35 (d, J=6.4 Hz, 3H). LCMS: (Method A) 347.2 (M+H), Rt 2.37 min, 81.0% (Max).

Step 2: 1-(1-((R)-2-methyl-2,3-dihydrobenzofuran-6-yl)ethyl)piperazine dihydrochloride

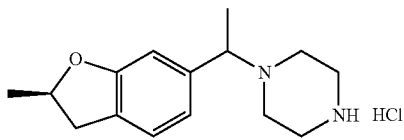 [SMILES: CC(c1ccc2c(c1)O[C@H](C)C2)N1CCNCC1 ; Cl]

To a stirred solution of tert-butyl 4-(1-((R)-2-methyl-2,3-dihydrobenzofuran-6-yl)ethyl)piperazine-1-carboxylate (3.4 g, 9.82 mmol) in dry 1, 4-dioxane (10 mL), HCl solution in dioxane (17 mL, 4M) was added dropwise at 0° C. and the reaction mixture was stirred at RT for 2 h. After completion of the reaction (monitored by TLC), the mixture was concentrated under vacuum and the resulting crude material was triturated with EtOAc to afford the tittle compound. Yield: 94% (2.9 g, pale brown solid). $^1$H NMR (400 MHz, DMSO-$d_6$): δ 7.27 (d, J=7.6 Hz, 1H), 7.08 (q, J=4.4 Hz, 2H), 4.97-4.91 (m, 1H), 4.52 (s, 1H), 3.86-3.84 (m, 1H), 3.65-3.60 (m, 4H), 3.57 (m, 1H), 3.49-3.30 (m, 4H), 2.81-2.77 (m, 1H) 1.70 (d, J=6.4 Hz, 3H), 1.40 (d, J=6.4 Hz, 3H). LCMS: (Method A) 247.2 (M+H), Rt 1.7 min, 81.7% (Max).

Intermediate 10: 1-(1-(2,2-di methyl-2,3-dihydrobenzofuran-6-yl)ethyl)piperazine dihydrochloride

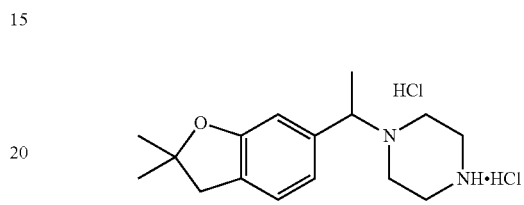

Step 1: tert-butyl 4-(1-(2, 2-dimethyl-2, 3-dihydrobenzofuran-6-yl)ethyl)piperazine-1-carboxylate

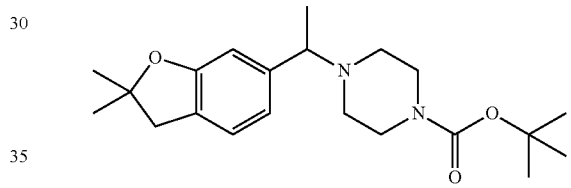

To a stirred solution of 1-boc-piperazine (960 mg, 22.19 mmol) in DMF (3 mL), intermediate 6 (900 mg, 4.21 mmol) was added and the reaction mixture was heated at 70° C. overnight. Completion of the reaction was monitored by TLC, then the reaction mixture was evaporated under vacuum. To the resulting mixture, water (5 mL) was added and the aqueous layer was extracted with EtOAc (2×15 mL). The combined organic layer was dried over anhydrous $Na_2SO_4$, filtered and concentrated under vacuum. The resulting crude material was purified by flash chromatography (Biotage Isolera, eluent: 35% EtOAc in pet ether) to afford the title compound. Yield: 46% (700 mg, pale brown gummy solid). $^1$H NMR (400 MHz, $CDCl_3$): δ 7.06 (d, J=7.6 Hz, 1H), 6.75 (q, J=8.0 Hz, 1H), 6.70 (s, 1H), 3.47-3.32 (m, 4H), 2.99 (s, 2H), 2.86-2.85 (m, 2H), 2.45-2.44 (m, 2H), 1.47-1.35 (m, 15H). 1.36 (d, J=6.4 Hz, 3H). LCMS: (Method A) 361.0 (M+H), Rt. 3.7 min, 63.4% (Max).

Step 2: 1-(1-(2,2-dimethyl-2, 3-dihydrobenzofuran-6-yl)ethyl)piperazine dihydrochloride

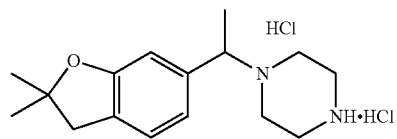

To a stirred solution of tert-butyl 4-(1-(2, 2-dimethyl-2, 3-dihydrobenzofuran-6-yl)ethyl)piperazine-1-carboxylate (700 mg, 1.94 mmol) in dry 1, 4 dioxane (5 mL), HCl solution in dioxane (4M, 10 mL) was added at 0° C. and stirred at RT for 2 h. Completion of the reaction was monitored by TLC, the reaction mixture was then concentrated under reduced pressure to afford the tittle compound. Yield: 93% (600 mg, off white solid). $^1$H NMR (400 MHz, CDCl$_3$): 12.3 (s, 1H), 9.64 (s, 2H), 7.26 (d, J=6.8 Hz, 1H), 7.05-7.04 (m, 2H), 4.50 (bs, 1H), 3.80-3.10 (m, 1H), 3.40-3.10 (m, 9H), 1.67 (s, 3H), 1.42-1.41 (m, 6H). LCMS: (Method A) 261.2 (M+H), Rt. 1.8 min, 82.2% (Max).

Example 1: N-(5-(4-(1-(2-methyl-2,3-dihydrobenzofuran-6-yl)ethyl)piperazin-1-yl)-1,3,4-thiadiazol-2-yl)acetamide

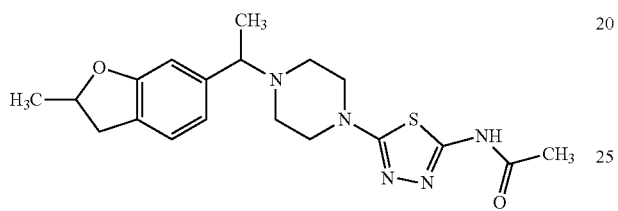

To a stirred solution of intermediate 1 (0.200 g, 1.01 mmol) in DMF (2.5 mL), TEA (0.5 mL, 4.1 mmol) and intermediate 2 (0.254 g, 1.1 mmol) were added at RT and the reaction mixture was heated at 70° C. overnight. Completion of reaction was monitored by TLC, then the reaction mixture was concentrated under vacuum. The resulting crude material was purified by flash chromatography (Biotage Isolera, eluent: 2-4% methanol in DCM) to afford the title compound. Yield: 10% (38.8 mg, pale brown solid). $^1$H NMR (400 MHz, CDCl$_3$): δ 7.12 (d, J=7.6 Hz, 1H), 6.75 (d, J=7.2 Hz, 1H), 6.68 (s, 1H), 4.89 (d, J=5.6 Hz, 1H), 3.34-3.31 (m, 4H), 3.24 (s, 1H), 2.78-2.76 (m, 2H), 2.51-2.43 (m, 4H), 2.10 (s, 3H), 1.39 (d, J=4.0 Hz, 3H), 1.28 (d, J=6.0 Hz, 3H). LCMS: (Method A) 388.3 (M+H), Rt. 2.6 min, 97.9% (Max). HPLC: (Method A) Rt. 2.6 min, 95.9% (Max).

Example 2: 2-(4-(1-(2-methyl-2,3-dihydrobenzofuran-6-yl)ethyl)piperazin-1-yl)-7,8-dihydropyrido[4,3-d]pyrimidin-5(6H)-one

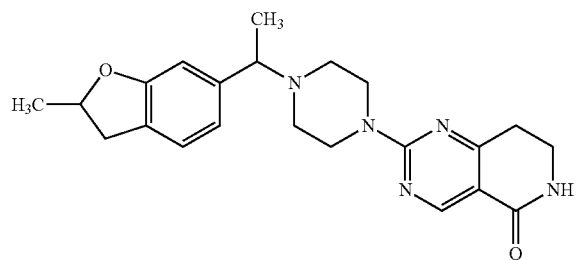 [SMILES: CC1Cc2ccc(C(C)N3CCN(c4ncc5c(n4)CCNC5=O)CC3)cc2O1]

To a stirred solution of 1-(2-methyl-2,3-dihydrobenzofuran-5-yl)ethan-1-ol (200 mg, 1.0 mmol, synthesis described in intermediate 1, steps 1 to 4) in DCM (10 mL), thionyl chloride (1 ml) was added dropwise at 0° C. and the reaction mixture was stirred at RT for 1 h. After completion of the reaction (monitored by TLC), the reaction mixture was evaporated under vacuum and co-distilled with DCM (2×10 mL). The resulting mixture was dissolved in DCM (10 ml) and was added to a mixture of intermediate 3 (288 g, 1.28 mmol) and TEA (54 mg, 5.3 mmol) in DCM (10 mL) drop wise at RT and the reaction mixture was stirred at RT overnight. Completion of the reaction was monitored by TLC, then the reaction mixture was evaporated under vacuum. The resulting crude material was purified by flash chromatography (Biotage Isolera, eluent: 75-80% EtOAc in pet ether) to afford the title compound. Yield: 25% (20 mg, pale brown solid). $^1$H NMR (400 MHz, DMSO-d$_6$): δ 8.58 (s, 1H), 7.69 (s, 1H), 7.11 (d, J=7.6 Hz, 1H), 6.75 (d, J=7.2 Hz, 1H), 6.68 (s, 1H), 4.89-4.87 (m, 1H), 3.80-3.79 (m, 4H), 3.38-3.24 (m, 5H), 2.80-2.67 (m, 4H), 2.46-2.43 (m, 1H), 2.37-2.33 (m, 1H), 1.39-1.37 (m, 3H), 1.28 (d, J=6.8 Hz, 3H). LCMS: (Method A) 394.5 (M+H), Rt. 2.6 min, 97.8% (Max). HPLC: (Method A) Rt. 2.6 min, 97.9% (Max).

Example 3: Imino(methyl)(2-(4-(1-(2-methyl-2,3-dihydrobenzofuran-6-yl)ethyl)piperazin-1-yl)pyrimidin-5-yl)-λ$^6$-sulfanone

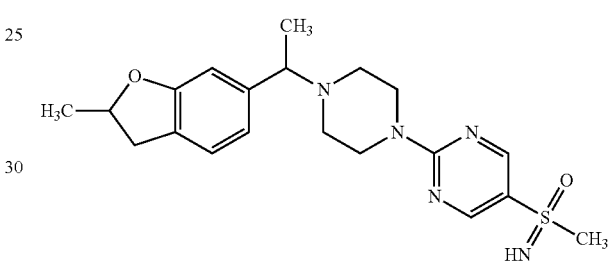

Step 1: Imino(methyl)(2-(4-(1-(2-methyl-2,3-dihydrobenzofuran-6-yl)ethyl)piperazin-1-yl)pyrimidin-5-yl)-λ$^6$-sulfanone

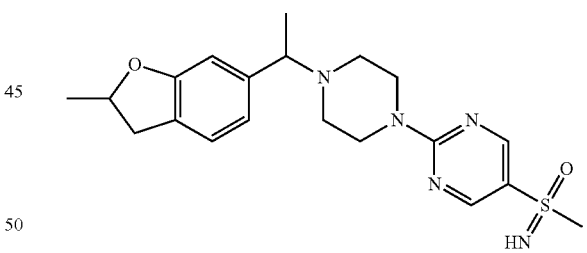

To a stirred solution of intermediate 7 (300 mg, 0.90 mmol) in DMF (2.5 mL), TEA (0.7 mL, 4.80 mmol) and intermediate 8 (300 mg, 1.2 mmol) were added at RT and stirred overnight. Completion of the reaction was monitored by TLC, then the reaction mixture was evaporated at 50° C. under vacuum. To the resulting mixture, water (5 mL) was added and the aqueous layer was extracted with EtOAc (2×50 mL). The combined organic layer was dried over Na$_2$SO$_4$ and concentrated under vacuum. The resulting crude material was purified by flash chromatography (silica gel: 230-400 mesh, eluent: 50% EtOAc in pet-ether) to obtain 2,2,2-trifluoro-N-(methyl(2-(4-(1-(2-methyl-2,3-dihydrobenzofuran-6-yl)ethyl)piperazin-1-yl)pyrimidin-5-yl)(oxo)-λ$^6$-sulfanylidene)acetamide. Yield: 30% (150 mg, off white solid).

To this intermediate methanol (7 mL, 20 V) and K₂CO₃ (414 mg, 4.53 mmol) were added, and the resulting mixture was stirred at RT for 20 min. After 20 min, the reaction mixture was filtered through celite and concentrated under vacuum. To the resulting mixture, water (20 mL) was added and the aqueous layer was extracted with DCM (2×100 mL). The combined organic layer was dried over anhydrous Na₂SO₄ and concentrated under vacuum. The resulting crude material was purified by flash chromatography (Biotage Isolera, gradient: 1-2% methanol in DCM) to afford the title compound. Yield: 20% (75 mg, off white solid). ¹H NMR (400 MHz, DMSO-d₆): δ 8.66 (s, 2H), 7.11 (d, J=7.6 Hz, 1H), 6.75 (d, J=7.6 Hz, 1H), 6.68 (s, 1H), 4.89-4.87 (m, 1H), 4.24 (s, 1H), 3.82-3.81 (m, 4H), 3.37-3.20 (m, 2H), 3.08 (s, 3H), 2.76-2.71 (m, 1H), 2.47-2.33 (m, 4H), 1.38 (q, J=2.4 Hz, 3H), 1.28 (d, J=6.4 Hz, 3H). LCMS: (Method A) 402.0 (M+H), Rt 2.4 min, 99.0% (Max). HPLC: (Method A) Rt 2.4 min, 98.3% (Max).

Example 4: N-(5-(4-(1-(2,2-dimethyl-2,3-dihydrobenzofuran-6-yl)ethyl)piperazin-1-yl)-1,3,4-thiadiazol-2-yl)acetamide

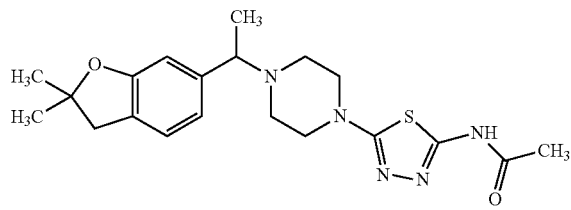 [SMILES: CC(=O)Nc1nnc(N2CCN(C(C)c3ccc4c(c3)OC(C)(C)C4)CC2)s1]

To a stirred solution of intermediate 2 (356 mg, 1.56 mmol) and TEA (0.8 ml mg, 5.6 mmol) in dry DMF (3 mL), intermediate 6 (300 mg, 1.4 mmol) was added and the reaction mixture was heated at 75° C. overnight. Completion of the reaction was monitored by TLC, then the reaction mixture was evaporated at 45° C. under vacuum. To the resulting mixture, water (4 mL) was added and the aqueous layer was extracted with EtOAc (3×20 mL). The combined organic layer was washed with brine solution (10 mL), dried over anhydrous Na₂SO₄ and concentrated under vacuum. The resulting crude material was purified by flash chromatography (Biotage Isolera, eluent: 4-5% methanol in DCM) to afford the title compound. Yield: 7% (39.4 mg, off white solid). ¹H NMR (400 MHz, DMSO-d₆): δ 12.00 (s, 1H), 7.09 (d, J=7.6 Hz, 1H), 6.73 (d, J=7.6 Hz, 1H), 6.63 (s, 1H), 3.37-3.33 (m, 4H), 2.96 (s, 2H), 2.50-2.35 (m, 4H), 2.09 (s, 3H), 1.40 (s, 3H), 1.39 (s, 3H), 1.27 (d, J=6.4 Hz, 3H). LCMS: (Method A) 402.0 (M+H), Rt. 2.8 min, 94.7% (Max). HPLC: (Method A) Rt 2.7 min, 96.3% (Max).

Example 5: (2-(4-(1-(2,2-dimethyl-2,3-dihydrobenzofuran-6-yl)ethyl)piperazin-1-yl)pyrimidin-5-yl)(imino)(methyl)-λ⁶-sulfanone

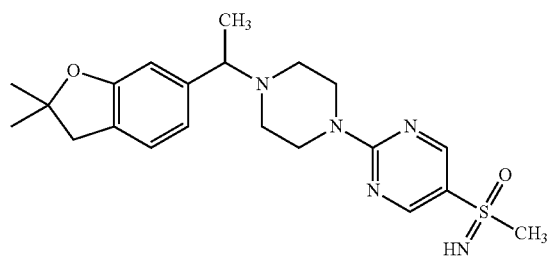

To a stirred solution of Intermediate 10 (400 mg, 1.20 mmol) in DMF (2.5 mL), TEA (0.7 mL, 4.80 mmol) and intermediate 8 (344 mg, 1.20 mmol, synthesis described in example 3, steps 1 to 5) were added at RT and the reaction mixture was stirred overnight. Completion of the reaction was monitored by TLC, then the reaction mixture was evaporated at 50° C. under reduced pressure. To the resulting mixture, water (2 mL) was added and the aqueous layer was extracted with EtOAc (2×50 mL). The combined organic layer was dried over anhydrous Na₂SO₄ and concentrated under vacuum. The resulting crude material was purified by flash chromatography (silica gel: 230-400 mesh, eluent: 50% EtOAc in pet-ether) to obtain N-((2-(4-(1-(2,2-dimethyl-2,3-dihydrobenzofuran-6-yl)ethyl)piperazin-1-yl)pyrimidin-5-yl)(methyl)(oxo)-λ⁶-sulfanylidene)-2,2,2-trifluoroacetamide. Yield: 23% (180 mg, off white solid). To this intermediate methanol (7 mL, 20 V) and K₂CO₃ (414 mg, 4.53 mmol) were added and stirred for 20 min. After 20 min, the reaction mixture was filtered through celite and concentrated under vacuum. To the resulting mixture, water (20 mL) was added and the aqueous layer was extracted with DCM (2×100 mL). The combined organic layer was dried over anhydrous Na₂SO₄ and concentrated under vacuum. The resulting crude material was purified by flash chromatography (Biotage Isolera, gradient: 1-2% methanol in DCM) to afford the title compound. Yield: 18% (83.6 mg, off white solid). ¹H NMR (400 MHz, DMSO-d₆): δ 8.66 (s, 2H), 7.10 (d, J=7.6 Hz, 1H), 6.74 (d, J=7.6 Hz, 1H), 6.65 (s, 1H), 4.24 (s, 1H), 3.82 (s, 4H), 3.38 (t, J=6.8 Hz, 1H), 3.08 (s, 3H), 2.96 (s, 2H), 2.39-2.33 (m, 4H), 1.41-1.39 (m, 6H), 1.29 (d, J=6.8 Hz, 3H). LCMS: (Method A) 416.0 (M+H), Rt. 2.6 min, 99.6% (Max). HPLC: (Method A) Rt 2.5 min, 99.8% (Max).

Example 6: 2-(4-(1-(2,2-dimethyl-2,3-dihydrobenzofuran-6-yl)ethyl)piperazin-1-yl)-7,8-dihydropyrido[4,3-d]pyrimidin-5(6H)-one

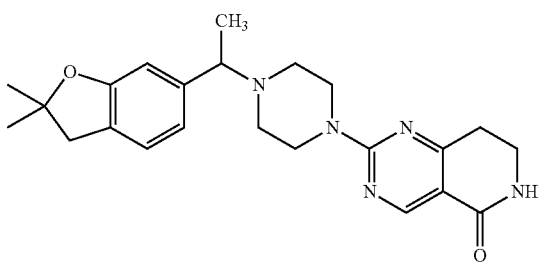 [SMILES: CC(c1ccc2c(c1)OC(C)(C)C2)N1CCN(c2ncc3c(n2)CCNC3=O)CC1]

To a stirred solution of intermediate 6 (300 mg, 1.4 mmol) in dry DMF (3 mL), TEA (0.8 mL, 5.6 mmol) and intermediate 3 (330 mg, 1.7 mmol) were added and the reaction mixture was heated at 75° C. overnight. Completion of the reaction was monitored by TLC, then the reaction mixture was evaporated at 45° C. under vacuum. To the resulting mixture, water (4 mL) was added and the aqueous layer was extracted with EtOAc (3×20 mL). The combined organic layer was washed with brine solution (10 mL), dried over anhydrous Na₂SO₄ and concentrated under vacuum. The resulting crude material was purified by flash chromatography (Biotage Isolera, eluent: 4-5% methanol in DCM) to afford the title compound. Yield: 22% (116.19 mg, off white solid). ¹H NMR (400 MHz, DMSO-d₆): δ 8.58 (s, 1H), 7.70 (s, 1H), 7.10 (d, J=7.6 Hz, 1H), 6.74 (d, J=7.2 Hz, 1H), 6.65 (s, 1H), 3.80-3.79 (s, 4H), 3.37-3.36 (m, 3H), 2.96 (s, 2H), 2.80-2.77 (t, J=6.8 Hz, 2H), 2.37-2.34 (m, 4H), 1.40 (d, J=2.8 Hz, 6H), 1.28 (d, J=6.8 Hz, 3H). LCMS: (Method A) 408.0 (M+H), Rt. 2.8 min, 98.5% (Max). HPLC: (Method A) Rt 2.7 min, 98.9% (Max).

Example 7: 1-(1-(2-methyl-2,3-dihydrobenzofuran-6-yl)ethyl)-4-(4-(methylsulfonyl)phenyl)piperazine

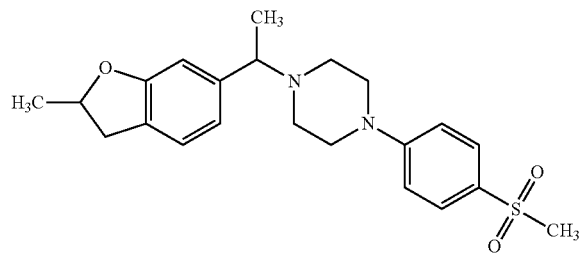

Step 1: tert-butyl 4-(4-(methylsulfonyl)phenyl)piperazine-1-carboxylate

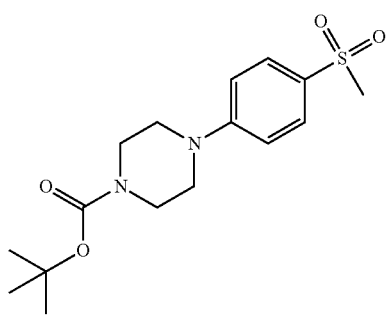 [SMILES: CC(C)(C)OC(=O)N1CCN(c2ccc(S(C)(=O)=O)cc2)CC1]

To a stirred solution of 1-fluoro-4-(methylsulfonyl)benzene (0.3 g, 1.7 mmol) in DMF (3 mL), N-Boc-piperazine (420 mg, 2.24 mmol) and TEA (1.0 ml, 6.86 mmol) were added at RT and the reaction mixture was heated at 80° C. for 12 h. Completion of the reaction was monitored by TLC, then the reaction mixture was concentrated under vacuum. The resulting crude material was purified by flash chromatography (Biotage Isolera, eluent: 50% EtOAc in pet-ether) to afford the title compound. Yield: 43% (0.7 g, pale yellow colored solid). ¹H NMR (400 MHz, DMSO-d₆): δ 7.00 (d, J=8.8 Hz, 2H), 6.82 (d, J=9.2 Hz, 2H), 3.64 (t, J=4.8 Hz, 4H), 3.37 (t, J=4.8 Hz, 4H), 3.10 (s, 3H), 1.51 (s, 9H). LCMS: (Method A) 285.2 (M+H-tBu), Rt. 4.1 min, 51.9% (Max).

Step 2: 1-(4-(methylsulfonyl)phenyl)piperazine hydrochloride

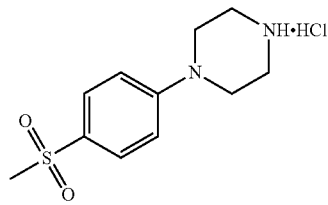

To a stirred solution of tert-butyl 4-(4-(methylsulfonyl)phenyl)piperazine-1-carboxylate (0.6 g, 1.7 mmol) in dry 1,4-dioxane (6 mL, 10 V) at 0° C., HCl solution in dioxane (2.2 mL, 4M) was added dropwise and the reaction mixture was stirred at RT for 10 min. Completion of the reaction was monitored by TLC, then the reaction mixture was concentrated under vacuum. The resulting crude material was triturated with EtOAc and evaporated under vacuum to afford the title compound. Yield: 46% (0.25 g, off white solid). ¹H NMR (400 MHz, DMSO-d₆): δ 7.01 (d, J=16.0 Hz, 2H), 6.82 (d, J=8.0 Hz, 2H), 3.64 (t, J=4.8 Hz, 4H), 3.37 (t, J=4.8 Hz, 4H), 3.10 (s, 3H), 1.8 (s, 1H).

Step 3: 1-(1-(2-methyl-2, 3-dihydrobenzofuran-6-yl)ethyl)-4-4-(methylsulfonyl)phenyl)piperazine

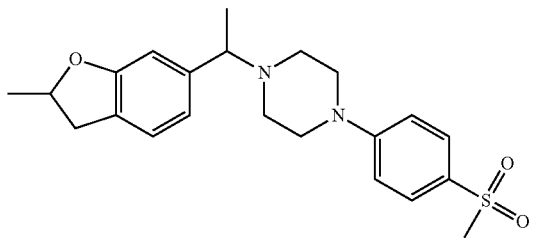 [SMILES: CC1Cc2ccc(C(C)N3CCN(c4ccc(S(C)(=O)=O)cc4)CC3)cc2O1]

To a stirred solution of 1-(4-(methylsulfonyl)phenyl)piperazine hydrochloride (0.22 g, 0.7 mmol) in DMF (2.5 mL), TEA (0.5 mL, 2.8 mmol) and intermediate 1 (0.17 g, 0.84 mmol) were added at RT and the reaction mixture was heated at 70° C. overnight. Completion of the reaction was monitored by TLC, then the reaction mixture was concentrated under vacuum. The resulting crude material was purified by flash chromatography (Biotage Isolera, eluent: 1-3% methanol in DCM) and the obtained material was further purified by prep HPLC (method B) to afford the title compound. Yield: 9% (20 mg, off white solid). ¹H NMR (400 MHz, DMSO-d₆): δ 7.66 (d, J=8.8 Hz, 2H), 7.12 (d, J=7.6 Hz, 1H), 7.04 (d, J=9.2 Hz, 2H), 6.75 (d, J=7.6 Hz, 1H), 6.68 (s, 1H), 4.89 (q, J=1.6 Hz, 1H), 3.36-3.24 (m, 6H), 3.08 (s, 3H), 2.75 (q, J=8.0 Hz, 1H), 2.43-2.33 (m, 4H), 1.38 (q, J=2.4 Hz, 3H), 1.29 (d, J=6.40 Hz, 3H). LCMS: (Method A) 401.0 (M+H), Rt. 2.9 min, 99.7% (Max). HPLC: (Method A) Rt. 2.9 min, 99.8% (Max).

Example 8: N-(5-(4-(1-(2-methyl-2,3-dihydrofuro[3,2-b]pyridin-6-yl)ethyl)piperazin-1-yl)-1,3,4-thiadiazol-2-yl)acetamide

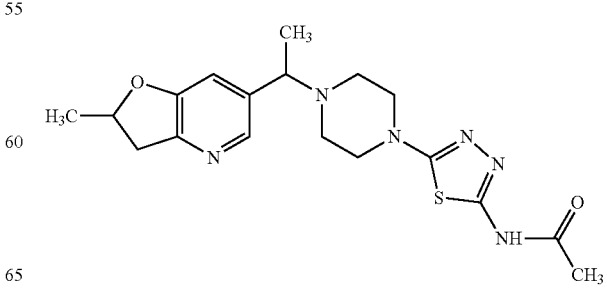

Step 1: methyl 6-chloro-5-hydroxynicotinate

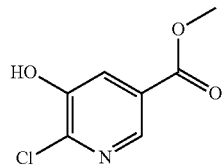

To a stirred solution of methyl-5-hydroxy nicotinate (10 g, 65.3 mmol, Combi blocks), 40% sodium hypochlorite solution (70 mL, 7V) was added at 0° C. for 2 h. Completion of the reaction was monitored by TLC, then 2N HCl solution (50 mL, 5V) was added slowly to the reaction mixture. The obtained white precipitate was collected by filtration and dried well under vacuum to afford the title compound. Yield: 42% (5.1 g, off white solid). $^1$H NMR (400 MHz, DMSO-$d_6$): δ 8.38 (s, 1H), 7.77 (s, 1H), 3.89 (s, 3H). LCMS: (Method A) 188.2 (M+H), Rt. 2.3 min, 63.1% (Max).

Step 2: methyl 2-methylfuro[3,2-b]pyridine-6-carboxylate

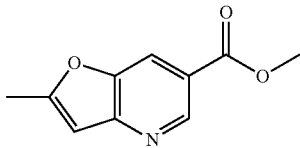

To a degassed solution of methyl 6-chloro-5-hydroxynicotinate (5.1 g, 27.4 mmol) in DMF, Pd(dppf)Cl$_2$ (1.1 g, 1.37 mmol), CuI (0.52 g, 2.74 mmol), TEA (7.6 mL, 54.8 mmol) and followed by propargyl trimethylsilane (6.2 mL, 41.1 mmol) were added at RT and the reaction mixture was stirred at 60° C. overnight. Completion of the reaction was monitored by TLC, then the reaction mixture was filtered through celite and DMF was concentrated to dryness under vacuum. The resulting crude material was purified by flash chromatography (Biotage Isolera, eluent: 15-25% EtOAc in pet ether) to afford the title compound. Yield: 46% (2.4 g, brown solid). $^1$H NMR (400 MHz, DMSO-$d_6$): δ 8.99 (s, 1H), 8.37 (s, 1H), 6.92 (s, 1H), 3.90 (s, 3H), 2.51 (s, 3H). LCMS: (Method A) 192.0 (M+H), Rt. 2.1 min, 96.9% (Max).

Step 3: 2-methyl-2,3-dihydrofuro[3,2-b]pyridin-6-yl)methanol

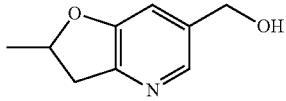

To a stirred solution of methyl 2-methylfuro[3,2-b]pyridine-6-carboxylate (2.4 g, 12.5 mmol) in THF, LAH (15.1 mL, 15.07 mmol, 1M in THF) was added at −10° C. dropwise and the reaction mixture was stirred at RT for 1 h. Completion of the reaction was monitored by TLC, then the reaction mixture was quenched with saturated NH$_4$Cl solution (15 mL) and the aqueous layer was extracted with EtOAc (2×40 mL). The combined organic layer was washed with brine solution (10 mL), dried over anhydrous Na$_2$SO$_4$ and evaporated under vacuum. The resulting crude material was purified by flash chromatography (Biotage Isolera, eluent: 2-4% methanol in DCM) to afford the title compound. Yield: 55% (1.1 g, brown gummy oil). $^1$H NMR (400 MHz, DMSO-$d_6$): δ 8.55 (s, 1H), 8.33 (s, 1H), 5.34 (t, J=7.6 Hz, 1H), 5.11-5.00 (m, 1H), 4.61 (d, J=7.2 Hz, 2H), 3.54-3.47 (m, 1H), 3.02-2.96 (m, 1H), 1.46 (d, J=6.0 Hz, 3H). LCMS: (Method B) 166.0 (M+H), Rt. 2.5 min, 45.1% (Max).

Step 4: 2-methyl-2,3-dihydrofuro[3,2-b]pyridine-6-carbaldehyde

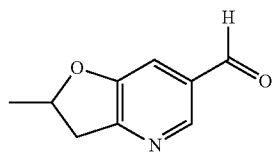

To a stirred solution of 2-methyl-2,3-dihydrofuro[3,2-b]pyridin-6-yl)methanol (1.1 g, 6.74 mmol) in DCM, dess-martin periodinane (4.3 g, 10.1 mmol) was added slowly at 0° C. and the reaction mixture was stirred at RT for 1 h. Completion of the reaction was monitored by TLC, then the reaction mixture was quenched with saturated NaHCO$_3$ solution (10 mL) and the aqueous layer was extracted with DCM (2×30 mL). The combined organic layer was washed with brine solution (10 mL), dried over anhydrous Na$_2$SO$_4$ and evaporated under vacuum. The resulting crude material was purified by flash chromatography (Biotage Isolera, eluent: 30% EtOAc in pet ether) to afford the title compound. Yield: 15% (0.15 g, pale yellow solid). $^1$H NMR (400 MHz, DMSO-$d_6$): δ 10.02 (s, 1H), 8.55 (s, 1H), 8.33 (s, 1H), 5.11-5.00 (m, 1H), 3.54-3.47 (m, 1H), 3.02-2.96 (m, 1H), 1.46 (d, J=6.0 Hz, 3H). LCMS: (Method B) 164.0 (M+H), Rt. 3.9 min, 42.9% (Max).

Step 5: 1-(2-methyl-2,3-dihydrofuro[3,2-b]pyridin-6-yl) ethan-1-ol

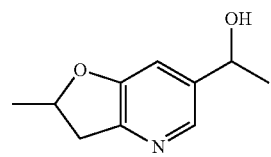

To the stirred solution of 2-methyl-2,3-dihydrofuro[3,2-b]pyridine-6-carbaldehyde (0.15 g, 0.86 mmol) in THF, methyl magnesium chloride (0.5 mL, 1.30 mmol, 3M solution in THF) was added dropwise at 0° C. and the reaction mixture was stirred at RT for 1 h. Completion of the reaction was monitored by TLC, then the reaction mixture was quenched with saturated NH$_4$Cl solution (3 mL) and the aqueous layer was extracted with EtOAc (2×15 mL). The combined organic layer was washed with brine solution (5 mL), dried over anhydrous Na$_2$SO$_4$ and evaporated under vacuum. The resulting crude material was forwarded as such to the next step without any further purification. Yield: 35%

(0.05 g, yellow gummy oil). ¹H NMR (400 MHz, DMSO-d₆): δ 8.41 (s, 1H), 7.81 (s, 1H), 5.35 (d, J=4.4 Hz, 1H), 5.00-4.89 (m, 1H), 3.54-3.47 (m, 1H), 3.39-3.29 (m, 1H), 3.02-2.96 (m, 1H), 1.43 (d, J=8.0 Hz, 3H), 1.31 (d, J=6.4 Hz, 3H). LCMS: (Method A) 180.0 (M+H), Rt. 1.2 min, 54.3% (Max).

Step 6: 6-(1-chloroethyl)-2-methyl-2, 3-dihydrofuro[3,2-b]pyridine

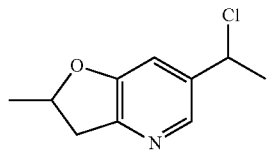

To a stirred solution of 1-(2-methyl-2,3-dihydrofuro[3,2-b]pyridin-6-yl)ethan-1-ol (0.05 g, 0.27 mmol) in DCM, thionyl chloride (0.1 mL, 0.55 mmol) was added dropwise at 0° C. and the reaction mixture was stirred at RT for 1 h. Completion of the reaction was monitored by TLC, then the reaction mixture was evaporated under vacuum to afford the title compound. Yield: 97% (0.05 g, brown gummy oil). ¹H NMR (400 MHz, DMSO-d₆): δ 8.61 (s, 1H), 8.10 (s, 1H), 5.40-5.34 (m, 1H), 5.09-4.97 (m, 1H), 3.54-3.47 (m, 1H), 3.02-2.96 (m, 1H), 1.44 (d, J=7.2 Hz, 3H), 1.23 (d, J=7.2 Hz, 3H). LCMS: (Method A) 198.2 (M+H), Rt. 2.4 min, 45.9% (Max).

Step 7: N-(5-(4-(1-(2-methyl-2, 3-dihydrofuro[3,2-b]pyridin-6-yl)ethyl)piperazin-1-yl)-1,3, 4-thiadiazol-2-yl)acetamide

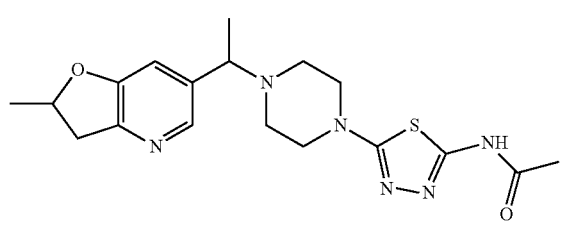 [SMILES: CC(=O)Nc1nnc(N2CCN(C(C)c3cnc4c(c3)OC(C)C4)CC2)s1]

To a stirred solution of intermediate 2 (0.17 g, 0.50 mmol) in DMF, TEA (0.18 mL, 1.26 mmol) followed by 6-(1-chloroethyl)-2-methyl-2,3-dihydrofuro[3,2-b]pyridine (0.05 g, 0.25 mmol) were added at RT and the reaction mixture was stirred at 70° C. overnight. Completion of the reaction was monitored by TLC, then the reaction mixture was evaporated under vacuum. To the resulting mixture, water (2 mL) was added and the aqueous layer was extracted with EtOAc (2×15 mL). The combined organic layer was washed with brine solution (10 mL), dried over anhydrous Na₂SO₄ and evaporated under vacuum. The resulting crude material was purified by flash chromatography (Biotage Isolera, gradient: 0-5% methanol in DCM), then the obtained material was further purified by Prep-HPLC (Method B) to afford the title compound. Yield: 3% (0.002 g, off white solid). ¹H NMR (400 MHz, CDCl₃): δ 7.98 (s, 1H), 7.19 (s, 1H), 5.07-5.05 (m, 1H), 3.70-3.65 (m, 4H), 3.49-3.43 (m, 1H), 3.30-3.18 (m, 1H), 2.99-2.93 (m, 1H), 2.77-2.74 (m, 4H), 2.34 (s, 3H), 1.55 (d, J=3.6 Hz, 3H), 1.27 (d, J=5.2 Hz, 3H). LCMS: (Method A) 389.0 (M+H), Rt. 1.8 min, 90.2% (Max). HPLC: (Method A) Rt. 1.7 min, 90.9% (Max).

Example 9: N-(5-(4-(1-((R)-2-methyl-2,3-dihydrobenzofuran-6-yl)ethyl)piperazin-1-yl)-1,3,4-thiadiazol-2-yl)acetamide

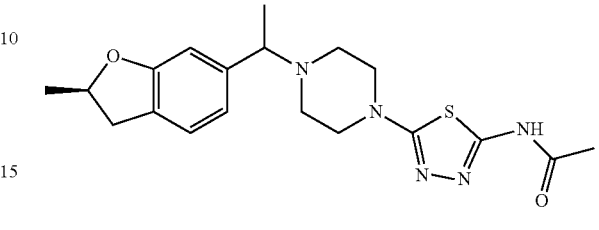

To a stirred solution intermediate 4 (0.5 g, 0.25 mmol) in DMF (2.5 mL), TEA (1.5 mL, 10.76 mmol) and intermediate 2 (0.64 g, 0.27 mmol) were added at RT and the reaction mixture was heated at 70° C. overnight. After completion of the reaction (monitored by TLC), the mixture was concentrated under vacuum and the resulting crude material was purified by flash chromatography (Biotage Isolera, gradient: 4-8% methanol in DCM) to afford the title compound. Yield: 11% (70 mg, off white solid). ¹H NMR (400 MHz, DMSO-d₆): δ 12.02 (s, 1H), 7.11 (d, J=7.2 Hz, 1H), 6.74 (d, J=7.2 Hz, 1H), 6.67 (s, 1H), 4.89 (t, J=6.0 Hz, 1H), 3.38-3.24 (m, 6H), 2.74 (q, J=7.6 Hz, 1H), 2.43-2.40 (m, 4H), 2.10 (s, 3H), 1.38 (t, J=2.0 Hz, 3H), 1.26 (t, J=6.8 Hz, 3H). LCMS: (Method A) 388.3 (M+H), Rt 2.5 min 99.9% (Max). HPLC: (Method A) Rt. 2.6 min, 99.8% (Max).

Example 10: 2-(4-(1-((R)-2-methyl-2,3-dihydrobenzofuran-6-yl)ethyl)piperazin-1-yl)-7,8-dihydropyrido[4,3-d]pyrimidin-5(6H)-one

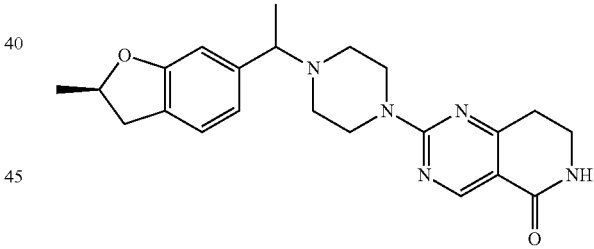

To a stirred solution of intermediate 3 (0.85 g, 0.27 mmol) in DMF (20 mL), TEA (1.5 mL, 10.76 mmol) and intermediate 4 (0.5 g, 0.25 mmol) were added at RT and the reaction mixture was heated at 80° C. overnight. Completion of the reaction was monitored by TLC, then the reaction mixture was evaporated under vacuum. To the resulting mixture, water (3 mL) was added and the aqueous layer was extracted with EtOAc (2×15 mL). The combined organic layer was washed with brine solution (10 mL), dried over anhydrous Na₂SO₄ and concentrated under vacuum. The resulting crude material was purified by flash chromatography (Biotage Isolera, gradient: 4-8% methanol in DCM) to afford the title compound. Yield: 18% (190 mg, off white solid). ¹H NMR (400 MHz, DMSO-d₆): δ 8.58 (d, J=2.8 Hz, 1H), 7.70 (s, 1H), 7.11 (d, J=7.6 Hz, 1H), 6.74 (d, J=7.6 Hz, 1H), 6.68 (s, 1H), 4.88 (q, J=8.0 Hz, 1H), 3.80 (m, 4H), 3.38-3.23 (m, 4H), 2.80-2.71 (m, 3H), 2.51-2.37 (m, 4H), 1.38 (q, J=2.8 Hz, 3H), 1.28 (d, J=6.4 Hz, 3H). LCMS: (Method A) 394.2 (M+H), Rt. 2.5 min, 99.9% (Max). HPLC: (Method A), Rt 2.6 min, 99.8% (Max).

Examples 11 and 12: N-(5-(4-((R)-1-((R)-2-methyl-2,3-dihydrobenzofuran-6-yl)ethyl)piperazin-1-yl)-1,3,4-thiadiazol-2-yl)acetamide and N-(5-(4-((S)-1-((R)-2-methyl-2,3-dihydrobenzofuran-6-yl)ethyl)piperazin-1-yl)-1,3,4-thiadiazol-2-yl)acetamide

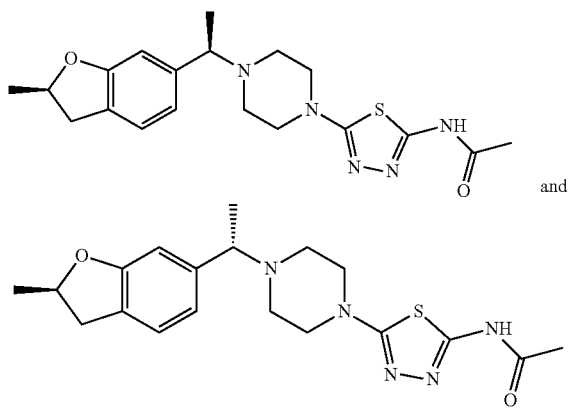

and

The enantiomers of example 9 was separated by SFC; mobile phase: 20 mM ammonia in methanol, column: LUX C3 (Method A), the first eluting peak was concentrated to afford the example 11 and the second eluting peak was concentrated to afford the example 12.

Analysis of first eluting fraction (example 11): Yield: 40% (30 mg, off white solid). $^1$H NMR (400 MHz, DMSO-d$_6$): δ 12.03 (s, 1H), 7.12 (d, J=7.6 Hz, 1H), 6.75 (d, J=7.6 Hz, 1H), 6.68 (s, 1H), 4.89 (q, J=6.4 Hz, 1H), 3.40-3.24 (m, 5H), 2.77-2.68 (m, 1H), 2.44-2.39 (m, 4H), 2.10 (s, 3H), 1.39 (d, J=6.0 Hz, 3H), 1.27 (t, J=6.4 Hz, 3H). LCMS: (Method A) 388.2 (M+H), Rt 2.5 min 99.2% (Max). HPLC: (Method A) Rt. 2.6 min, 99.8% (Max). Chiral SFC: (Method A) Rt. 3.8 min, 100% (Max).

Analysis of second eluting fraction (example 12): Yield: 45% (32 mg, off white solid). $^1$H NMR (400 MHz, DMSO-d$_6$): δ 12.03 (s, 1H), 7.12 (d, J=7.2 Hz, 1H), 6.75 (d, J=7.6 Hz, 1H), 6.68 (s, 1H), 4.90 (q, J=8.0 Hz, 1H), 3.40-3.24 (m, 5H), 2.77-2.68 (m, 1H), 2.42-2.34 (m, 4H), 2.09 (s, 3H), 1.38 (d, J=6.0 Hz, 3H), 1.27 (t, J=6.8 Hz, 3H). LCMS: (Method A) 388.3 (M+H), Rt. 2.5 min, 98.1% (Max). HPLC: (Method A) Rt. 2.6 min, 99.5% (Max). Chiral SFC: (Method A) Rt. 4.5 min, 99.3% (Max).

Example 13: 2-(4-((S)-1-((R)-2-methyl-2,3-dihydrobenzofuran-6-yl)ethyl)piperazin-1-yl)-7,8-dihydropyrido[4,3-d]pyrimidin-5(6H)-one or 2-(4-((R)-1-((R)-2-methyl-2,3-dihydrobenzofuran-6-yl)ethyl)piperazin-1-yl)-7,8-dihydropyrido[4,3-d]pyrimidin-5(6H)-one

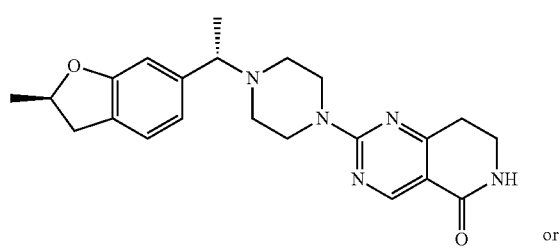

or

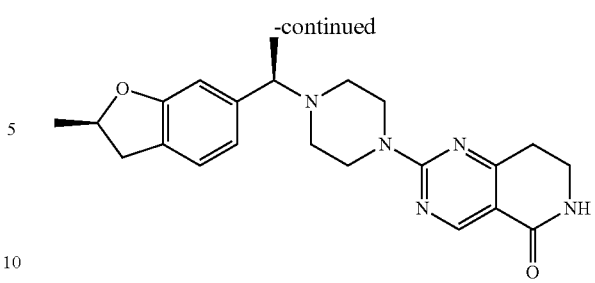

The enantiomers of example 10 was separated by SFC; mobile phase: 20 mM ammonia in methanol, column: LUX C3 (Method A), the first eluting fraction was concentrated to afford example 13.

Analysis of first eluting fraction (example 13): Yield: 40% (72 mg, off white solid). $^1$H NMR (400 MHz, DMSO-d$_6$): δ 8.58 (s, 1H), 7.69 (s, 1H), 7.10 (d, J=7.6 Hz, 1H), 6.74 (d, J=7.6 Hz, 1H), 6.68 (s, 1H), 4.88 (q, J=8.4 Hz, 1H), 3.80-3.75 (m, 4H), 3.38-3.17 (m, 4H), 2.80-2.77 (m, 3H), 2.43-2.34 (m, 4H), 1.38 (d, J=6.4 Hz, 3H), 1.28 (t, J=6.8 Hz, 3H). LCMS: (Method A) 394.2 (M+H), Rt 2.5 min, 99.9% (Max). HPLC: (Method A), Rt 2.6 min, 99.9% (Max). Chiral SFC: (Method A) Rt. 4.0 min, 8.5% (Max).

Example 14: N-(5-(4-(1-((S)-2-methyl-2,3-dihydrobenzofuran-6-yl)ethyl)piperazin-1-yl)-1,3,4-thiadiazol-2-yl)acetamide

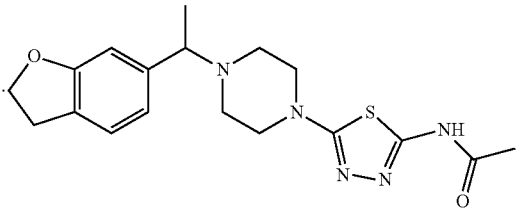

To a stirred solution of intermediate 5 (0.6 g, 0.03 mol) in DMF (6 mL), TEA (2 mL) and intermediate 2 (0.76 g, 0.03 mol) were added at RT and the reaction mixtue was heated at 70° C. overnight. Completion of the reaction was monitored by TLC, then the reaction mixture was concentrated under vacuum. To the resulting mixture, water (2 mL) was added and the aqueous layer was extracted with EtOAc (2×25 mL). The combined organic layer was washed with brine (10 mL), dried over anhydrous Na$_2$SO$_4$ and concentrated under vacuum. The resulting crude material was purified by flash chromatography (Biotage Isolera, eluent: 4-8% methanol in DCM) to afford the title compound. Yield: 13% (150 mg, off white solid). $^1$H NMR (400 MHz, DMSO-d$_6$): δ 12.02 (s, 1H), 7.11 (d, J=7.6 Hz, 1H), 6.75 (d, J=7.2 Hz, 1H), 6.67 (s, 1H), 4.90 (t, J=8.0 Hz, 1H), 3.38-3.24 (m, 5H), 2.77-2.71 (m, 1H), 2.51-2.43 (m, 4H), 2.10 (s, 3H), 1.38 (q, J=2.4 Hz, 3H), 1.28 (d, J=6.4 Hz, 3H). LCMS: (Method A) 388.1 (M+H), Rt 2.0 min, 97.9% (Max). HPLC: (Method A) Rt 2.5 min, 98.6% (Max). Chiral SFC: (Method B), Rt1. 3.8 min, 46.9%, Rt 2. 4.4 min, 53.1%.

Example 15: 2-(4-(1-((S)-2-methyl-2,3-dihydrobenzofuran-6-yl)ethyl)piperazin-1-yl)-7,8-dihydropyrido[4,3-d]pyrimidin-5(6H)-one

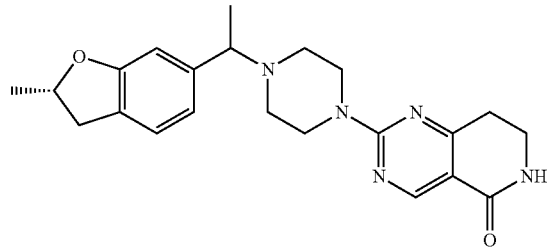 [SMILES: CC(c1ccc2c(c1)O[C@@H](C)C2)N1CCN(c2ncc3c(n2)CCNC3=O)CC1]

To a stirred solution of intermediate 3 (1.02 g, 3.35 mmol) in DMF (6 mL), intermediate 5 (0.6 g, 3.0 mmol) and TEA (2.0 mL) were added at RT and the reaction mixture was heated at 80° C. overnight. Completion of the reaction was monitored by TLC, then the reaction mixture was evaporated under vacuum. To the resulting mixture, water (10 mL) was added and the aqueous layer was extracted with EtOAc (2×25 mL). The combined organic layer was washed with brine solution (10 mL), dried over anhydrous $Na_2SO_4$ and concentrated under vacuum. The resulting crude material was purified by flash chromatography (Biotage Isolera, gradient: 4-8% methanol in DCM) to afford the title compound. Yield: 17% (200 mg, off white solid). $^1$H NMR (400 MHz, DMSO-$d_6$): δ 8.58 (s, 1H), 7.70 (s, 1H), 7.11 (d, J=7.2 Hz, 1H), 6.74 (d, J=7.6 Hz, 1H), 6.68 (s, 1H), 4.88 (d, J=6.4 Hz, 1H), 3.80-3.78 (m, 4H), 3.37-3.24 (m, 4H), 2.80-2.68 (m, 3H), 2.51-2.34 (m, 4H), 1.38 (d, J=6.0 Hz, 3H), 1.28 (d, J=6.4 Hz, 3H). LCMS: (Method A) 394.2 (M+H), Rt 2.0 min, 98.9% (Max). HPLC: (Method A), Rt 2.5 min, 98.7% (Max). Chiral SFC: (Method C), Rt 1. 2.2 min, 49.8% and Rt 2. 2.8 min, 49.4%.

Examples 16 and 17: N-(5-(4-((R)-1-((S)-2-methyl-2,3-dihydrobenzofuran-6-yl)ethyl)piperazin-1-yl)-1,3,4-thiadiazol-2-yl)acetamide and N-(5-(4-((S)-1-((S)-2-methyl-2,3-dihydrobenzofuran-6-yl)ethyl)piperazin-1-yl)-1,3,4-thiadiazol-2-yl)acetamide

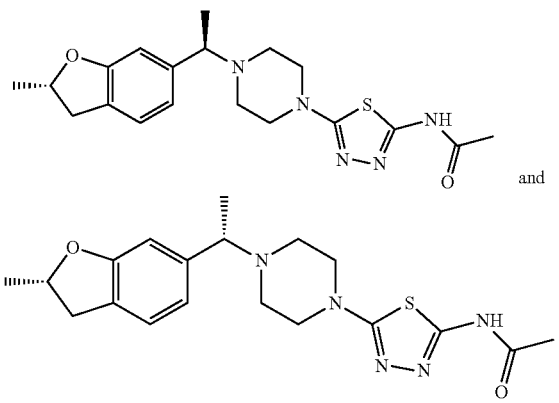

The enantiomers of this racemic example 14 was separated by SFC; mobile phase: 0.5% isopropyl amine in methanol; column: Chiracel OD-H (Method B), the first eluting fraction was concentrated to afford example 16 and second eluting fraction was concentrated to afford example 17.

Analysis of first eluting fraction (example 16): Yield: 35% (35 mg, off white solid). $^1$H NMR (400 MHz, DMSO-$d_6$): δ 12.02 (s, 1H), 7.11 (d, J=7.6 Hz, 1H), 6.64 (d, J=7.6 Hz, 1H), 6.67 (s, 1H), 4.89 (q, J=7.2 Hz, 1H), 3.38-3.34 (m, 5H), 3.30-3.25 (m, 1H), 2.80-2.30 (m, 1H), 2.43-2.41 (m, 4H), 2.10 (s, 3H), 1.38 (d, J=6.4 Hz, 3H), 1.28 (d, J=6.4 Hz, 3H). LCMS: (Method A) 388.1 (M+H), Rt 2.1 min, 99.1% (Max). HPLC: (Method A) Rt. 2.6 min, 96.3% (Max). Chiral SFC: (Method B) Rt. 3.9 min, 99.1% (Max).

Analysis of second eluting fraction (example 17): Yield: 42% (42 mg, off white solid). $^1$H NMR (400 MHz, DMSO-$d_6$): δ 12.02 (s, 1H), 7.12 (d, J=7.2 Hz, 1H), 6.75 (d, J=7.6 Hz, 1H), 6.67 (s, 1H), 4.89 (q, J=8.0 Hz, 1H), 3.36-3.33 (m, 6H), 2.80-2.75 (m, 1H), 2.51-2.40 (m, 4H), 2.10 (s, 3H), 1.39 (d, J=6.0 Hz, 3H), 1.28 (d, J=6.4 Hz, 3H). LCMS: (Method A) 388.1 (M+H), Rt 2.1 min 97.5% (Max). HPLC: (Method A) Rt. 2.6 min, 96.3% (Max). Chiral SFC: (Method B) Rt 4.5 min, 100% (Max).

Example 18: 2-(4-((S)-1-((S)-2-methyl-2,3-dihydrobenzofuran-6-yl)ethyl)piperazin-1-yl)-7,8-dihydropyrido[4,3-d]pyrimidin-5(6H)-one or 2-(4-((R)-1-((S)-2-methyl-2,3-dihydrobenzofuran-6-yl)ethyl)piperazin-1-yl)-7,8-dihydropyrido[4,3-d]pyrimidin-5(6H)-one

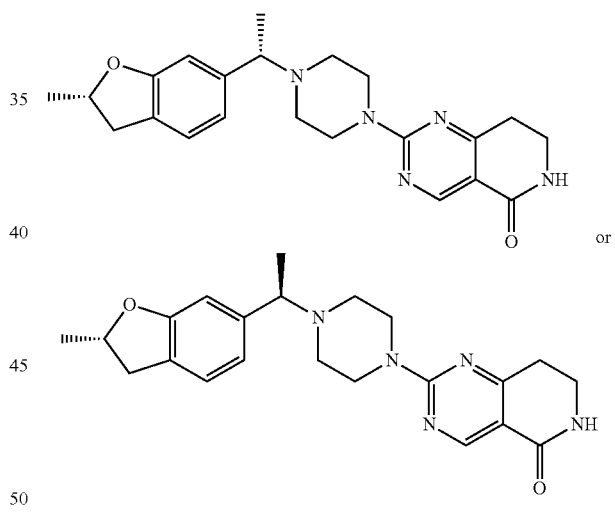

The enantiomers of example 15 were separated by SFC; mobile phase: 20 mM ammonia in methanol, column: Chiracel OJ-H (Method C). The first eluting eluting fraction was concentrated to afford example 18.

Analysis of first eluting fraction (example 18): Yield: 35% (62 mg, off white solid). $^1$H NMR (400 MHz, DMSO-$d_6$): δ 8.58 (s, 1H), 7.70 (s, 1H), 7.11 (d, J=7.6 Hz, 1H), 6.75 (d, J=7.6 Hz, 1H), 6.68 (s, 1H), 4.88 (d, J=6.8 Hz, 1H), 3.85-3.75 (m, 4H), 3.36-3.23 (m, 3H), 3.26 (d, J=5.6 Hz, 1H), 2.80-2.71 (m, 3H), 2.42-2.33 (m, 4H), 1.38 (d, J=6.0 Hz, 3H), 1.28 (d, J=6.4 Hz, 3H). LCMS: (Method A) 394.2 (M+H), Rt 2.0 min, 99.6% (Max). HPLC: (Method A), Rt 2.6 min, 98.7% (Max). Chiral SFC: (Method C) Rt 2.0 min, 100% (max).

Analysis of second eluting fraction (example 18): Yield: 38% (68 mg, off white solid). $^1$H NMR: (400 MHz, DMSO-d$_6$): δ 8.58 (s, 1H), 7.70 (s, 1H), 7.11 (d, J=7.6 Hz, 1H), 6.75 (dd, J=7.6, 1.2 Hz, 1H), 6.68 (s, 1H), 4.85 (d, J=6.8 Hz, 1H), 3.85-3.75 (m, 4H), 3.39-3.34 (m, 3H), 3.30-3.24 (m, 1H), 2.80-2.75 (m, 3H), 2.42-2.34 (m, 4H), 1.38 (d, J=6.0 Hz, 3H), 1.28 (d, J=6.8 Hz, 3H). LCMS: (Method A) 394.2 (M+H), Rt 2.0 min, 99.3% (Max). HPLC: (Method A), Rt 2.6 min, 98.5% (Max). Chiral SFC: (Method C), Rt 2.5 min, 100% (max).

Example 19: 2-(4-(1-((R)-2-methyl-2,3-dihydrobenzofuran-6-yl)ethyl)piperazin-1-yl)-5-(methylsulfonyl)pyrimidine

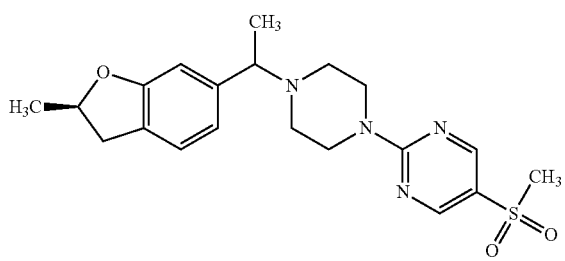 [SMILES: CC(c1ccc2c(c1)O[C@H](C)C2)N1CCN(c2ncc(S(C)(=O)=O)cn2)CC1]

Step 1: 2-chloro-5-(methylsulfonyl)pyrimidine

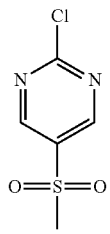

To a stirred solution of 2-chloro-5-(methylthio)pyrimidine (synthesis described in intermediate 8, step 1) (800 mg, 5.0 mmol, Int) in DCM (30 mL) cool to 0° C., m-CPBA (2.58 g, 15.0 mmol) was added, stirred the reaction mixture at rt for 3 h. The reaction mixture was evaporated under vacuum and to the resulting crude water (5 mL) was added. The resulting compound was extracted with EtOAc (50×2 mL) and the combined organic layer was dried over anhydrous sodium sulfate and concentrated. The crude product was purified by column chromatography using eluent Hexane:EtOAc (26%). Yield: 84.21% (3.2 g, yellow gummy). $^1$H NMR: 400 MHz, DMSO-d6: δ 9.25 (s, 2H), 3.43 (s, 3H). HPLC: (Method A), Rt. 1.48 min, 93.30% (Max).

Step 2: 2-(4-(1-((R)-2-methyl-2,3-dihydrobenzofuran-6-yl)ethyl)piperazin-1-yl)-5-(methylsulfonyl)pyrimidine To a stirred solution of intermediate 9 (0.3 g, 0.94 mmol) in ACN (3 mL), 2-chloro-5-(methylsulfonyl)pyrimidine (0.2 g, 1.03 mmol) followed by TEA (0.53 mL, 3.75 mmol) were added at RT and the reaction mixture was stirred at RT for 2 h. Completion of the reaction was monitored by TLC, then the reaction mixture was evaporated at 50° C. under vacuum. To the resulting mixture, water (2 mL) was added and the aqueous layer was extracted with EtOAc (2×15 mL). The combined organic layer was washed with brine solution (20 mL), dried over anhydrous Na$_2$SO$_4$ and concentrated under vacuum. The resulting crude material was purified by flash chromatography (silica gel: 230-400 mesh, eluent: 4% methanol in DCM) to afford the title compound. Yield: 29% (111 mg, pale yellow solid). $^1$H NMR (400 MHz, DMSO-d$_6$): δ 8.68 (s, 2H), 7.11 (d, J=7.6 Hz, 1H), 6.75 (d, J=7.6 Hz, 1H), 6.68 (s, 1H), 4.91-4.86 (m, 1H), 3.85-3.83 (m, 4H), 3.40-3.33 (m, 1H), 3.30-3.24 (m, 1H), 3.21 (s, 3H), 2.77-2.68 (m, 1H), 2.56-2.33 (m, 4H), 1.38 (q, J=2.8 Hz, 3H), 1.28 (d, J=6.4 Hz, 3H). LCMS: (Method A) 403.2 (M+H), Rt. 2.1 min, 98.6% (Max). HPLC: (Method A) Rt 2.9 min, 99.4% (Max).

Example 20: imino(methyl)(2-(4-(1-((R)-2-methyl-2,3-dihydrobenzofuran-6-yl)ethyl)piperazin-1-yl)pyrimidin-5-yl)-λ$^6$-sulfanone

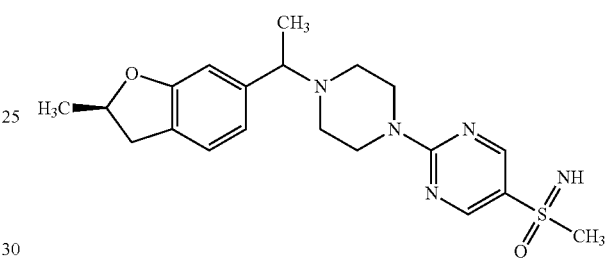

Step 1: 2,2,2-trifluoro-N-(methyl(2-(4-(1-((R)-2-methyl-2,3-dihydrobenzofuran-6-yl)ethyl) piperazin-1-yl) pyrimidin-5-yl) (oxo)-λ$^6$-sulfanylidene)acetamide

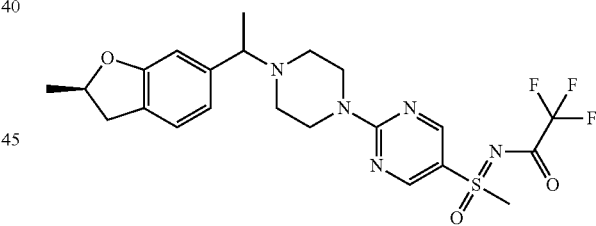

To a stirred solution of intermediate 9 (0.3 g, 0.94 mmol) in ACN (3.0 mL), TEA (0.53 mL, 3.75 mmol) and intermediate 8 (0.3 g, 1.03 mmol) were added at RT and the reaction mixture was stirred at RT for 2 h. Completion of the reaction was monitored by TLC, then the reaction mixture was evaporated at 50° C. under vacuum. To the resulting mixture, water (2 mL) was added and the aqueous layer was extracted with EtOAc (2×15 mL). The combined organic layer was washed with brine solution (20 mL), dried over anhydrous Na$_2$SO$_4$ and concentrated under vacuum. The resulting crude material was purified by flash chromatography (silica gel: 230-400 mesh, eluent: 25% EtOAc in pet-ether) to afford the title compound. Yield: 66% (0.31 g, pale yellow solid). $^1$H NMR (400 MHz, DMSO-d$_6$): δ 8.68 (s, 2H), 7.11 (d, J=7.6 Hz, 1H), 6.80-6.76 (m, 2H), 4.95 (q, J=7.2 Hz, 1H), 4.92-4.11 (m, 1H), 3.98-3.97 (m, 4H), 3.47 (s, 3H), 3.34-3.28 (m, 1H), 2.85-2.79 (m, 1H), 2.55-2.54 (m, Step 2: Imino(methyl)(2-(4-(1-((R)-2-methyl-2,3-dihydrobenzofuran-6-yl)ethyl)piperazin-1-yl)pyrimidin-5-yl)-λ⁶-sulfanone

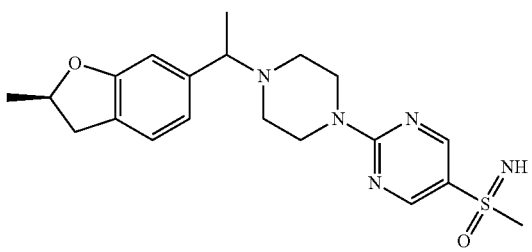

To a stirred solution of 2,2,2-trifluoro-N-(methyl(2-(4-(1-((R)-2-methyl-2,3-dihydrobenzofuran-6-yl)ethyl)piperazin-1-yl)pyrimidin-5-yl)(oxo)-λ⁶-sulfanylidene)acetamide (0.31 g, 0.61 mmol) in methanol (6.1 mL, 20 V), $K_2CO_3$ (170 mg, 1.22 mmol) was added and the reaction mixture was stirred for 20 min. Completion of the reaction was monitored by TLC, then after 20 min, the reaction mixture was filtered through celite and the filtrate was concentrated under vacuum. To the resulting mixture, water (2 mL) was added and the aqueous layer was extracted with EtOAc (2×10 mL). The combined organic layer was washed with brine solution (10 mL), dried over anhydrous $Na_2SO_4$ and concentrated under vacuum. The resulting crude material was purified by flash chromatography (Biotage Isolera, gradient: 1-4% methanol in DCM) to afford the title compound. Yield: 19% (74 mg, off white solid). ¹H NMR (400 MHz, DMSO-d₆): δ 8.66 (s, 2H), 7.11 (d, J=7.6 Hz, 1H), 6.75 (d, J=7.2 Hz, 1H), 6.68 (s, 1H), 4.89-4.86 (m, 1H), 4.25 (s, 1H), 3.83-3.81 (m, 4H), 3.39-3.34 (m, 1H), 3.30-3.24 (m, 1H), 3.08 (s, 3H), 2.77-2.68 (m, 1H), 2.44-2.34 (m, 4H), 1.38 (q, J=6.2 Hz, 3H), 1.28 (d, J=6.4 Hz, 3H). LCMS: (Method A) 402.2 (M+H), Rt 1.9 min, 99.0% (Max). HPLC: (Method A) Rt 2.3 min, 97.9% (Max).

Example 21: 5-(4-(1-((R)-2-methyl-2,3-dihydrobenzofuran-6-yl)ethyl)piperazin-1-yl)-1,3,4-thiadiazol-2(3H)-one Step 1: tert-butyl 4-(hydrazinecarbonothioyl)piperazine-1-carboxylate

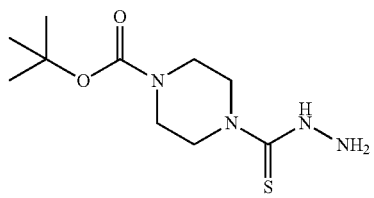 [SMILES: CC(C)(C)OC(=O)N1CCN(C(=S)NN)CC1]

To a stirred solution of tert-butyl piperazine-1-carboxylate (5.0 g, 26.845 mmol) in THF (50 mL), TEA (11.31 mL, 80.536 mmol) and thiocarbonyldiimidazole (9.57 g, 53.69 mmol) were added at RT and the reaction mixture was stirred for 2 h at RT. After 2 h, hydrazine hydrate (4.03 mL, 80.54 mmol) was added to the reaction mixture and stirred for 2 h at RT. Completion of the reaction was monitored by TLC, then water (50 mL) was added to the resulting mixture and the aqueous layer was extracted with EtOAc (2×25 mL). The combined organic layer was washed with brine solution (20 mL), dried over anhydrous $Na_2SO_4$ and concentrated under vacuum. The resulting crude material was forwarded as such to the next step without any further purification. Yield: 92% (4.5 g, off white solid.). ¹H NMR (400 MHz, DMSO-d₆): δ 9.12 (s, 1H), 4.74 (bs, 2H), 3.71 (d, J=4.1 Hz, 4H), 2.80-2.78 (m, 4H) 1.41 (s, 9H). LCMS: (Method A) 261.0 (M+H), Rt. 2.0 min, 95.6% (Max).

Step 2: tert-butyl 4-(5-oxo-4,5-dihydro-1,3, 4-thiadiazol-2-yl)piperazine-1-carboxylate

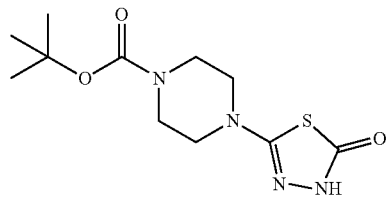 [SMILES: CC(C)(C)OC(=O)N1CCN(c2n[nH]c(=O)s2)CC1]

To the stirred solution of tert-butyl 4-(hydrazinecarbonothioyl) piperazine-1-carboxylate (4.5 g, 13.46 mmol) in DCM (35 mL), TEA (6.60 mL, 40.39 mmol) and carbonyldiimidazole (8.3 g, 40.39 mmol) were added at RT for 4 h. Completion of the reaction was monitored by TLC, then water (25 mL) was added to the resulting mixture and the aqueous layer was extracted with EtOAc (2×25 mL). The combined organic layer was washed with brine solution (25 mL), dried over anhydrous $Na_2SO_4$ and concentrated under vacuum. The resulting crude material was purified by flash chromatography (silica gel: 230-400 mesh, eluent: 1-2% methanol in DCM) to afford the title compound. Yield: 58% (2.8 g, off white solid). ¹H NMR (400 MHz, DMSO-d₆): δ 11.79 (s, 1H), 3.38-3.36 (m, 4H), 3.18-3.16 (m, 4H), 1.41 (s, 9H). LCMS: (Method A) 231.0 (M-t-butyl), Rt. 2.4 min, 99.9% (Max).

Step 3: 5-(piperazin-1-yl)-1, 3, 4-thiadiazol-2(3H)-one hydrochloride

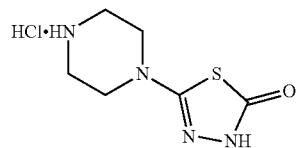

To a stirred solution of tert-butyl 4-(hydrazinecarbonothioyl) piperazine-1-carboxylate (2.8 g, 5.069 mmol) in dry 1,4-dioxane (10 mL) at 0° C., HCl solution in dioxane (20 mL, 4M) was added dropwise and the reaction mixture was stirred for 4 h at RT. Completion of the reaction was monitored by TLC, then the reaction mixture was evaporated under vacuum to afford the tittle compound. Yield: 86% (1.81 g, off white solid). ¹H NMR (400 MHz, DMSO-d₆): δ 11.96 (s, 1H), 9.51 (s, 2H), 3.45 (t, J=4.8 Hz, 4H), 3.16 (bs, 4H). LCMS: (Method A) 187.1 (M+H), Rt. 0.5 min, 90.7% (Max).

Step 4: 5-(4-(1-((R)-2-methyl-2, 3-dihydrobenzofuran-6-yl)ethyl)piperazin-1-yl)-1,3, 4-thiadiazol-2(3H)-one

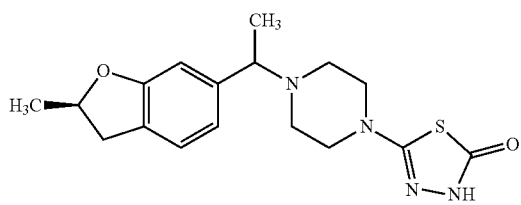 [SMILES: CC(c1ccc2c(c1)O[C@H](C)C2)N1CCN(c2n[nH]c(=O)s2)CC1]

To a stirred solution of 5-(piperazin-1-yl)-1,3,4-thiadiazol-2(3H)-one dihydrochloride (0.51 g, 1.95 mmol)) in dry DMF (3.5 mL), TEA (1.0 mL, 7.11 mmol) and intermediate 4 (350 mg, 1.77 mmol) were added at Rt and the reaction mixture was heated at 80° C. overnight. Completion of the reaction was monitored by TLC, then the reaction mixture was evaporated at 55° C. under vacuum. To the resulting mixture, water (2 mL) was added and the aqueous layer was extracted with EtOAc (3×10 mL). The combined organic layer was washed with brine solution (10 mL), dried over anhydrous $Na_2SO_4$ and concentrated under vacuum. The resulting crude material was purified by flash chromatography (Biotage Isolera, eluent: 4-5% methanol in DCM) to afford the title compound. Yield: 30% (184 mg, pale yellow solid). $^1$H NMR (400 MHz, DMSO-$d_6$): δ 11.70 (s, 1H), 7.11 (d, J=7.6 Hz, 1H), 6.73 (d, J=7.6 Hz, 1H), 6.66 (s, 1H), 4.91-4.85 (m, 1H), 3.39-3.33 (m, 1H), 3.30-3.24 (m, 1H), 3.17-3.12 (m, 4H), 2.77-2.68 (m, 1H), 2.48-2.35 (m, 4H), 1.38 (d, J=6.4 Hz, 3H), 1.26 (d, J=6.4 Hz, 3H). LCMS: (Method A) 347.1 (M+H), Rt 2.0 min, 96.2% (Max). HPLC: (Method A) Rt 2.5 min, 94.8% (Max).

Example B01: Human O-GlcNAcase Enzyme Inhibition Assay

5 µl of the appropriate concentration of a solution of inhibitor in McIlvaine's Buffer (pH 6.5) in 2% DMSO (for a dose response curve calculation) is added into each well of a 384-well plate (Greiner, 781900). Then, 20 nM of His-Tagged hOGA and 10 µM of FL-GlcNAc (Fluorescein mono-beta-D-(2-deoxy-2-N-acetyl) glucopyranoside; Marker Gene Technologies Inc, M1485) were added to the 384-well plate for a final volume of 20 µl. After incubation for 60 min at room temperature, the reaction was terminated by the addition of 10 µL of stop buffer (200 mM glycine, pH 10.75). The level of fluorescence ($\lambda_{exc}$ 485 nm; ($\lambda_{emm}$ 520 nm) was read on a PHERAstar machine. The amount of fluorescence measured was plotted against the concentration of inhibitor to produce a sigmoidal dose response curve to calculate an $IC_{50}$. All individual data was corrected by subtraction of the background (Thiamet 3 uM=100% inhibition) whilst 0.5% DMSO was considered as the control value (no inhibition).

Example B02: Pharmacodynamic Model: Total Protein O-GlcNAcylation Immunoassay (RL2 mAb, Meso Scale Electrochemiluminescence (ECL) Assay)

The test compound was administered orally to C57BL/6J mice. At defined time intervals after compound administration, typically a time ranging between 2 and 48 hours, preferably between 4 and 24 hours, mice were sacrificed by decapitation for blood collection and forebrain dissection. Right brain hemispheres were placed in 2 ml Precellys tubes, snap frozen in dry ice and stored at -80° C. Left hemispheres were placed in 2 ml Eppendorf tubes, snap frozen in dry ice and stored at -80° C. until further processing. Blood samples were collected in Sarstedt tubes containing 35 IU of Heparin and kept at 4° C. After centrifugation for 10 min at 3800 xg, 4° C., 50 µL of plasma from each sample was transferred to a 1.5 ml Eppendorf tube and stored at −80° C.

For the preparation of soluble brain protein for the immunoassay the hemispheres were homogenized in ice-cold Cytobuster reagent (71009—Merck Millipore) buffer with protease inhibitor cocktail. After centrifugation for 15 min at 17000 xg at 4° C. the supernatants were transferred into polycarbonate tubes (1 ml). The supernatants were cleared by centrifugation for 1 h. at 100000 xg, 4° C., and the protein concentrations were determined by using the BCA kit (23227—Pierce, Rockford, Ill.) according to the manufacturer's instructions.

Total Protein O-GlcNAcylation Immunoassay:

Samples were randomised and 120 µg/ml (25 µl/well) of soluble brain protein was directly coated on a Multi-array 96-well high bind plate (L15XB-3 High bind—Meso Scale Discovery) overnight at 4° C. After washing (3× with PBS-T buffer), the plate was blocked with MSD blocker A solution for 1 h. at room temperature (RT) under agitation. After washing (3× with PBS-T buffer), the plate was incubated with 0.1 µg/ml of a mouse monoclonal antibody directed against O-GlcNAc moieties (RL2; MA1-072—Thermo Scientific) for 1 h. at RT under agitation. For the ECL assay, after washing (3× with PBS-T buffer), 1 µg/ml of a SULFO-TAG™ labeled anti-mouse secondary antibody (Meso Scale Discovery) was added and the plate was incubated for 1 h. at RT under agitation and protected from light. After washing (3× with PBS-T buffer), 150 µl/well of 1× Read Buffer T was added to the plates before reading on a Sector Imager 6000 (Meso Scale Discovery).

Example B03: Pharmaceutical Preparations (A) Injection vials: A solution of 100 g of an active ingredient according to the invention and 5 g of disodium hydrogen phosphate in 3 l of bi-distilled water was adjusted to pH 6.5 using 2 N hydrochloric acid, sterile filtered, transferred into injection vials, lyophilized under sterile conditions and sealed under sterile conditions. Each injection vial contained 5 mg of active ingredient.

(B) Suppositories: A mixture of 20 g of an active ingredient according to the invention was melted with 100 g of soy lecithin and 1400 g of cocoa butter, poured into moulds and allowed to cool. Each suppository contained 20 mg of active ingredient.

(C) Solution: A solution was prepared from 1 g of an active ingredient according to the invention, 9.38 g of $NaH_2PO_4 \cdot 2H_2O$, 28.48 g of $Na_2HPO_4 \cdot 12H_2O$ and 0.1 g of benzalkonium chloride in 940 ml of bi-distilled water. The pH was adjusted to 6.8, and the solution was made up to 1 l and sterilized by irradiation. This solution could be used in the form of eye drops.

(D) Ointment: 500 mg of an active ingredient according to the invention were mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate was pressed to give tablets in a conventional manner in such a way that each tablet contained 10 mg of active ingredient.

(F) Coated tablets: Tablets were pressed analogously to EXAMPLE E and subsequently coated in a conventional manner with a coating of sucrose, potato starch, talc, tragacanth and dye.

(G) Capsules: 2 kg of an active ingredient according to the invention were introduced into hard gelatin capsules in a conventional manner in such a way that each capsule contained 20 mg of the active ingredient.

(H) Ampoules: A solution of 1 kg of an active ingredient according to the invention in 60 l of bi-distilled water was sterile filtered, transferred into ampoules, lyophilized under sterile conditions and sealed under sterile conditions. Each ampoule contained 10 mg of active ingredient.

(I) Inhalation spray: 14 g of an active ingredient according to the invention were dissolved in 10 l of isotonic NaCl solution, and the solution was transferred into commercially available spray containers with a pump mechanism. The solution could be sprayed into the mouth or nose. One spray shot (about 0.1 ml) corresponded to a dose of about 0.14 mg.

Example B04: Protein Binding in Mice Plasma Using Rapid Equilibrium Dialysis

Materials
CD1 Mice Plasma: pooled male, K2-EDTA (MSEPLEDTA2, Bioreclammation, USA
Phosphate Buffered Saline (1×PBS), pH 7.4, 100 mM (Sigma, Cat No. P4417)
RED inserts (Pierce, Cat No. 9006, 8 kDa MWCO)
Sample Analysis: LC-MS/MS
Methods
Preparation of DMSO Stock Solution
From 20 mM DMSO stock solutions of reference and test compounds, 1 mM DMSO intermediate working solutions are prepared. From 1 mM intermediate working solutions, 100 µM DMSO working solutions are prepared.
Sample Preparation Procedure:
Selected plasma is brought from −20° C. to 37° C. using water bath before its use. Test solution is prepared by adding the DMSO working solution of the reference or test compound (2 µL; 100 µM) to the selected plasma (198 µL). Spiked plasma (200 µl) is transferred to sample compartment of RED insert placed in the teflon plate. 350 µl of 1×PBS is added in the buffer compartment of RED insert. The teflon plate is covered with sealing mat and agitated at 37° C. for 5 hours at 500 RPM in a Thermomixer. After incubation time, an aliquot of plasma (50 µl) from sample compartment is mixed with blank 1×PBS (50 µl). Similarly, an aliquot of buffer (50 µl) from buffer compartment is mixed with blank plasma (50 µl). Quenching solution (200 µL, acetonitrile containing internal standard tolbutamide (0.5 µg/mL)) is added and the resulting solutions are mixed using a vortex mixer and centrifuged (Eppendorf 5415, 13792 g). Supernatants are analyzed using a Mass Spectrometer. The sample (supernatant fraction, 5 µL) is injected into the LC-MS/MS instrument.

Chromatographic Conditions:
LC-MS/MS: API 4000 LC-MS/MS
Software: Analyst Version 1.6.1
Column Phenomenex Synergy 30*4.6*5µ
Column Oven: 40° C.
Mode: ESI Positive
Injection volume: 5 µl
Flow Rate: 1000 µL/mL
Buffer: 0.1% Formic acid in Water
Method: Isocratic Method/Gradient
Composition: A) 0.1% Formic acid in Water
B) 0.1% Formic acid in Methanol

| Time (Sec) | Flow (µL) | Mobile Phase A | Mobile Phase B |
|---|---|---|---|
| 0.01 | 1000 | 10 | 90 |
| 0.4 | 1000 | 10 | 90 |
| 0.8 | 1000 | 90 | 10 |
| 1.5 | 1000 | 90 | 10 |
| 1.8 | 1000 | 10 | 90 |
| 2.5 | 1000 | 10 | 90 |

Results Calculation
After the concentration of free drug and total drug has been determined by LCMS/MS, percent plasma protein binding can be calculated as follows:

$$\% \text{ fraction unbound} = \frac{\text{Drug concentration in buffer after 5 hours}}{\text{Drug concentration in plasma after 5 hours}} \times 100$$

Following this protocol, % fraction unbound in plasma from different species can be also measured.

Example B05: Determination of In Vitro Intrinsic Clearance ($Cl_{int}$-In Vitro) with Mouse, Rat and Human Liver Microsomes In this assay, test compounds are incubated with liver microsomes from mouse, rat and human, and rate of disappearance of drug is determined using LC-MS/MS. Conditions used in the assay are summarized below:
Materials
CD-1 Mice liver microsomes, pooled male (Life Technologies, Cat No. MSMC-PL) (20 mg/ml)
SD Rat liver microsomes, pooled male (Life Technologies, Cat No. RTMCL-PL) (20 mg/ml)
Human liver microsomes, pooled mixed gender (Life Technologies, Cat No. HMMC-PL) (20 mg/ml)
NADPH (SRL Mumbai, Cat No. 99197)
Verapamil (Sigma, Cat No. V4629)
Atenolol (Sigma, Cat No. A7655)
Tolbutamide (Sigma Cat. No. T0891)
Assay buffer: 50 mM potassium phosphate buffer, pH 7.4
Test & reference compounds: DMSO stock solutions (10 mM concentration) are prepared and stored at room temperature. An intermediate 1 mM solution of test or reference compounds is prepared by mixing 10 µL of 10 mM DMSO stock with 90 µL of DMSO. The contents are mixed vigorously in a vortex mixer.
Methods
Preparation of Working Solutions of Test and Reference Compounds:
Working solution (100 µM concentration) is prepared by mixing 10 µL of 1 mM DMSO solution of test or reference compounds with 90 µL of assay buffer. The mixture is mixed vigorously in a vortex mixer. This resulting solution is containing 10% of DMSO. For the metabolic stability assay, 10 µL of this 100 µM working solution is added to a final assay volume of 1 mL, yielding final test concentration of 1 µM and DMSO concentration of 0.1%.
Metabolic Stability Assay
Metabolic stability assay is done in a final volume of 1 ml in 50 mM assay buffer, potassium phosphate buffer, pH 7.4. Assay is carried out in duplicates (n=2). A mixture containing 955 µL of assay buffer, 25 µL of liver microsomes and 10 µL of 100 µM test compound solution is pre-incubated for 10 minutes in a water-bath maintained at 37° C. After pre-incubation, reaction is started by adding 10 µL of 100 mM NADPH solution. The solution is mixed and incubated at 37° C. in a water-bath. The final concentration of the different components in the assay is: DMSO 0.1%, test compound 1 µM, liver microsome protein 0.5 mg/ml and NADPH 1 mM.

Aliquots (100 µL) are taken at various time-points (0, 5, 15, 30 and 45 minutes) and quenched with 100 µL of acetonitrile containing tolbutamide (500 ng/mL) as internal standard. Samples are mixed using a vortex mixer and centrifuged at 4000 rpm for 10 minutes (Eppendorf 5810R, 3000 g). The supernatants (5 µL) are transferred to 96 well plates and submitted for LC-MS/MS analysis.

Separate incubations in the same assay mixture, but in the absence of NADPH, are run in parallel as control for compound stability. This control assay is carried out in duplicates (n=2). After pre-incubation, addition of NADPH is omitted and replaced with 10 µL of assay buffer. The final assay volume is 1 mL and aliquots (100 µL) are withdrawn and processed for analysis as described for metabolic stability assay.

LC-MS/MS Conditions (Generic Method)
LC-MS/MS: API Sciex 4000 with Nexera™ UHPLC
Software: Analyst Version 1.6.1
Column: Phenomenex kinetex C18 50×3.0 mm, 2.6p
Column Oven: 40° C.
Mode: ESI Positive
Injection volume: 5 µl
Flow Rate: 1000 µL/mL
Buffer: 0.1% Formic acid in Water
Method: Isocratic Method/Gradient
Composition: A) 0.1% Formic acid in Water
B) 0.1% Formic acid in Methanol

| Time (Sec) | Flow (µL) | Mobile Phase A | Mobile Phase B |
|---|---|---|---|
| 0.01 | 1000 | 10 | 90 |
| 0.4 | 1000 | 10 | 90 |
| 1 | 1000 | 90 | 10 |
| 1.5 | 1000 | 90 | 10 |
| 1.8 | 1000 | 10 | 90 |
| 3 | 1000 | 10 | 90 |

Results Calculation

From LC-MS/MS data, amount of drug remaining at different time points was determined (% PCR). The logarithm of % PCR was plotted against time to get the slope value. From the slope value, in vitro $T_{1/2}$ was determined. In vitro intrinsic clearance ($Cl_{int}$) was calculated using the following formulae:

$$CL_{int} = \frac{0.693}{\text{In vitro } t_{1/2}} \times \frac{\text{Volume of incubation}}{\text{mg of microsomal protein}} \quad \text{In vitro } t_{1/2} = \frac{0.693}{K_{el}}$$

Where $K_{el}$ is Elimination Constant (slope)

Methods for treating the diseases mentioned in this specification, such as tauopathy, by administering one or more of the compounds of the present invention to a patient in need thereof are also object of this invention.

If chemical bonds in the structures above are drawn as follows:

they indicate a defined, i.e. R or S, stereochemistry at at least one of the atoms to which they are attached to.

This is exemplified below, wherein the structure

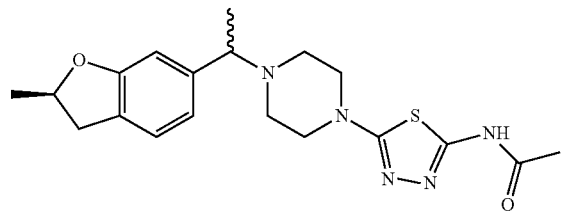 [SMILES: CC(=O)Nc1nnc(N2CCN(C(C)c3ccc4c(c3)O[C@H](C)C4)CC2)s1]

is representing only one of the two possible diastereoisomers,

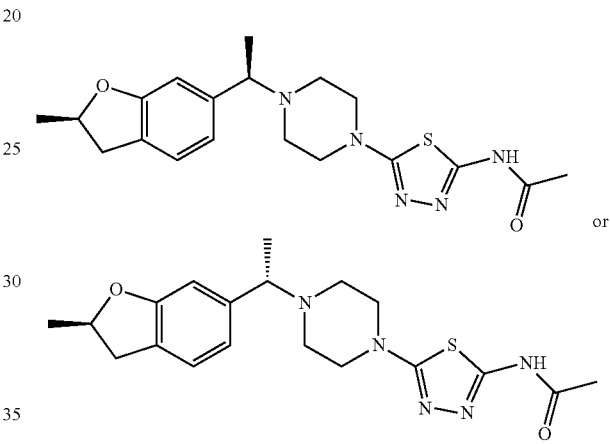

i.e. a single individual chemical structure as opposed to a mixture of diastereoisomers.

The invention claimed is:
1. A compound of formula (I)

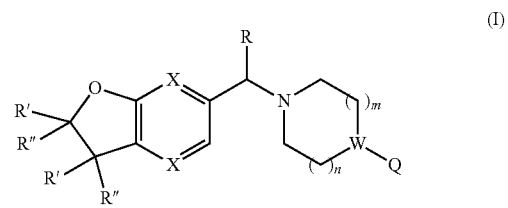

wherein
R is straight chain or branched alkyl having 1 to 6 carbon atoms, wherein 1 to 5 hydrogen atoms may be replaced by Hal or OH;
W is CH or N;
X is N or CR''';
R', R'' denote each independently H, Hal or straight chain or branched alkyl having 1 to 12 carbon atoms, wherein at least one of R' and R'' is different from H;
R''' denotes H, Hal, $NR^3R^4$, $CHR^3R^4$, $OR^3$, CN or a straight chain or branched alkyl having 1 to 12 carbon atoms, wherein 1 to 3 $CH_2$-groups may be replaced by a group selected from O, $NR^3$, S, SO, $SO_2$, $S(O)(NR^{3'})$, $N(SO)R^{3'}$, CO, COO, OCO, $CONR^3$, $NR^3CO$,

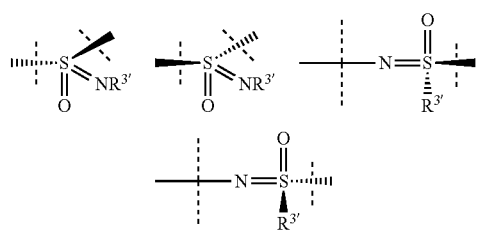
and wherein 1 to 5 hydrogen atoms may be replaced by Hal, NR³R⁴ or NO₂ or by one of the following groups:
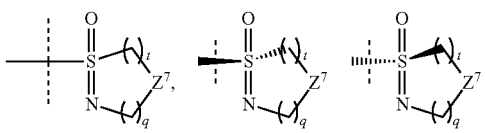
or R''' denotes one of the following groups:
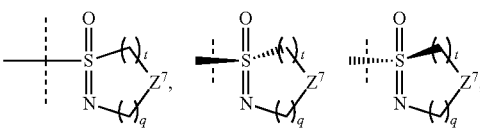
R³, R⁴ denote each independently H or a straight chain or branched alkyl group having 1 to 12 carbon atoms;
Q denotes one of the following groups:
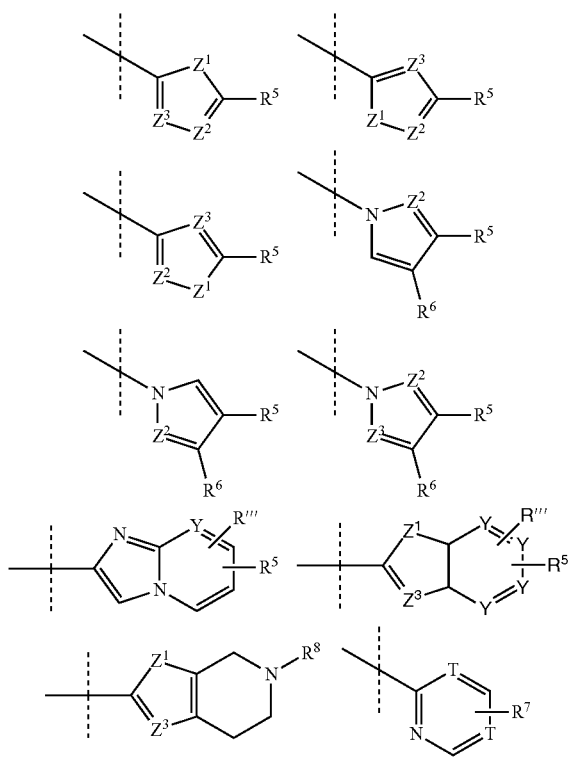
-continued
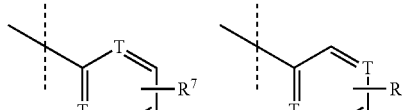
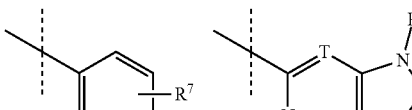
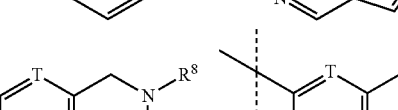
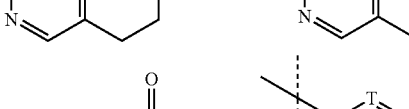
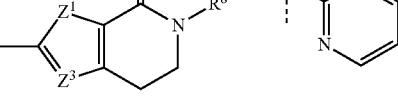
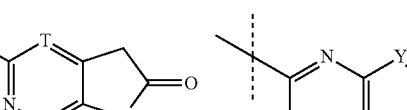
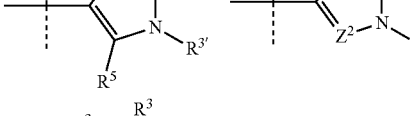
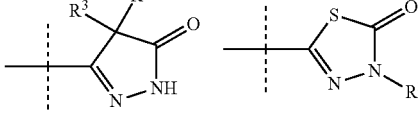
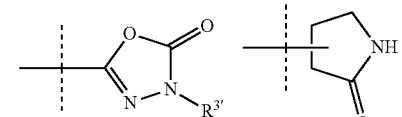
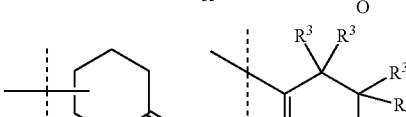
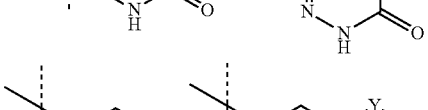
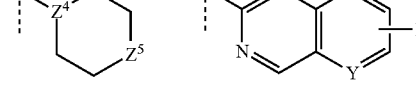
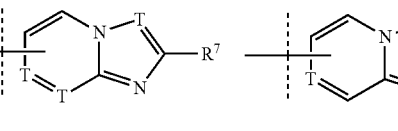

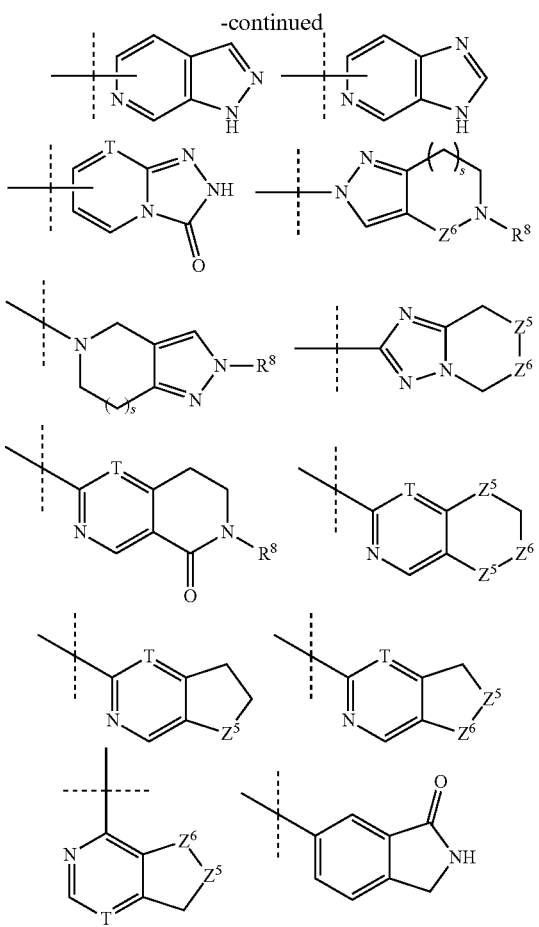

Y is N or CR'";
$Z^1$ is S, O, $NR^3$;
$Z^2$, $Z^3$ independently denote $CR^5$ or N;
$Z^4$ is N, CH, CON, COCH;
$Z^5$ is $NR^8$, $CHR^5$, S(O)($NR^{3'}$), N(SO)$R^{3'}$,

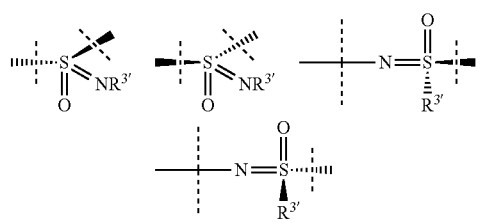

$Z^6$ is $CH_2$, CO, $SO_2$, S(O)($NR^{3'}$), N(SO)$R^{3'}$,

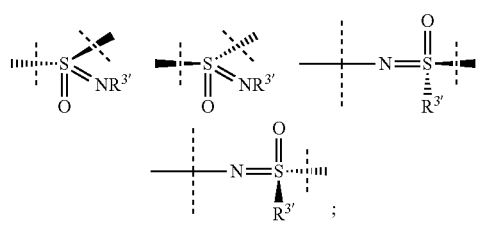

$Z^7$ is $C(R^{3'})_2$, S, O, $NR^{3'}$;
s denotes 0 or 1;
T is N, CH or $CR^7$;
$R^{3'}$ denotes H or a straight chain or branched alkyl group having 1 to 12 carbon atoms, wherein 1 to 3 $CH_2$-groups may be replaced by a group selected from $SO_2$, CO, O and wherein 1 to 5 hydrogen atoms may be replaced by Hal;
$R^5$, $R^6$, $R^7$ independently denote H, Hal, $NR^3R^4$, $NO_2$ or a straight chain or branched alkyl having 1 to 12 carbon atoms, wherein 1 to 3 $CH_2$-groups may be replaced by a group selected from O, $NR^3$, S, SO, $SO_2$, S(O)($NR^{3'}$), N(SO)$R^{3'}$, CO, COO, OCO, $CONR^3$, $NR^3CO$

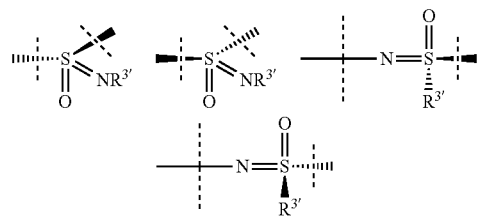

and wherein 1 to 5 hydrogen atoms may be replaced by Hal, $NR^3R^4$, $NO_2$, $OR^3$, Het, Ar, Cyc, or by one of the following groups:

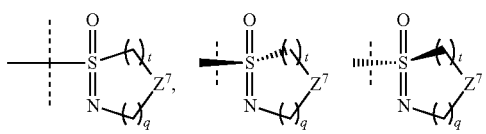

or $R^5$, $R^6$, $R^7$ denote Ar, Het or Cyc or one of the following groups:

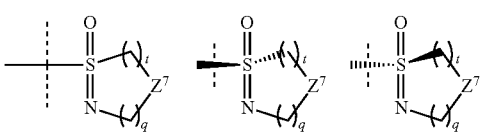

$R^8$ denotes H or straight chain or branched alkyl having 1 to 12 carbon atoms, wherein 1 to 3 $CH_2$-groups may be replaced by a group selected from SO, $SO_2$, S(O)($NR^{3'}$), N(SO)$R^{3'}$, CO, COO, OCO, $CONR^3$, $NR^3CO$, and

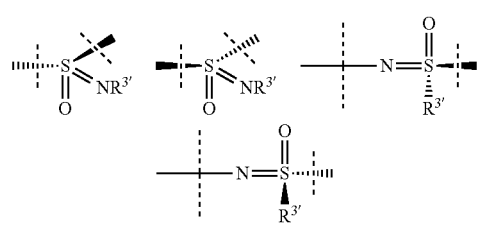

and further wherein 1 to 5 hydrogen atoms may be replaced by CN, $OR^3$, $SR^3$, Hal, $NR^3R^4$, $NO_2$ or by one of the following groups:

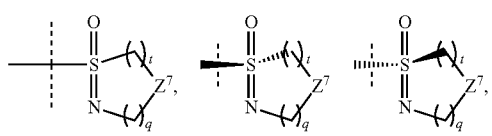

or R⁸ denote one of the following groups:

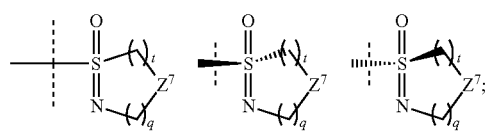

Hal denotes F, Cl, Br or I;
Het denotes a saturated, unsaturated or aromatic ring, being monocyclic or bicyclic or fused-bicyclic and having 3- to 8-members and containing 1 to 4 heteroatoms selected from N, O and S, which may be substituted by 1 to 3 substituents selected from $R^5$, Hal and $OR^3$;
Ar denotes a 6-membered carbocyclic aromatic ring or a fused or non-fused bicylic aromatic ring system, which is optionally substituted by 1 to 3 substituents independently selected from $R^5$, $OR^3$ and Hal;
Cyc denotes a saturated or an unsaturated carbocyclic ring having from 3 to 8 carbon atoms which is optionally substituted by 1 to 3 substituents independently selected from $R^5$ or Hal or OH;
m and n denote independently from one another 0, 1, 2 or 3,
t and q denote independently from one another 0, 1, 2 or 3, with t+q≥1;
and pharmaceutically usable derivatives, solvates, salts, prodrugs, tautomers, enantiomers, racemates and stereoisomers thereof, including mixtures thereof in all ratios and compounds of formula I, wherein one or more H atoms are replaced by D (deuterium).

2. A compound chosen from the group consisting of formula Ia and Ib:

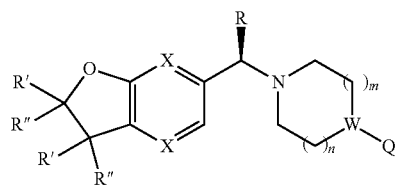

(Ia)

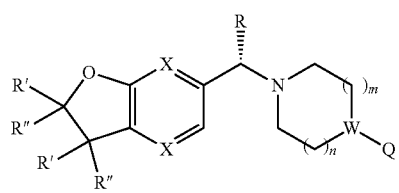

(Ib)

wherein R, R', R", X, W, Q, n and m have the meaning given in claim 1.

3. A mixture comprising compounds Ia and Ib according to claim 2, having identical groups R, R', R", X, W, Q, n and m in equal or unequal amounts.

4. A compound of formula I according to claim 1, wherein R is methyl and/or W is N.

5. A compound of formula I according to claim 1, wherein the groups X denote both simultaneously CH.

6. A compound of formula I according to claim 1, wherein Q denotes one of the following groups:

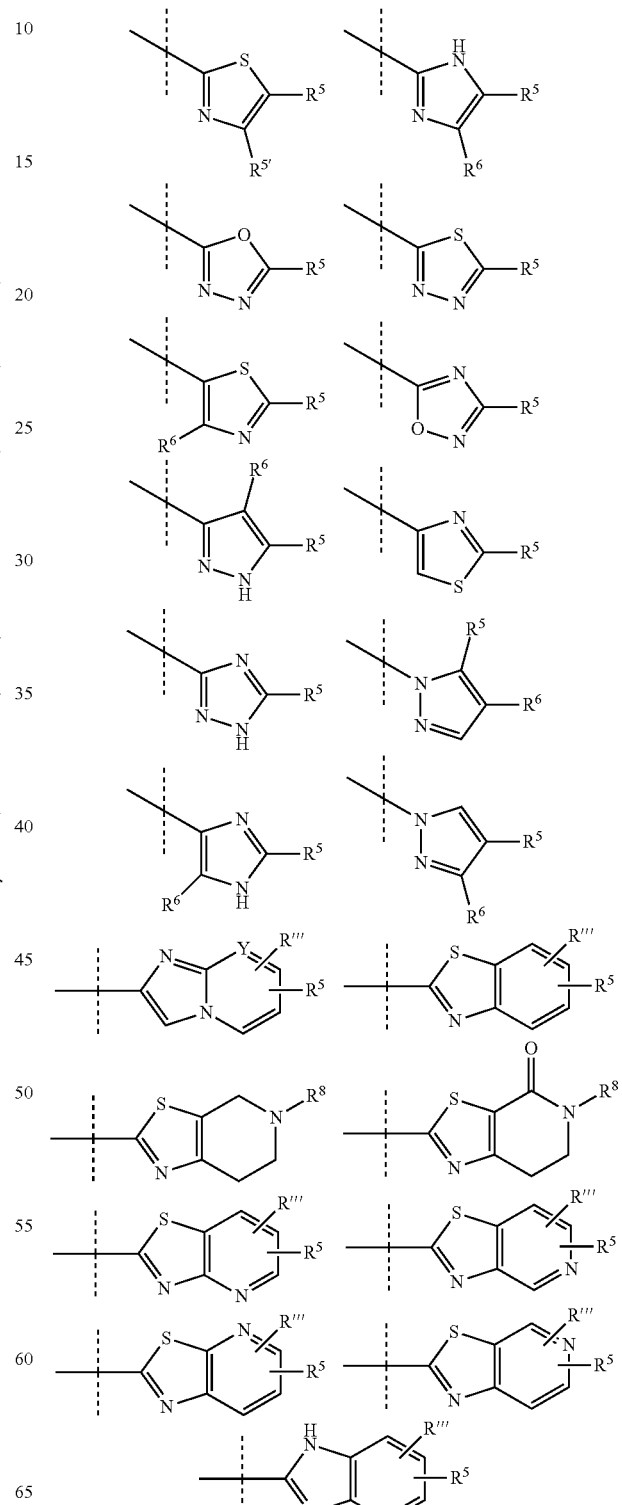

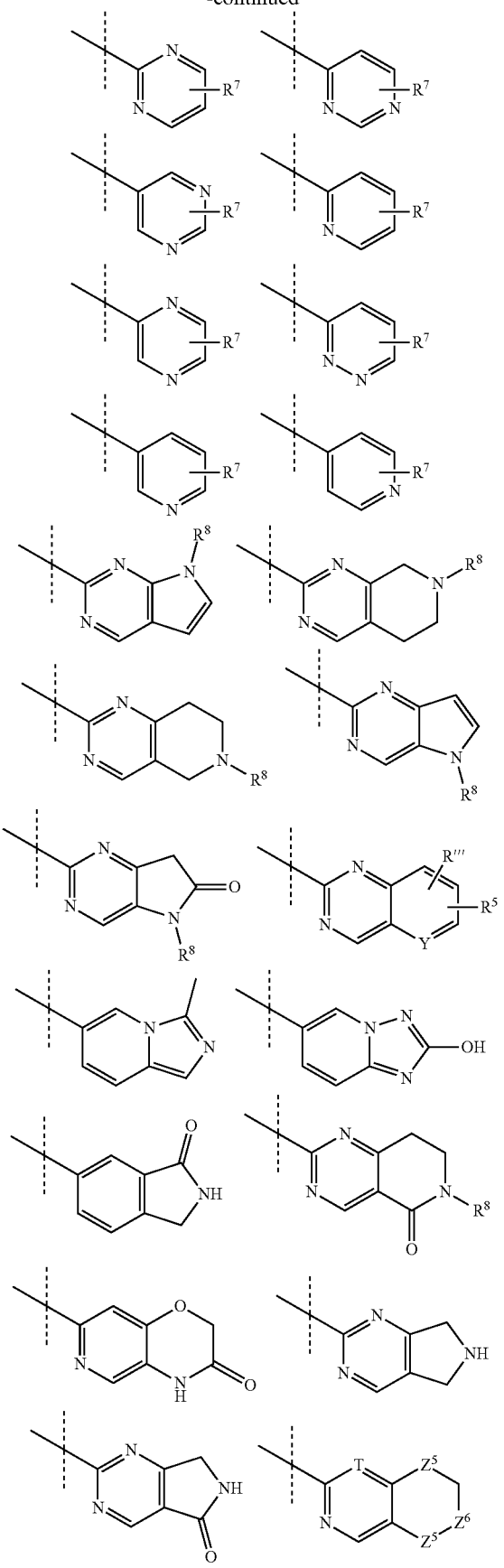

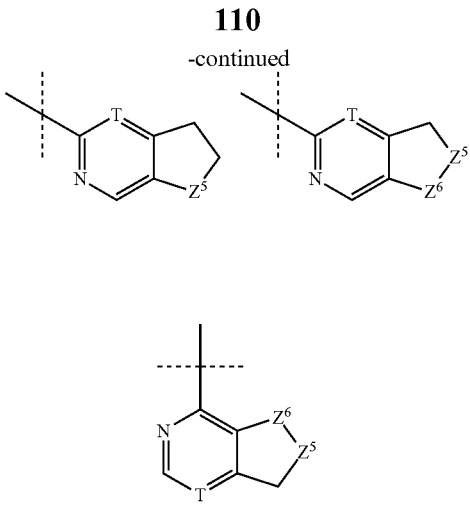

wherein T, Y, $Z^5$, $Z^6$, R''', $R^5$, $R^6$, $R^7$ and $R^8$ have the meaning given in claim 1.

7. A compound of formula I according to claim 1, wherein $R^5$, $R^6$, $R^7$ are independently selected from H, $SO_2CH_3$, $SO_2CH_2CH_3$, $SO_2CH_2CH_2OH$, $SO_2CH_2CH_2OCH_3$, $S(O)(NR^{3'})CH_3$, $S(O)(NR^{3'})CH_2CH_3$, $S(O)(NR^{3'})CH_2CH_2OH$, $S(O)(NR^{3'})CH_2CH_2OCH_3$, $N(SO)R^{3'}CH_3$, $N(SO)R^{3'}CH_2CH_3$, $N(SO)R^{3'}CH_2CH_2OH$, $N(SO)R^{3'}CH_2CH_2OCH_3$, Hal, $NR^3R^4$, $NO_2$, phenyl, 2-, 3- or 4-hydroxy or methoxyphenyl, alkyl, alkoxy (Oalkyl), hydroxyalkylen, alkoxyalkylen, COOH, COOalkyl, CON-Halkyl, $CONH_2$, $CON(CH_3)_2$, NHCOalkyl, $NHCH_2CH_3$, $NHCH_2CH_2CH_3$, $NHCOCH_2CH_2OH$, CO—N-morpholinyl, $CON(CH_3)CH_2CH_2N(CH_3)_2$, CO-1-piperidinyl, CO-4-hydroxy-1-piperidinyl, CO-1-piperazinyl, CO-4-methyl-1-piperazinyl, $CH_2$—N— morpholinyl, $CH_2N(H)COCH_3$, $CH_2N(CH_3)COCH_3$, $CH_2NH_2$, $NH_2$, $CH(OH)CH_3$, $CH(OR^3)CH_3$ and a group

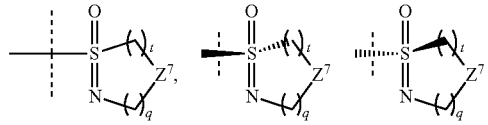

wherein t+q is 2 or 3, $Z^7$, $R^3$, $R^4$ and $R^{3'}$ have the meaning given in claim 1.

8. A compound of formula Ic

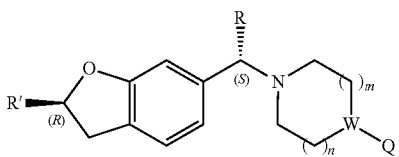

Ic wherein R, R', W, Q, n and m have the meaning given in claim 1.

9. A compound of formula I according to claim 1, wherein m and n simultaneously denote 1.

10. A compound according to claim 1, selected from the following group:

| No | Structure | Configuration specification |
|---|---|---|
| 1 | 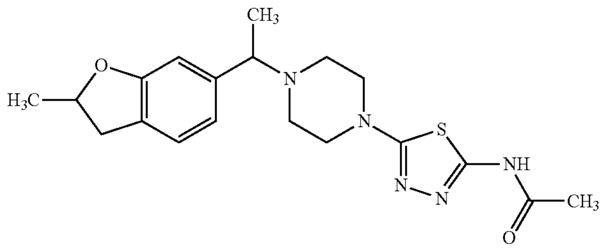 [SMILES: CC(=O)Nc1nnc(N2CCN(C(C)c3ccc4c(c3)OC(C)C4)CC2)s1] | Racemic |
| 2 | 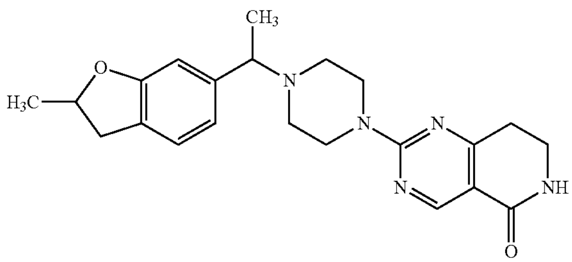 [SMILES: CC1Cc2ccc(C(C)N3CCN(c4ncc5c(n4)CCNC5=O)CC3)cc2O1] | Racemic |
| 3 | 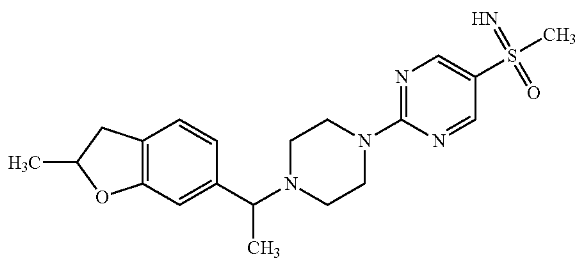 | Racemic |
| 4 | 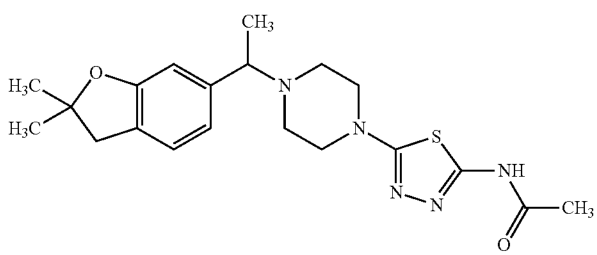 [SMILES: CC(=O)Nc1nnc(N2CCN(C(C)c3ccc4c(c3)OC(C)(C)C4)CC2)s1] | Racemic |
| 5 | 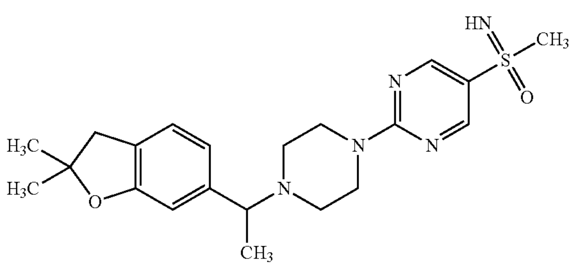 | Racemic |
| 6 | 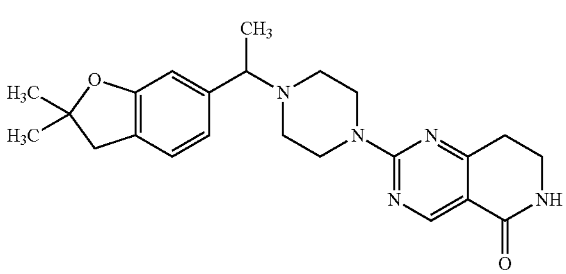 [SMILES: CC(c1ccc2c(c1)OC(C)(C)C2)N1CCN(c2ncc3c(n2)CCNC3=O)CC1] | Racemic |

| No | Structure | Configuration specification |
|---|---|---|
| 7 | 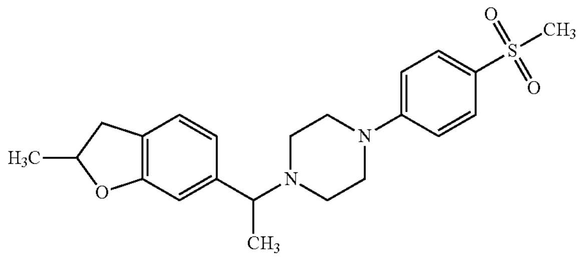 | Racemic |
| 8 | 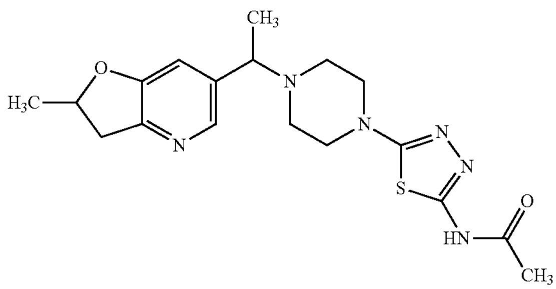 [SMILES: CC(=O)Nc1nnc(N2CCN(C(C)c3cnc4c(c3)OC(C)C4)CC2)s1] | Racemic |
| 9 | 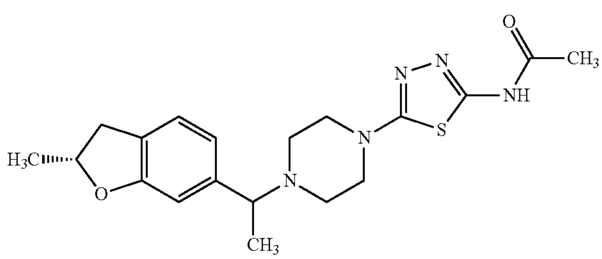 [SMILES: CC(=O)Nc1nnc(N2CCN(C(C)c3ccc4c(c3)O[C@H](C)C4)CC2)s1] | Synthesized from (R)-propane-1,2-diol |
| 10 | 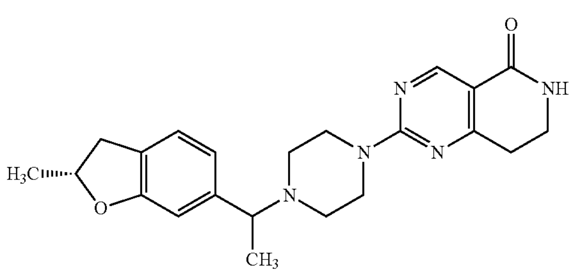 [SMILES: CC(c1ccc2c(c1)O[C@H](C)C2)N1CCN(c2ncc3c(n2)CCNC3=O)CC1] | Synthesized from (R)-propane-1,2-diol |
| 11 | 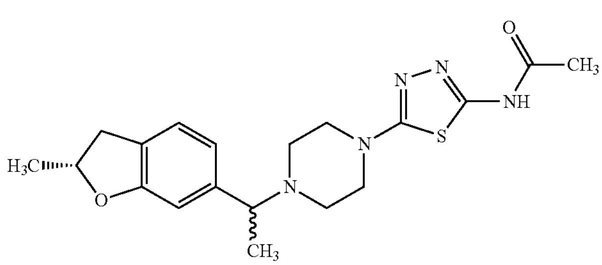 [SMILES: CC(=O)Nc1nnc(N2CCN(C(C)c3ccc4c(c3)O[C@H](C)C4)CC2)s1] | Chiral SFC Method A: 1st eluting compound |

-continued

| No | Structure | Configuration specification |
|---|---|---|
| 12 | 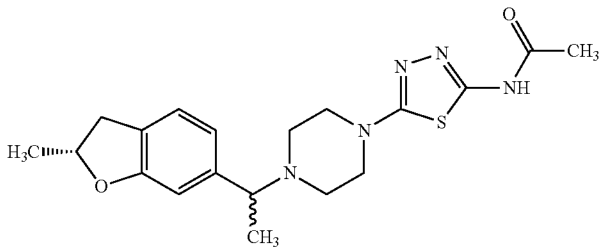 [SMILES: CC(=O)Nc1nnc(N2CCN(C(C)c3ccc4c(c3)O[C@H](C)C4)CC2)s1] | Chiral SFC Method A: 2nd eluting compound |
| 13 | 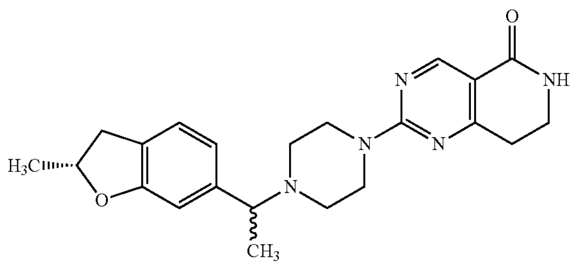 [SMILES: CC(c1ccc2c(c1)O[C@H](C)C2)N1CCN(c2ncc3c(n2)CCNC3=O)CC1] | Chiral SFC Method A: 1st eluting compound |
| 14 | 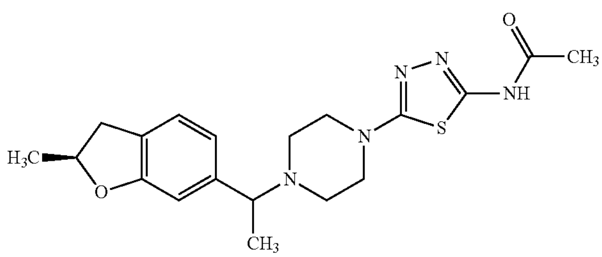 [SMILES: CC(=O)Nc1nnc(N2CCN(C(C)c3ccc4c(c3)O[C@@H](C)C4)CC2)s1] | Synthesized from (S)-propane-1,2-diol |
| 15 | 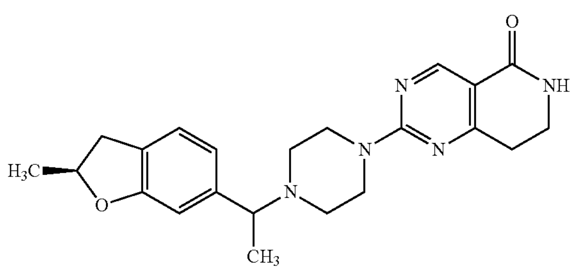 [SMILES: CC(c1ccc2c(c1)O[C@@H](C)C2)N1CCN(c2ncc3c(n2)CCNC3=O)CC1] | Synthesized from (S)-propane-1,2-diol |
| 16 | 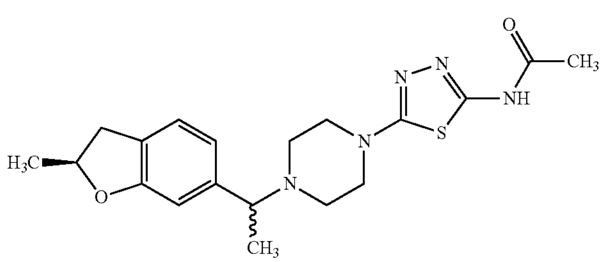 [SMILES: CC(=O)Nc1nnc(N2CCN(C(C)c3ccc4c(c3)O[C@@H](C)C4)CC2)s1] | Chiral SFC Method B: 1st eluting compound |
| 17 | 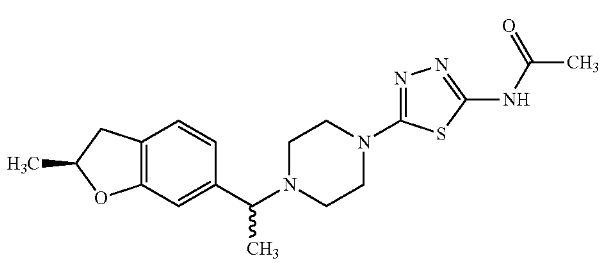 [SMILES: CC(=O)Nc1nnc(N2CCN(C(C)c3ccc4c(c3)O[C@@H](C)C4)CC2)s1] | Chiral SFC Method B: 2nd eluting compound |

| No | Structure | Configuration specification |
|---|---|---|
| 18 | 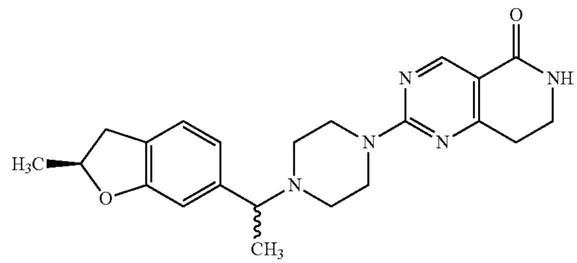 [SMILES: CC(c1ccc2c(c1)O[C@@H](C)C2)N1CCN(c2ncc3c(n2)CCNC3=O)CC1] | Chiral SFC Method C: 1st eluting compound |
| 19 | 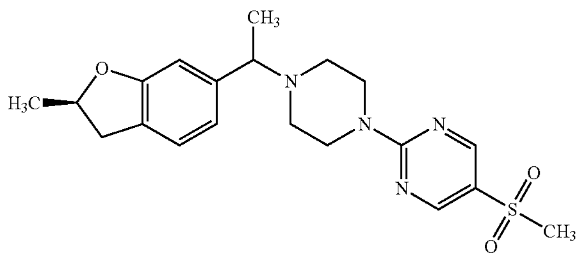 | Synthesized from (R)-propane-1,2-diol |
| 20 | 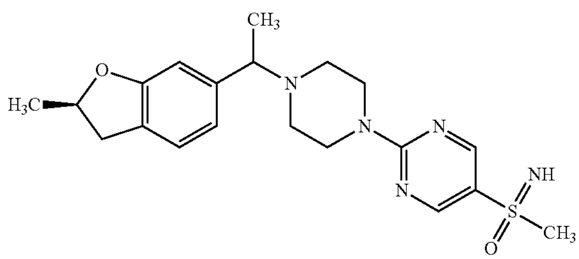 | Synthesized from (R)-propane-1,2-diol |
| 21 | | Synthesized from (R)-propane-1,2-diol | and/or and pharmaceutically usable derivatives, solvates, salts, tautomers, enantiomers, racemates and stereoisomers thereof, including mixtures thereof in all ratios.

11. A compound of formula (I) according to claim 1 for use as a medicament.

12. A compound of formula (I) according to claim 1 and pharmaceutically usable derivatives, solvates, salts, tautomers, enantiomers, racemates and stereoisomers thereof, including mixtures thereof in all ratios for use in a treatment of a condition selected from neurodegenerative diseases, diabetes, cancer, cardiovascular diseases and stroke.

13. A compound for use in a treatment of a condition according to claim 12, wherein the condition is selected from the group of one or more tauopathies and Alzheimer's disease, Dementia, Amyotrophic lateral sclerosis (ALS), Amyotrophic lateral sclerosis with cognitive impairment (ALSci), Argyrophilic grain disease, Behavioural variant frontomeporal dmenetia (BvFTD), Bluit disease, Chronic traumatic encephalopathy, Corticobasal degeneration (CBP), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Frontotemporal lobar degeneration (FTLD), Ganglioglioma, Gangliocytoma, Gerstmann-Straussler-Scheinker disease, Globular glia tauopathy, Guadeloupean parkinsonism, Hallevorden-Spatz disease (neurodegeneration with brain iron accumulation type 1), Lead encephalopathy, Lipofuscinosis, Meningioangiomatosis, Multiple system atrophy, Myotonic dystrophy, Niemann-Pick disease (type C), Pallido-ponto-nigral degeneration, Parkinsonism-dementia complex of Guam, Pick's disease (PiD), Parkinson's disease dementia, Postencephalitic parkinsonism (PEP), Primary progressive aphasia, Prion diseases (including Creutzfeldt-Jakob Disease (GJD), Progressive nonfluent aphasia, Variant Creutzfeldt-Jakob Disease (vCJD), Fatal Familial Insomnia, Kuru, Progressive supercortical gliosis, Progressive supranuclear palsy (PSP), Semantic dementia, Steele-Richardson-Olszewski syndrome, Subacute sclerosing panencephalitis, Tangle-only dementia, Tuberous sclerosis, Huntington's disease and Parkinson's disease, preferably one or more tauopathies and Alzheimer's disease.

14. A method for treating a tauopathy, wherein a compound defined in claim 1 is administered to a mammal in need of such treatment.

15. A method for inhibiting a glycosidase, wherein a system expressing the glycosidase is contacted with a compound as defined in claim 1 under in-vitro conditions such that the glycosidase is inhibited.

16. A pharmaceutical composition comprising as active ingredient a compound according to claim 1 together with pharmaceutically tolerable adjuvants and/or excipients, optionally in combination with one or more further active ingredients.

* * * * *

UNITED STATES PATENT AND TRADEMARK OFFICE
CERTIFICATE OF CORRECTION

PATENT NO. : 10,995,090 B2  
APPLICATION NO. : 16/488163  
DATED : May 4, 2021  
INVENTOR(S) : Anna Quattropani et al.

Page 1 of 1

It is certified that error appears in the above-identified patent and that said Letters Patent is hereby corrected as shown below:

In the Claims

At Column 103, Claim number 1, Line number 57-61:

" 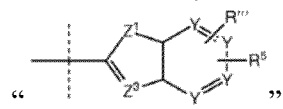 "

Should read:

-- 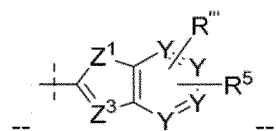 --

Signed and Sealed this  
Fourteenth Day of September, 2021

Drew Hirshfeld  
*Performing the Functions and Duties of the*  
*Under Secretary of Commerce for Intellectual Property and*  
*Director of the United States Patent and Trademark Office*